(12) United States Patent
Guegler et al.

(10) Patent No.: US 6,410,294 B1
(45) Date of Patent: Jun. 25, 2002

(54) ISOLATED HUMAN KINASE PROTEINS, NUCLEIC ACID MOLECULES ENCODING HUMAN KINASE PROTEINS, AND USES THEREOF

(75) Inventors: Karl Guegler, Menlo Park, CA (US); Karen A. Ketchum, Germantown, MD (US); Valentina Di Francesco, Rockville, MD (US); Ellen M. Beasley, Darnestown, MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/734,673

(22) Filed: Dec. 13, 2000

(51) Int. Cl.[7] ............... C12N 9/12; C12N 1/20; C12N 15/00; C12N 5/00; C07H 21/04
(52) U.S. Cl. ............ 435/194; 435/320.1; 435/325; 435/252.3; 536/23.2
(58) Field of Search ............... 435/194, 320.1, 435/325, 252.3; 536/23.2

(56) References Cited

FOREIGN PATENT DOCUMENTS

WO 0073469 * 12/2000

* cited by examiner

*Primary Examiner*—Rebecca E. Prouty
*Assistant Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 29 Drawing Sheets

```
   1 CTACCACGTT CACTGCCTTC CTCTCACTAA AGCCGAGAGG GAGGCTGCTC
  51 AGCTCTCAGG AAAACTCTTT TGAACCCTGG GCACCTGCTG TCCTCAGTTG
 101 GCATCTCCCA CCCTCTGAGC CTCTTCTGTT CCTGCACAAC CTGCCTCTTC
 151 GCTGAGATGG AGACGTGAGC CCCCGTGGAC GATGACTGCA GTGTATATGA
 201 ATGGAGGTGG CCTGGTGAAC CCCCACTATG CCCGGTGGGA TCGGCGCGAC
 251 AGTGTAGAAA GTGGCTGTCA GACCGAGAGT AGCAAGGAGG GTGAGGAGGG
 301 ACAGCCCCGC CAGCTGACGC CCTTCGAGAA ACTGACACAG GACATGTCCC
 351 AGGATGAGAA GGTGGTGAGG GAGATCACGC TGGGGAAACG GATAGGCTTC
 401 TACCGAATTC GAGGGGAAAT CGGAAGTGGA AACTTCTCCC AAGTGAAGCT
 451 TGGGATTCAC TCCCTAACCA AAGAAAAGGT GGCCATTAAG ATCCTGGACA
 501 AGACCAAGTT AGACCAGAAA ACCCAGAGGC TACTATCCCG AGAAATCTCC
 551 AGCATGGAAA AGCTGCACCA TCCCAACATC ATCCGCCTTT ACGAAGTGGT
 601 GGAGACCCTA TCCAAGCTGC ACTTGGTGAT GGAGTATGCA GGGGGTGGGG
 651 AGCTCTTCGG AAAAATTAGC ACTGAGGGGA AGCTCTCTGA ACCAGAAAGC
 701 AAGCTCATCT TCTCCCAGAT TGTGTCTGCC GTGAAGCACA TGCATGAAAA
 751 CCAAATTATT CATAGAGATC TGAAAGCAGA AAATGTATTC TATACCAGTA
 801 ATACTTGTGT GAAGGTGGGC GATTTTGGAT TCAGCACAGT AAGCAAAAAA
 851 GGTGAAATGC TGAACACTTT CTGTGGGTCT CCTCCCTACG CTGCGCCTGA
 901 ACTCTTCCGG GACGAGCACT ACATCGGCAT TTACGTGGAT ATCTGGGCCT
 951 TGGGGGTGCT TTTGTACTTC ATGGTGACTG GCACCATGCC ATTTCGGGCA
1001 GAAACCGTGG CCAAACTAAA AAAGAGCATC CTCGAGGGCA CATACAGTGT
1051 ACCGCCGCAC GTGTCAGAGC CCTGCCACCG ACTCATCCGA GGAGTCCTTC
1101 AGCAGATCCC CACGGAGAGG TACGGAATCG ACTGCATCAT GAATGATGAA
1151 TGGATGCAAG GGGTGCCATA CCCTACACCT TTGGAACCTT TCCAACTGGA
1201 TCCCAAACAT TTGTCGGAAA CCAGCACTCT CAAGGAAGAA GAAAATGAGG
1251 TCAAAAGCAC TTTAGAACAT TTGGGCATTA CAGAAGAGCA TATTCGAAAT
1301 AACCAAGGGA GAGATGCTCG CAGCTCAATC ACAGGGGTCT ATAGAATTAT
1351 TTTACATAGA GTCCAAAGGA GAAGGCTTTT GGAAAGTGTC CCAGTCATGA
1401 TGCTACCAGA CCCTAAAGAA AGAGACCTCA AAAAAGGGTC CCGTGTCTAC
1451 AGAGGGATAA GACACACATC CAAATTTTGC TCGATTTTAT AAATTGCACT
1501 AGACTGCTTG TAACTAACCA AGATGATTGT TGCTGCTTCT AAAT (SEQ ID NO:1)
```

FEATURES:
Start: 182
Stop: 1490

FIGURE 1A

Homologous proteins:
Top 10 BLAST Hits

```
                                                                    Score      E
gi|7503817|pir||T22427 hypothetical protein F49C5.4 - Caenorhab...   316    4e-85
gi|7296128|gb|AAF51422.1| (AE003587) CG4629 gene product [Droso...   290    3e-77
gi|7290249|gb|AAF45711.1| (AE003422) EG:22E5.8 gene product [Dr...   269    5e-71
gi|7511906|pir||T13741 hypothetical protein EG:22E5.8 - fruit f...   269    5e-71
gi|6760436|gb|AAF28351.1|AF219232_1 (AF219232) qin-induced kina...   264    1e-69
gi|5672676|dbj|BAA82673.1| (AB020480) salt-inducible protein ki...   261    1e-68
gi|11067425|ref|NP_067725.1| salt-inducible protein kinase [Rat...   261    1e-68
gi|7798704|gb|AAF69801.1|AF258462_1 (AF258462) PAR-1 [Drosophil...   260    2e-68
gi|7302464|gb|AAF57549.1| (AE003795) par-1 gene product [alt 1]...   260    3e-68
gi|7595802|gb|AAF64456.1|AF240783_1 (AF240783) ELKL motif kinas...   259    4e-68
```

EST:
```
gi|4618918 /dataset=dbest /taxon=9606 ...                            771    0.0
gi|6142971 /dataset=dbest /taxon=9606 ...                            706    0.0
gi|5741347 /dataset=dbest /taxon=9606 ...                            690    0.0
gi|4072777 /dataset=dbest /taxon=9606 ...                            569    e-160
gi|815466  /dataset=dbest /taxon=9606 /...                           519    e-145
gi|6142973 /dataset=dbest /taxon=9606 ...                            396    e-108
gi|813779  /dataset=dbest /taxon=9606 /...                           347    3e-93
```

EXPRESSION INFORMATION FOR MODULATORY USE:
Expression information from BLAST dbEST hits:
gi|4618918    Primary cancers (no tissue)
gi|6142971    Lung
gi|5741347    Pooled germ cell tumors
gi|4072777    Pooled germ cell tumors
gi|815466     Infant brain
gi|6142973    germ cell
gi|813779     Infant brain Expression information from PCR-based tissue screening panels:
Human brain
Human fetal brain
Human placenta
Human liver
Human kidney
Human bone marrow
Human thyroid

FIGURE 1B

```
  1 MTAVYMNGGG LVNPHYARWD RRDSVESGCQ TESSKEGEEG QPRQLTPFEK
 51 LTQDMSQDEK WREITLGKR IGFYRIRGEI GSGNFSQVKL GIHSLTKEKV
101 AIKILDKTKL DQKTQRLLSR EISSMEKLHH PNIIRLYEVV ETLSKLHLVM
151 EYAGGGELFG KISTEGKLSE PESKLIFSQI VSAVKHMHEN QIIHRDLKAE
201 NVFYTSNTCV KVGDFGFSTV SKKGEMLNTF CGSPPYAAPE LFRDEHYIGI
251 YVDIWALGVL LYFMVTGTMP FRAETVAKLK KSILEGTYSV PPHVSEPCHR
301 LIRGVLQQIP TERYGIDCIM NDEWMQGVPY PTPLEPFQLD PKHLSETSTL
351 KEEENEVKST LEHLGITEEH IRNNQGRDAR SSITGVYRII LHRVQRKKAL
401 ESVPVMMLPD PKERDLKKGS RVYRGIRHTS KFCSIL (SEQ ID NO:2)
```

FEATURES:
Functional domains and key regions:
[1] PDOC00001 PS00001 ASN_GLYCOSYLATION
N-glycosylation site 84-87 NFSQ

[2] PDOC00004 PS00004 CAMP_PHOSPHO_SITE
cAMP- and cGMP-dependent protein kinase phosphorylation site

```
Number of matches: 2
     1    21-24 RRDS
     2   417-420 KKGS
```

[3] PDOC00005 PS00005 PKC_PHOSPHO_SITE
Protein kinase C phosphorylation site

```
Number of matches: 6
     1    33-35 SSK
     2   114-116 TQR
     3   221-223 SKK
     4   311-313 TER
     5   349-351 TLK
     6   429-431 TSK
```

[4] PDOC00006 PS00006 CK2_PHOSPHO_SITE
Casein kinase II phosphorylation site

```
Number of matches: 10
     1    33-36 SSKE
     2    46-49 TPFE
     3    56-59 SQDE
     4   108-111 TKLD
     5   123-126 SSME
     6   169-172 SEPE
     7   282-285 SILE
     8   332-335 TPLE
     9   349-352 TLKE
    10   359-362 STLE
```

FIGURE 2A

[5] PDOC00007 PS00007 TYR_PHOSPHO_SITE
Tyrosine kinase phosphorylation site 281-288 KSILEGTY

[6] PDOC00008 PS00008 MYRISTYL
N-myristoylation site 425-430 GIRHTS

[7] PDOC00009 PS00009 AMIDATION
Amidation site 67-70 LGKR

[8] PDOC00266 PS00294 PRENYLATION
Prenyl group binding site (CAAX box)

433-436 CSIL

[9] PDOC00100 PS00107 PROTEIN_KINASE_ATP
Protein kinases ATP-binding region signature 80-103 IGSGNFSQVKLGIHSLTKEKVAIK

[10] PDOC00100 PS00108 PROTEIN_KINASE_ST
Serine/Threonine protein kinases active-site signature 192-204 IIHRDLKAENVFY <u>Membrane spanning structure and domains:</u>
| Helix | Begin | End | Score | Certainty |
|---|---|---|---|---|
| 1 | 257 | 277 | 1.769 | Certain |

FIGURE 2B

BLAST Alignment to Top Hit:
>gi|7503817|pir||T22427 hypothetical protein F49C5.4 - Caenorhabditis
    elegans >gi|3877329|emb|CAB04433.1| (Z81544) contains
    similarity to Pfam domain: PF00069 (Eukaryotic protein
    kinase domain), Score=306.1, E-value=1.4e-88, N=1
    [Caenorhabditis elegans]
    Length = 334

Score =  316 bits (801), Expect = 4e-85
 Identities = 153/299 (51%), Positives = 211/299 (70%)
 Frame = +1

Query: 190  EITLGKRIGFYRIRGEIGSGNFSQVKLGIHSLTKEKVAIKILDKTKLDQKTQRLLSREIS  369
            ++ LG+RIGFYR+  E+G+GNFS+VKLG+H LTKEKVA+KI+DK K+D K Q+LLSREI
Sbjct: 39   QVALGRRIGFYRLGKELGAGNFSKVKLGVHQLTKEKVAVKIMDKAKMDAKAQKLLSREIQ  98

Query: 370  SMEKLHHPNIIRLYEVVETLSKLHLVMEYAGGGELFGKISTEGKLSEPESKLIFSQIVSA  549
            +ME+++HPNI++L+EVVETL+++HLV+EYA GGEL+ +   GKL+E ++K +F+QIVSA
Sbjct: 99   AMEEMNHPNIVKLFEVVETLTRVHLVIEYASGGELYTYVHERGKLTEGDAKPLFAQIVSA  158

Query: 550  VKHMHENQIIHRDLKAENVFYTSNTCVKVGDFGFSTVSKKGEMLNTFCGSPPYAAPELFR  729
            V HMH   I+HRD+KAENV ++S   VK+ DFGFS + + +ML TFCGSPPYAAPELF+
Sbjct: 159  VSHMHSRNIVHRDIKAENVMFSSPNTVKLVDFGFSCLVDREQMLRTFCGSPPYAAPELFQ  218

Query: 730  DEHYIGIYVDIWALGVLLYFMVTGTMPFRAETVAKLKKSILEGTYSVPPHVSEPCHRLIR  909
            D   Y G  VD+WALGVLL+FM+  G  PF+AETV  +K   I G Y +P +VS    LI+
Sbjct: 219  DTSYAGELVDVWALGVLLFFMLIGVTPFKAETVPDMKVLITAGKYQIPDYVSLLATELIK  278

Query: 910  GVLQQIPTERYGIDCIMNDEWMQGVPYPTPLEPFQLDPKHLSETSTLKEEENEVKSTLE  1086
            +L+    +R  ID +   WM+         +   +LS +T K +  E K  ++
Sbjct: 279  SMLKTDTGQRADIDSVKKHFWMRDC---------RFTKSYLSIKATAKIDNEEEKKAID  328
(SEQ ID NO :4)

>gi|7296128|gb|AAF51422.1| (AE003587) CG4629 gene product
    [Drosophila melanogaster]
    Length = 550

Score =  290 bits (734), Expect = 3e-77
 Identities = 143/262 (54%), Positives = 193/262 (73%), Gaps = 6/262 (2%)
 Frame = +1

Query: 190  EITLGKRIGFYRIRGEIGSGNFSQVKLGIHSLTKEKVAIKI--LDKTKLDQKTQRLLSRE  363
            ++T+G+RIG YR  G+IG GNFS+VKL +H LT++KVAIK+    LD+   LD K R+LS E
Sbjct: 34   QVTIGRRIGLYRFCGDIGRGNFSKVKLAVHQLTRDKVAIKVVDLDRAGLDAKALRMLSSE  93

Query: 364  ISSMEKLHHPNIIRLYEVVETLSKLHLVMEYAGGGELFGKISTEGKLSEPESKLIFSQIV  543
            I+++E +HHPNI+RL+EVVETL  +++LV E+  GGEL+  I+  G L E  +  Q++
Sbjct: 94   IATLECVHHPNILRLFEVVETLGRVYLVTEWIRGGELYNHITQGGPLREIHAAPLLKQLL  153

Query: 544  SAVKHMHENQIIHRDLKAENVFYTSNTCVKVGDFGFSTVSKKG----EMLNTFCGSPPYA  711
             AVKHMH    +HRD+KAENV    S   +K+ DFGFST   G      + L+TFCGSPPYA
Sbjct: 154  LAVKHMHSLGYVHRDIKAENVLLLSEDRLKLADFGFSTQLINGTGANQKLDTFCGSPPYA  213

FIGURE 2C

```
Query:  712 APELFRDEHYIGIYVDIWALGVLLYFMVTGTMPFRAETVAKLKKSILEGTYSVPPHVSEP 891
            APELF D+HYIG  VD+WALG+LLYFMV G MPFRA T+   LK +IL+G Y +P  +S P
Sbjct:  214 APELFSDDHYIGAPVDVWALGILLYFMVVGNMPFRAPTIPGLKAAILKGDYLLPGQLSLP 273

Query:  892 CHRLIRGVLQQIPTERYGIDCIMNDEWM 975
            C RLI+ +L   IP +R  ID ++N +++
Sbjct:  274 CIRLIQRILIHIPAQRPTIDDMLNSQFV 301  (SEQ ID NO:5)
```

Score = 41.4 bits (95), Expect = 0.022
Identities = 24/72 (33%), Positives = 40/72 (55%), Gaps = 2/72 (2%)
Frame = +1

```
Query: 1021 PKHLSETSTLKEEENEVKSTLEHLGITEEHIRNNQGRDARSSITGVYRIILHRVQRKK-- 1194
            P +  +S L  EE +  L  LG+T E + N +    RS I G YRI+++R+Q++
Sbjct:  465 PTNTEDLSQLGALEFEARQILAELGLTSEMLINARQSGPRSDIIGAYRIVVNRLQKQSWL 524

Query: 1195 ALESVPVMMLPDPK 1236
            A + V + +  +PK
Sbjct:  525 ARKHVEMALHSEPK 538  (SEQ ID NO:6)
```

HMM results:

| Model | Description | Score | E-value | N |
|---|---|---|---|---|
| PF00069 | Eukaryotic protein kinase domain | 297.2 | 2.1e-85 | 1 |
| CE00022 | CE00022 MAGUK_subfamily_d | 18.4 | 2.5e-05 | 1 |
| CE00334 | E00334 urotrophin_receptor | 10.0 | 0.0039 | 1 |
| CE00031 | CE00031 VEGFR | 4.7 | 0.15 | 1 |
| CE00359 | E00359 bone_morphogenetic_protein_receptor | 2.3 | 5.6 | 1 |
| CE00203 | CE00203 ERBB_RECEPTOR | 0.7 | 7.7 | 1 |
| CE00287 | CE00287 PTK_Eph_orphan_receptor | -18.9 | 5.1e-07 | 1 |
| CE00292 | CE00292 PTK_membrane_span | -42.0 | 1.3e-06 | 1 |
| CE00291 | CE00291 PTK_fgf_receptor | -67.0 | 7.1e-05 | 1 |
| CE00286 | E00286 PTK_EGF_receptor | -107.4 | 0.00017 | 1 |
| CE00290 | CE00290 PTK_Trk_family | -115.8 | 1.9e-07 | 1 |
| CE00016 | CE00016 GSK_glycogen_synthase_kinase | -210.3 | 5.2e-05 | 1 |
| CE00288 | CE00288 PTK_Insulin_receptor | -234.2 | 0.92 | 1 |

Parsed for domains:

| Model | Domain | seq-f | seq-t | hmm-f | hmm-t | score | E-value |
|---|---|---|---|---|---|---|---|
| CE00031 | 1/1 | 193 | 216 .. | 1068 | 1091 .. | 4.7 | 0.15 |
| CE00203 | 1/1 | 189 | 216 .. | 858 | 885 .. | 0.7 | 7.7 |
| CE00334 | 1/1 | 193 | 218 .. | 678 | 703 .. | 10.0 | 0.0039 |
| CE00359 | 1/1 | 192 | 218 .. | 272 | 298 .. | 2.3 | 5.6 |
| CE00288 | 1/1 | 76 | 290 .. | 1 | 269 [] | -234.2 | 0.92 |
| CE00286 | 1/1 | 74 | 306 .. | 1 | 263 [] | -107.4 | 0.00017 |
| CE00292 | 1/1 | 74 | 323 .. | 1 | 288 [] | -42.0 | 1.3e-06 |
| CE00290 | 1/1 | 71 | 323 .. | 1 | 282 [] | -115.8 | 1.9e-07 |
| CE00291 | 1/1 | 78 | 323 .. | 1 | 285 [] | -67.0 | 7.1e-05 |
| CE00287 | 1/1 | 74 | 323 .. | 1 | 260 [] | -18.9 | 5.1e-07 |
| CE00022 | 1/1 | 179 | 325 .. | 129 | 283 .. | 18.4 | 2.5e-05 |
| PF00069 | 1/1 | 74 | 325 .. | 1 | 278 [] | 297.2 | 2.1e-85 |
| CE00016 | 1/1 | 6 | 370 .. | 1 | 433 [] | -210.3 | 5.2e-05 |

FIGURE 2D

```
   1 AAAGCACAAG TTCCTGCCCA CCTGGTGCTT TTTTTTTTTT TCAGATGGCG
  51 TTTCACTCTT GTCGCCCACG CTGGAGTGCA ATGGCATGAT CTCAGCTCAC
 101 TGCACCCTCT GCCTCCTGGG TTCAAACAAT TCTCCTGCCT CAGCCTCCCA
 151 AGTAGCTGGG ATTACAGGTG TGCGCCACCA TGCTTGGCTA ATTTTTGTAT
 201 TTTTAGTAGA GATGGAGTTT CACCATGTTG GCCAGGCTGG TCTCAAACTC
 251 CTAACCTCAG GTGATCCACC CACCTCAGCC TCCCAAAGTG TTGGGATTAC
 301 AGGCTTGAGC CACTGTGCCC GGCGCCCTCC TAGTGCTGAT GTAGTTGTGG
 351 CCCAAGTACA TTAGTGACAA GGACAGCACA GTAATGAGGA CACAGAGCCA
 401 GTAAGTTCTT CAGAGAGTCT GTTAGAACAC AAAGTGATCA AAGTGATCAA
 451 AAGTACTGCA TTCTATGGAA AATCTATATT TTTCTTTTTC CTTAGGTTAA
 501 GCTAAAGTTT CTTGCAGAAT TACTACTTCA TTCTAGTCTG TCATAAGCTG
 551 CATGGTGTTT TTCTGCCAGG AATCTGGGGA GATCTAGTGC CACTTGACCT
 601 TCACAGAGAT TCTTAACCTG ATGGGTTTCA GAATGTCATC TTAAAATTGG
 651 ATGCAAATTG TATGGGTGAG GGTTTTTTTT TTTTTCCTCC TGGGGATAAA
 701 GTCATAGGTT TTGTTAGCAT CTCAAAGGAG TCTGTGAGCC AGGATGATT
 751 AAGAATCAGT GATTTTGGCT GAGTACAGTG GTTCACACCT GTAATTCCAG
 801 CACTTTGGGA GGTAGAGGTG GGTAAAGAAA AGGAAGAAGA ATCAGTGACT
 851 TAGATTTTCT TCACTCTAAT TAAGGACCTT TACCTTTTTT GTTTGTTTGC
 901 TTTGCTTTGT TTTTTTGAGA CAGGGTCCGG CATTGTCACC CAGGCTGGAG
 951 TACAGTGGCT TGATCTCAGC TCACTGCAAC CTCCACTTCC TGGGCTCAAG
1001 CCATCCTCCC ACCTCAGTCT GTAGGTGTAG CTGAGACTAC AGGTGCACAC
1051 CCTGCTAAGG GGTACACCAC CACACCCTGC TAGGAGGTAC AACACCACAC
1101 CCTGCTAAGG GGAACTTTAT ACTTAAAAAT GTTTTTAAAA AACATCCTAA
1151 TTGGTCTCTA ACCTAGAGAT GTGCTTAGTT ACTGATACCT GGTCCCTTTT
1201 AAGCCTATGT TCGTCATCCT TCTTCCAGAT TCCTTTCTCT CTATCCAGAA
1251 ATAGGAGCAG TACTGGGCAT CAACCTCCTC TTTACTTCCC TTATTTATGT
1301 TTATTTGGCA ACCCCATACT TAACCTTAAG TATAAGCTTA GGAAGCCTTA
1351 TTTATACTTA ATTGTAATAA TGTGATATTA TTGAGCAGAG TTGGAAATCC
1401 ATACTTCCAA GGCAGTCTCT CATGTTTTCA GTCAAATTTT TGGTTTGGAA
1451 TGCTCAAGTC CAAAAATCAA GTTAACACA TATTTACTTA GTAAACACTT
1501 TCTATATGTA AGAACTTATA CTCCATTTTG AAGGAGAGAG GAGGTGAGCA
1551 GGACATACCT ACAAGTCAAA ACCAGTTCCC ACCTTCACTG AGATGGGACA
1601 TTTTGGAAAA TGCACGAAGT GCTGTGGGAA TTCAGAGAGG AAGAGAGTAT
1651 TTCCTGCTGG AGAGTGCAGA AAAAAAACAT CCCGATGACA TCGTAGGTGG
1701 GCAGCATTTC TTGTCACTGG CAATGCTGTA AACCCTCCTT TTCCACATCT
1751 TCAAAATAAG GTGCTGGGCC TAGAAACTGA CACCTGCTCA GAAAAATTCA
1801 AAAAGTGAAT GTAGGAGGAA AAATCAGCCT TTGTCATAAA ATGACATAGG
1851 AAGAAAGAGT GGAAGCAACT AGTATAGGAC AAGTTGTGCA AGAACATGAA
1901 GTAGTAAAGG AGATAAAATA TTATTATTTG AATAAATATG AGAAATTTTG
1951 AAAACCATTA GTAATCCGGA ATCTTTCATC TTTGCTATCA TATTATTTTT
2001 AAAATTTGGT TTTAAAGCAA CACAAGGCAA TGTGCATATT TTCTTAAACT
2051 TTAAGAAATA GAAAAATTGT TTTGCTAGAA ATATGTACGG ACCTTAGGGG
2101 CTTTTCTAAA ATGTAGGTTG AGAGGTGTGT GTATATGCTC TTTTCTTCTT
2151 ACTAGATCAC ATGTAATCAA GCATCTACTA CTGATATGAG TCATAAATTT
2201 GTGGGTACT TTTAGATCAA TGCTTACAAA GCAGTTGCAC ATTCATTACA
2251 AATCCTGTAC AGTACATTAG CATAAGCTAA TAAATTTCTT ACTCTCTATT
2301 CTTAGGTTGA ACCAGCCAAA TTTTCGAGAC AGCTCACGGC TTAGAGGAAG
2351 GTTCATCTAA ATAAAGGCCG GCTAAAGTGA CATTGCAGGG ATTAAATCCT
2401 TCTTTGGCTG CCTGTGTGAC CAGAAGGCTT ATTTGCAAGT TTCTTCTTTC
2451 CTGGGGTCCA GATTATTAGG TCTCCAGCGC CCTGCAGCTT GACAGAAAGA
2501 GAAGCATGAA ATGAAGGTCA GAGATGAGAT CCCGCAGCAG GGACGTGGGG
2551 GCCTCCCAGG GGCATTTACG CACCAGAGTG CAAGATTCTC TGGCCATCAA
2601 GGGAAATAGC AAACAGAAGC CTTTGTCCTG GGGCACAGCC ACCTACCACA
2651 AAGCATCAGA CTCCACGTCT GGCCAGAAAG TTCCTGGAGT CCCATCAGGC
```

FIGURE 3A

```
2701 CAGTGGGTAT GTAACATGTG CCTAATTGTA CAGCTAGAGC CTGCAAGTTC
2751 AACGTGAGGG AAGGTGGGAA ATGTCTTGAG TGAGGCGAGC AGCTCCTGGC
2801 TGGGCTGGGC AGACTCAGCT ACCACGTTCA CTGCCTTCCT CTCACTAAAG
2851 CCGAGAGGGA GGCTGCTCAG CTCTCAGGAA AACTCTTTTG AACCCTGGGC
2901 ACCTGCTGTC CTCAGTTGGC ATCTCCCACC CTCTGAGCCT CTTCTGCTCC
2951 TGCACAACCT GCCTCTTCGC TGAGATGGAG ACGTGAGCCC CCGTGGACGA
3001 TGACTGCAGT GTATATGAAT GGAGGTGGCC TGGTGAACCC CCATTATGCC
3051 CGGTGGGATC GGCGCGACAG TGTAGAAAGT GGCTGTCAGA CCGAGAGTAG
3101 CAAGGAGGGT GAGGAGGGAC AGCCCCGCCA GCTGACGCCC TTCGAGAAAC
3151 TGACACAGGA CATGTCCCAG GATGAGAAGG TGGTGAGGGA GATCACGCTG
3201 GGGAAACGGA TAGGCTTCTA CCGAATTCGA GGGGAAATCG GAAGTGGAAA
3251 CTTCTCCCAA GTGAAGCTTG GGATTCACTC CATAACCAAA GGTAGGATCC
3301 GACTTCCCAA GGGTCATCCC TGGCAGTATT GGGACCTAGT GTAGGAAAGG
3351 GGTTAGGTGG CCAGGGCCAA GGAAGCAAGT AAAGTGACCT CAGCAGAGCC
3401 CCTGCAAGGC CCACATCCTG TGCCAGCCGC CTTCTGTGGT CTTCTCAGTT
3451 AATTTTCACA GTAACCATGT GAGGTCAATA TTTTTTTCCA TTTTGCAGAT
3501 AAAGAAACTG AGATCCAAAG AAGGCAAATG TGTCTTCAGT TCNNNNNNNN
3551 NNNNNNNNNN NNNNNNNNNN NNNNNNNNNN NNNNNNNNNN NNNNNNNNNN
3601 NNNNNNNNNN NNNNNNNNNN NNNNNNNNNN NNNNNNNNNN NNNNNNNNNN
3651 NNNNNNNNNN NNNNNNNNNN NNNNNNNNNN NNNNNNNNNN NNNNNNNNNN
3701 NNNNNNNNNN NNNNNNNNNN NNNNNNNNNN NNNNNNNNNN NNNNNNNNNN
3751 NNNNNNNNNN NNNNNNNNNN NNNNNNNNNN NNNNNNNNNN NNNNNNNNNN
3801 NNNNNNNNNN NNNNNNNNNN NNNNNNNNNN NNNNNNNNNN NNNNNNNNNN
3851 NNNNNNNNNN NNNNNNNNNN NNNNNNNNNN NNNNNNNNNN NNNNNNNNNN
3901 NNNNNNNNNN NNNNNNNNNN NNNNNNNNNN NNNNNNNNNN NNNNNNNNNN
3951 NNNNNNNNNN NNNNNNNNNN NNNNNNNNNN NNNNNNNNNN NNNNNNNNNN
4001 NNNNNNNNNN NNNNNNNNNN NNNNNNNNNN NNNNNNNNNN NNNNNNNNNN
4051 NNNNNNNNNN NNNNNNNNNN NNNNNNNNNN NNNNNNNNNN NNNNNNNNNN
4101 NNNNNNNNNN NNNNNNNNNN NNNNNNNNNN NNNNNNNNNN NNNNNNNNNN
4151 NNNNNNNNNN NNNNNNNNNN NNNNNNNNNN NNNNNNNNNN NNNNNNNNNN
4201 NNNNNNNNNN NNNNNNNNNN NNNNNNNNNN NNNNNNNNNN NNNNNNNNNN
4251 NNNNNNNNNN NNNNNNNNNN NNNNNNNNNN NNNNNNNNNN NNNNNNNNNN
4301 NNNNNNNNNN NNNNNNNNNN NNNNNNNNNN NNNNNNNNNN NNNNNNNNNN
4351 NNNNNNNNNN NNNNNNNNNN NNNNNNNNNN NNNNNNNNNN NNNNNNNNNN
4401 NNNNNNNNNN NNNNNNNNNN NNNNNNNNNN NNNNNNNNNN NNNNNNNNNN
4451 NNNNNNNNNN NNNNNNNNNN NNNNNNNNNN NNNNNNNNNN NNNNNNNNNN
4501 NNNNNNNNNN NNNNNNNNNN NNNNNNNNNN NNNNNNNNNN NNNNNNNNNN
4551 NNNNNNNNNN NNNNNNNNNN NNNNNNNNNN NNNNNNNNNN NNNNNNNNNN
4601 NNNNNNNNNN NNNNNNNNNN NNNNNNNNNN NNNNNNNNNN NNNNNNNNNN
4651 NNNNNNNNNN NNNNNNNNNN NNNNNNNNNN NNNNNNNNNN NNNNNNNNNN
4701 NNNNNNNNNN NNNNNNNNNN NNNNNNNNNN NNNNNNNNNN NNNNNNNNNN
4751 NNNNNNNNNN NNNNNNNNNN NNNNNNNNNN NNNNNNNNNN NNNNNNNNNN
4801 NNNNNNNNNN NNNNNNNNNN NNNNNNNNNN NNNNNNNNNN NNNNNNNNNN
4851 NNNNNNNNNN NNNNNNNNNN NNNNNNNNNN NNNNNNNNNN NNNNNNNNNN
4901 NNNNNNNNNN NNNNNNNNNN NNNNNNNNNN NNNNNNNNNN NNNNNNNNNN
4951 NNNNNNNNNN NNNNNNNNNN NNNNNNNNNN NNNNNNNNNN NNNNNNNNNN
5001 NNNNNNNNNN NNNNNNNNNN NNNNNNNNNN NNNNNNNNNN NNNNNNNNNN
5051 NNNNNNNNNN NNNNNNNNNN NNNNNNNNNN NNNNNNNNNN NNNNNNNNNN
5101 NNNNNNNNNN NNNNNNNNNN NNNNNNNNNN NNNNNNNNNN NNNNNNNNNN
5151 NNNNNNNNNN NNNNNNNNNN NNNNNNNNNN NNNNNNNNNN NNNNNNNNNN
5201 NNNNNNNNNN NNNNNNNNNN NNNNNNNNNN NNNNNNNNNN NNNNNNNNNN
5251 NNNNNNNNNN NNNNNNNNNN NNNNNNNNNN NNNNNNNNNN NNNNNNNNNN
5301 NNNNNNNNNN NNNNNNNNNN NNNNNNNNNN NNNNNNNNNN NNNNNNNNNN
5351 NNNNNNNNNN NNNNNNNNNN NNNNNNNNNN NNNNNNNNNN NNNNNNNNNN
```

FIGURE 3B

```
5401 NNNNNNNNNN NNNNNNNNNN NNNNNNNNNN NNNNNNNNNN NNNNNNNNNN
5451 NNNNNNNNNN NNNNNNNNNN NNNNNNNNNN NNNNNNNNNN NNNNNNNNNN
5501 NNNNNNNNNN NNNNNNNNNN NNNNNNNNNN NNNNNNNNNN NNNNNNNNNN
5551 NNNNNNNNNN NNNNNNNNNN NNNNNNNNNN NNNNNNNNNN NNNNNNNNNN
5601 NNNNNNNNNN NNNNNNNNNN NNNNNNNNNN NNNNNNNNNN NNNNNNNNNN
5651 NNNNNNNNNN NNNNNNNNNN NNNNNNNNNN NNNNNNNNNN NNNNNNNNNN
5701 NNNNNNNNNN NNNNNNNNNN NNNNNNNNNN NNNNNNNNNN NNNNNNNNNN
5751 NNNNNNNNNN NNNNNNNNNN NNNNNNNNNN NNNNNNNNNN NNNNNNNNNN
5801 NNNNNNNNNN NNNNNNNNNN NNNNNNNNNN NNNNNNNNNN NNNNNNNNNN
5851 NNNNNNNNNN NNNNNNNNNN NNNNNNNNNN NNNNNNNNNN NNNNNNNNNN
5901 NNNNNNNNNN NNNNNNNNNN NNNNNNNNNN NNNNNNNNNN NNNNNNNNNN
5951 NNNNNNNNNN NNNNNNNNNN NNNNNNNNNN NNNNNNNNNN NNNNNNNNNN
6001 NNNNNNNNNN NNNNNNNNNN NNNNNNNNNN NNNNNNNNNN NNNNNNNNNN
6051 NNNNNNNNNN NNNNNNNNNN NNNNNNNNNN NNNNNNNNNN NNNNNNNNNN
6101 NNNNNNNNNN NNNNNNNNNN NNNNNTTGAC ACATAAAATA AACCATCAGA
6151 GTTGGTAACT GATTGGATGT AGAACTGAAG ATGGAAGGAT GGACGAAGGC
6201 AATGACCTTG CTTTAGTTGA CTATGTGAAC CAAAACAGGT GATGCCTTTA
6251 ATAGGAATAG GAGAAAGAGC AAATTTGGGA GGGAAAAAGT TGAGTGAAAA
6301 CACTGACATC CAGAAGGAGC TGTCTACTGG GCATGCTCCA GTCATGGACA
6351 AGGGCATGAG GTCAGACCAG GTATTTGCAT TGAGAAGATT GTAGAAATGG
6401 ATGCAGTCAC TGAAGGAGAC TGTGGAGAAG GGTGATGAGC AACCTTTTTA
6451 CACTTAGTAA CTAGTTCTAC ATCCTAGTTG ACATTTTATG TATGGATTAG
6501 TTTTTTTTTT TTTTTTTTTT TGAGATGGAG TCTCGCTCTG TTGCCCACGC
6551 TGGAGTGTAG TGGTGTGATC TTGGCTCACT GCAAGCTCTG CCTCCTGGGT
6601 TCATGCCGTT CTCCTGCCTC AACCTCCCGA GGAGCTGGGA CTACAGACAC
6651 CCACCACCAC GCCTGGCTAA TTTTTTGTAT TTTTAGTAGA GACGGGGTTT
6701 CACCATGTTA GCCAGGATGG TCTCGATCTC CTGACCTCGT GATCTGCCCG
6751 CCTCGGCCTC CCAAAGTGCT GGGATTACAG GCATGAGCCA CCGCGCCTGG
6801 CCGGATTAGT TTTAAATATG CTAATGGAAT CATTCACTGT TGCTCCATGA
6851 ACACTATGAT TTTTCAATGT CATTAAATAT AGATTTTTAA AATATATTTA
6901 TGTGTATATA TTATCTATAT ATGTGTATTT ATTATCTATA CTCTCATCTT
6951 TTAAAGAGGA CATATTGTTT CACATATAGC TGTGGCATAA ATTCTTTAAC
7001 TTAGCCACTA TTGGTTAACA TTTGGATCAT TTCTAAAGTT TTGCTCTTAA
7051 TTATAATGCT ACAGAGATTA TTCTTTTCCA TACTTCTTTG CATATACGTA
7101 TGATTTCTCT CAGCATACAT TCCTAGAAGT TAGCTGTCTT GGTCAGAGGG
7151 CATGCATTGA AAAATTTTAA CACACAGCAC CAAAAGAGCA GCTTTTGAAT
7201 CCTTACTCAT AGAGTACATC TATCTGTAAC TCAAATCTCA CAGGGACTAA
7251 TGTTGCTTTT CAATAGTCTA GAGCCAGCAT GAAAGACAAA AGATGAAACA
7301 CATAGAGCGA TGAAAGGCCA AAAATCGAGA CAGAAGATGT GATTTGGAAG
7351 GTTACAAGAG AAGTTGGATA AAGCCAAACA AGGAAAGGAA TTTAGAAAAA
7401 AGTGTCCAAT GCTGCAGAAG GGTCACAGAG CTACAGTCTG AGCAAAGGCT
7451 ACTGCATAAG GCCAACTTTG AGAAGTTTCA TACAAGTGTG GGTTCAGATG
7501 TTAGATTCCA ATAGAAAGGA AGCAGGATGG GACAGTAGGA AAAGCGTGGA
7551 CTTGGGGACC AGACAAATTT ATCTGAAATA CTCATTCAGT AACTTACTAG
7601 GCTTCTGACT TTAGGCATAT TAATCTCTTT GGTCCTCAGT TGCCTCAGCT
7651 GTAAAATAGA GATAATGATT TTTAGAATTG TTGGGGAAAT TGGAAATAAT
7701 ATATGTGAAG TACATGACAT ATAGTAACCA CTCAAAATGG TAGCTGCCAT
7751 TGCTATAACT TTACTTTTTA ATTAATCTTA TTTCAAAAAG GTATTTAATG
7801 TTATTACAAC AATAAAAACC AGTATCACTT ACTATGAATA GAAGGTGATG
7851 GTAAAAATAA ATACAATGCA AACAAATTAA AAAGCATTAA AGGAAAATTA
7901 CAAGTAACAA AGTAATTTTT AAAACATGCT AACAATCAAT CTCAGACTTT
7951 CTCTTTGCCT TAATTAGGAG AATTAAAGGA GAGCTGAAAT GGGAATCATG
8001 TTTTTACGCT GTGATTCAGT GCTATTTAAG GCTGTTTCCA CGCCCTAAAA
8051 TCATTTCAAC CTCATGAGTC TTAAAGGTTC CACTTTGGGA AGCACTGACA
```

FIGURE 3C

```
 8101 TCATCTAGTC CTTCCATGTT TTACAAACGA GGAGATGGAG GCTCAGAAGA
 8151 GGCTGTCCCA AGGTTTAGAA CCTGTTTACA GGAATTCACA TGGAATTGAG
 8201 TACTCACATG TATTGAGTAC AGGGGAATTC TATGGACCCA CAGCAGGGAA
 8251 GTAGGGCCGG GTCTTAAGAT GATATTCTTT TGATCTTCAC TTTCTCTGGG
 8301 GCTGTGTGCT TTCTCATTTC TACTTTTCTT GATGAATTTG TTCCATCTTT
 8351 ATACCTCTTT CTGCAAAAAG GTTTTCCACA CTTAATTATC AGAAGGTATA
 8401 TCATGGCCAA AAATGGTTGT TGCCAGTCCC ACATCTACAT AAACTCTCAA
 8451 TGTTATTGAC CGCCTCCATC CCATGTGTTT CATTCTGTTT CAGTTCAAAT
 8501 TTTAAAAAGA AAGAATATAC TTAATTACTA GCCAGCTGAA AATGAACTAC
 8551 CTTTGAGTCA AGGGCATGCC CGTGTCAGTG AGCTGTAACC CTTTGAGTCA
 8601 CGTGGGCCAC TACTGTCTCA GCAGAGCCAA AGGTCCAAAG AAGTCTCTGG
 8651 GAAGGGAGAA AATTGACAGA CATATCCACC ATAGAGACAT TAGCTAGCTA
 8701 AGCCGAGAAG TTTCTACAAG CCGGGAGCAA GACAGTGCCC AATTCTGTAG
 8751 ACAGGATATT ATGTGAAAGG ACAAAAAAAA AAGGTGGAAT AATAATTAGT
 8801 GTTTATATAC TGACTTACTT CTCGGGTTCC AAAGACTTCT TGTCTGTTGT
 8851 ATTACAAAAT TAACTTCAAA CTTGTCCCCA TGAGTTTCAG AGAGCATGGC
 8901 ATTTTCCCAC TGTGTGGGTG TGGGTGGGTG CCTTGTGTGG CCTCACTGAC
 8951 ATGCCCTCCT TATACCTAAC CTGCTACAAA GTAGCTCTAT TGTCAAAGAA
 9001 ACAGTCTCAC CCGCTGGTTC TGGGACAGTA TGTGCAAAAA GGGACAGGAA
 9051 AATAAATAGC AGTTTGTACA AATATGGCCC CCACACCAAA CCAACTTGCC
 9101 CAGAATTGTC ATCCGGTTTT CTAGGAATAT AAGGACAGTT TGAATAAGAT
 9151 AATAGAGGAG ATTCCCAGGA AAGCAGAGAG TTTCAGTGCC AGGAGCAGCT
 9201 CCCAGGACAG TAGTCTAAAA AATTGAAAAA AAAAAAAATA AAGAAATACA
 9251 AAGCACCAAG TGCTCTGGAT CTCTACAAAG GAGGCTCCAA TATGGGTCCC
 9301 TGCTGGCTGG GGTTTATTTT TATAGCTCAC AGTTTGGAAT TCCCTTGGGC
 9351 TCTCCAAGCT GATAGTGAAG GTTGACAGTC ATCATGAGCC CCCTTTTAGG
 9401 CTGATTAGAA ATTTCTCATA AGAGATGATA CACTTAGCTT CTGAATATTT
 9451 TATGTCCCAT CTGTTGTCAC AAACAAAAGA AGTGGCAGCG AATGTGGGTG
 9501 TTTTTTTCTG TTGCTGCCCT TCTGACTTCT TCCTTCTGCT ACTCTAGTCT
 9551 CATGTTTCTA GGATCCTTTC TTCCTCCCAC TTTATTTATC TATTTATCTA
 9601 TTAATTCATT CTTTCCTTCC TTCCTTTTTT TTTTTTTAT CTTTTGAGGA
 9651 AGAGTTTTGC TTCATTGCCC AGGCTGGAGT GCAGTGATGC GATCAAAGCT
 9701 CACTGCTGCC TTGGACTCCT GGGCTCAAGT GATTCACCCA CCTCAGCCTC
 9751 CCAAAGCACT GGGCATTACA GGTGTGAGAC ACCATGACTG GCCTTCATTC
 9801 CTTTATATAT ATATATAATA TAATATATAA TGTAATATAT AATATAATAT
 9851 ATAATATAAT ATATGTGTGT GTGTGTGTGT GTGTGTGTGT GTGTGTGTAA
 9901 GCACATGCCT GATAAGGAAC TTACAGCAGT TTAACAGAGG CAGACAGGAA
 9951 AAAATTGATG AGTGCTGTCC AGAGTAAGGC AGCAAGAATG TGCTTACCTG
10001 TGCCCCGTGG ATCCAGGAAG GGTCTATTGA GCAGGAAAAG CTTGCAATGG
10051 GTCTTGAGGT CTGAGGAGCA ATTTCACAGG AGAAGGAGGA AAGAGAACTC
10101 CAGAAAGAGA GATAGGATAT AAAGTACATG GAAGCATGAA CCAGTGTGGG
10151 GAGTATTTGG AGATTTAAAA GTAATTCAGC AAAGCTAGAG CATGAGGTGC
10201 ACCCACAGAG TCATGGGAAA GAGATAAGGT GGATGGGGCT TGATCATGGA
10251 AAATCTTCTT GCATATCTGG ATTTTGTCAT TTAGGTATTG GAAAGCTACT
10301 GAAGAGTTTT TTTTTTTTTT GAGACGGAGT CTTGCCCTGT CACCCAGCCT
10351 GGAGTACAAT GGTGTGATCT CTGTTCATTG AAACCTCTGC CTCCTGGGTT
10401 CAAGTGATTC TCCTGCCTCA GTCTCCTGAG TAGCTGGGAT TACAGGCACA
10451 CGCCACCATG CTCGGCAATT TTTTTTTGTA TCTTTAGTAG AGATGGGGTT
10501 TCACCATCTT GGCCAGGCTG GTCTCGAATT CCTGACCTCG TGATCCGCCC
10551 GCCTCAGCCT CCCAAAGTGC TGGGATTACA GGCATGAGCC ACTGCGCTCA
10601 GTCGTTTAGG AGCTTTAAGC AAGCCATTAA TGCAAGTGAT TAATATGATC
10651 TTATTTCAGT GCGGAATGTG AATTGAAGTT GGAAAGTAAG GAGAGTCAAG
10701 GAAGTCAGAA AAAAATGTTA GTCAAATGGT CCAGATGGAT GATGTTGTTC
10751 ATCTCAACTA AGGAGAAGTG GCAGTGAGAA TGGAGAGAAG AGCATGTATT
```

FIGURE 3D

```
10801 TGAAAAATGT CTTAGGATAT TGAAAAACCT TGTGATCAAT GGTATGGGTG
10851 AGAGCAGGAC GGGACATGGG AGAGGAAGAA TTGACGATGA CTCCCAGTTT
10901 CCAGTTTTAA TGCCTTACCA GTAAATAATT ACAGGAGAAG TGGATTTGAG
10951 AGTAAATATA TGGAAGCACT GACTTGGAGG TATATGGAAT TCATGAAATG
11001 AATGGGTCTA GCAGCTTTCT TGGAGCCCAA GAGAAAGTAT GATACATAAA
11051 GATTTGAGGC TTAACAAACT CTGGGATGTA GTGACATCTT GGGAGTCCTA
11101 GTTACAAGCT CCTTGGTGTC AGATACTATA TCACATTGAT CCTTAAAGTT
11151 CCTCCATGTG TGTTATAAAT AATAAACACT CGACAAATAT TTGGTGAGTT
11201 AAGTTAGTAT AACTTCTCAT GAAAATCCAG GAGTGGTGGA GGAAGAAATA
11251 TTCGAGGGAG CAATGCATAG CAGCACCTTC TGGTAGGTGC TGTATGCTGT
11301 GATCTCCCTG GAGGACAGGG CTAGAGCACG AACTCAGTCT GTAGCAGAGC
11351 TTCATAAAGA TAGCCCAATG GTTTTGTCGT TTTGCTTTTT CTAGAGATGA
11401 AGTCTCAACT ATGGTTATCC AGGCCGTTCA AGAACTTCTG GGCTCAAGCA
11451 ATCCTCCTGC CTCAGTTTCC TAAGTAGCAT GGGGACAGC TATGCACCAC
11501 TGCACCTGAC TGCTCACTGG TTTTAAAAAT TGATTCCCCC CTCTTGAATA
11551 CATTCATTAA AATAGCAATT CAAAATTGTA TTTTCTTACT TTAAAAATGG
11601 TTAGTTAGTG ATTTAGGGAA TTCACCCTAA AAATAAATCA TATATTGGAA
11651 ATACTACAAC CAAAAAAATG TTCATTGTCG TGTTATTTAT AGTGTCGAGA
11701 ACTAGTAATA ACTTATGGGA TCCAATGATA TAGGAATGGT CAGGTAAAGC
11751 ATATACACTG GGCAGAAGAT TCCATAGCCA TGAGAAATCA TGATTATGAA
11801 GACTCTGTGG TAACATGGAA GATGGGCAGG ACATGAGTGT AAGTGAAAAG
11851 CCAGGTGCAA ATGGAGCGCA CACTATTATG ATAATACTTA CTCCAGGTTC
11901 TTCAGTGAGA TTATTCACTC AGCAAATACT TGTTGAGCAC CTACTATGCA
11951 ATAGCCACTA TTCTAGAGAC TGGTGATACA GCAGTGAACA AAATAGACAG
12001 CAATCTCTGT CCTTATGGAA CTTACACTCT AGTGAGAGGG AAGCCAGACA
12051 AAAATAAATG TGTAAAATAT TCATTGTATT ATGTAGCGAT AAGTGATAAG
12101 AAAGAAAAGA GGGCCGGGCG CGGTCGGTCA CGCCTGTAAT CCCAGCACTT
12151 TGGGAGGCCA AGGTGGGTGG ATTATGAGAT CAAGAGATGG AGGCCATCCT
12201 GGCCGACATG GTGAAACCAC AATTCTACTA AAAATACAAA AATTAGCTGG
12251 GCATGGTGGT GTGCACCTTT AGTCTCAGCT ACTCAGGAGA CTGAGGCAGG
12301 AAAATCGCTT GAACCCAGGA GGGGGAGGTG GCAGTGAGCC AAGATCGTGC
12351 CACTGTACTC CAGCCTGGTG ACAGAGCCAG ACTCTGTCTC AAAAAAAAAA
12401 AAGAAAGAAA GAAAGAAAGA AAGAAAGAAA GAAAGAGCAG GAGGGGAGAT
12451 AGAAAGCATT GAGGATGACA GTTTTTAGAT AAGTTGGCCA GGACAGCCTT
12501 ACTGAGGAGG TAATAATTAA ACTGAAAGAA ATGAGGGAAA TGGCTATACA
12551 TGGGGGAACT CCATCAAGCA GAAGGCGTAG CAGGCGTAAG AGTGTCCAGA
12601 TGGGAGATGC CTGCAGTACT CTTGAAACAG CTGAGGGGAA AGGGCAGAGA
12651 GTAACAGGGA ACAGATTGTG GAGGACCAAG TTTGTCAAAG TAAGAAGTTT
12701 GGCTTTTCCT GGGATTTTAC AGGAGCCATC AGAAGGAACT GGGGATTTCA
12751 CAAAGGGAAC CAGGGATTTC CTGGGATTTC ACAGGAGCCA TCAGAGGGAA
12801 CTGGGGGAGT GACATGATCT GGCTTANNNN NNNNNNNNNN NNNNNNNNNN
12851 NNNNNNNNNN NNNNNNNNNN NNNNNCTTG GGCAACATAG CAAGACCCTG
12901 TCTTTAAAAC CAAAACCAAA ACCAAAAAAA CCACACACAT ATAACCTTTT
12951 TATGTTTAAC GCATATCAAT ACCAAAAAAG TTTAAAAATC ATGAGTATTC
13001 ATTTTGATGA ATTTTCCAAA CTGAAAAGAC CCATGGAAGC ACCACCAACA
13051 TCAAGACACA GAACACTTCT GGTACTCAGA GCGCTGCCCT CCACCTGCTC
13101 GTCATCCTCC ATTCTATTCT CTACATCCTG AAGTGTAACC ACTATTCTGA
13151 CTTCTAATAC CATAGATTGC TTTTGACTGT TTTAAACTTT ACATAAATGG
13201 CATCATCCAA TGTGTATTCT TTGTCTTAC TTCAATTGTC CAATTTTGAG
13251 TTTGTGACTA CCATCCATAC TGTTTTATGT AGTTCAGATG TTTCATGCTC
13301 ATTGCCATAT ATACAGTAAT TCATTGTATG AATGTAGTAC CACAATTTAT
13351 TTATCCATTC AACTGTTGCT GATGTGACTA GTTTCTAGTT TCCAGTTTGG
13401 GGCTATTATG AATAACATTG ATGTGAACAT TCTAGTGCAA GCGTTTTTGG
13451 TAAACTTTTT TTTTTTTTTT GAGGCAGGGT TTTGCTTTGT CACCCAGGCT
```

FIGURE 3E

```
13501 GGAATGTGGT GGCACAATCA CAGCTCACTG CAACCTTGAC TTTCTGTATT
13551 TGAGTGATCC TCCAACCTCA GCCTCTGGAG TAGCTGGAAC CACAGGGGCA
13601 TGCCATCATG CCTGGCTAAT TTTTTAAATG TTTTGTAGAT ATGGGGTCCT
13651 GCTATGTTGC CCAGACTGGT CTCAAACTCC AGGGCTCGAG TAATCCTCTT
13701 GCCTTGGCCT CCCAGAGTGT TGGTATTACA GATGTGAGCC ACTGAGTCTG
13751 GCTCGTATGC ATTTTTATTG GGGACATTTT TACTTATAAA TTTTTTTTCA
13801 ATGACTTTTG GGGTACAAGT GGTTTTTGGT TACAATGATG AACTGTATAC
13851 TGGTGAAATC TTAGATTTTA GTGCACCTAT CACCTGAGTA GTGTACATTG
13901 TACCCAATAC GTAGTTTTTA ATCCCTCACC CCCTCCCACC CTACCCCTTC
13951 TAAGTCTCCA AAGCCCATGC CTTTTCATAC CCATAGCTAA ACTCTCATTT
14001 CTAAGTAAGA ACATACAGTA TTTGATTTTC CATTCCTGAG TTACTTCACT
14051 TGGAACAATG GCCTCCAGCT CCATCCAAGT TGCTGCAAAA TACATTATTT
14101 TATTCTTTTT CATAGCTGAG TAGTATTCTA TGGTATATAC ACCACGTTTT
14151 CTTTACCCAC TCATTGGTTG GTTGACACTT AGGTTGGTTC CAGATCTTTG
14201 CAATTGTGAA TTGTGCTGCC ATAAACATGC ATGCAGGTGT TTTTTGATAT
14251 AAGGACTTCT TTTCCTTTGG GGAGATACCC AGTAGGGGAT TGTTGGATCA
14301 AATGGTAGAT CTACTCTCAG ATTTAGATTT TAATTTACTT TTAGATTTTA
14351 GATTTAGAAA TCTCCATTCT GTTTTCCATA GAGGCTGTAC TAATTTACAT
14401 TCCCACCAGC AGTGTATAAA TGTTACCTTT TCACCACATT CATGCCAACA
14451 TCTACTGTTT TTTGACTTTT TAATAATGAC CATTCTGGCT GGGGTAAAGC
14501 GGTATCTCAC TGTGGTTTTA ATTTGGATTT TTGTGATGAT TAGTGATGTA
14551 GAGTGTTTTT CCATATGTTT GTTGGCCATT TGTATGTCTT CTTTTGAGAA
14601 ATATTTATTC ATATCATTTG CCCACTTTTT AATGAGATCT TTTTTTGTTT
14651 TTTGTTTGCT AATTTGTTTG AGTTCCCTGT AAATTCTGGA TATTAGTTCT
14701 TTGTCAGATA CATAGTTTGC AAATATTTTC TCCCATTCTG TGGATTGCCT
14751 GTTTGCTTTG ATGATTATTT TTTCTGTTGT GCAGAAGCTT TCAGTTTAAT
14801 GAGGTCCCAT TTATTTATTT TTGTTTTTGT TGCATTTACT TTTGGGGTCT
14851 TAGTCACAAA TTCTTATCTA AGTCAATGTC CAGTAGAGTT TTTCCTGTTT
14901 TCTTCTATAA TTTTTGTGGT TTCAGGTCTT AGATTTAAGT CTTTAATCAT
14951 ATTGAGTTGA TTTTTGTATA AGGTGAGTGG GATCCAGTTT TATTCTCCTA
15001 CATGGGCTA TCCAGTTTTC CCAGCAACAT TTACTAAATA GGGTGTCCTT
15051 TCCCTAATTT ATGTTTTTGT ATGCTTTGTT GAAGATCAGT TGGTTGTTAN
15101 NNNNNNNNNN NNNNNNNNNN NNNNNNNNNN NNNNNNNNNN NNNNNNNNNN
15151 NNNNNNNNNN NNNNNNNNNN NNNNNNNNNN NNNNNNNNNN NNNNNNNNNN
15201 NNNNNNNNNN NNNNNNNNNN NNNNNNNNNN NNNNNNNNNN NNNNNNNNNN
15251 NNNNNNNNNN NNNNNNNNNN NNNNNNNNNN NNNNNNNNNN NNNNNNNNNN
15301 NNNNNNNNNN NNNNNNNNNN NNNNNNNNNN NNNNNNNNNN NNNNNNNNNN
15351 NNNNNNNNNN NNNNNNNNNN NNNNNNNNNN NNNNNNNNNN NNNNNNNNNN
15401 NNNNNNNNNN NNNNNNNNNN NNNNNNNNNN NNNNNNNNNN NNNNNNNNNN
15451 NNNNNNNNNN NNNNNNNNNN NNNNNNNNNN NNNNNNNNNN NNNNNNNNNN
15501 NNNNNNNNNN NNNNNNNNNN NNNNNNNNNN NNNNNNNNNN NNNNNNNNNN
15551 NNNNNNNNNN NNNNNNNNNN NNNNNNNNNN NNNNNNNNNN NNNNNNNNNN
15601 NNNNNNNNNN NNNNNNNNNN NNNNNNNNNN NNNNNNNNNN NNNNNNNNNN
15651 NNNNNNNNNN NNNNNNNNNN NNNNNNNNNN NNNNNNNNNN NNNNNNNNNN
15701 NNNNNNNNNN NNNNNNNNNN NNNNNNNNNN NNNNNNNNNN NNNNNNNNNN
15751 NNNNNNNNNN NNNNNNNNNN NNNNNNNNNN NNNNNNNNNN NNNNNNNNNN
15801 NNNNNNNNNN NNNNNNNNNN NNNNNNNNNN NNNNNNNNNN NNNNNNNNNN
15851 NNNNNNNNNN NNNNNNNNNN NNNNNNNNNN NNNNNNNNNN NNNNNNNNNN
15901 NNNNNNNNNN NNNNNNNNNN NNNNNNNNNN NNNNNNNNNN NNNNNNNNNN
15951 NNNNNNNNNN NNNNNNNNNN NNNNNNNNNN NNNNNNNNNN NNNNNNNNNN
16001 NNNNNNNNNN NNNNNNNNNN NNNNNNNNNN NNNNNNNNNN NNNNNNNNNN
16051 NNNNNNNNNN NNNNNNNNNN NNNNNNNNNN NNNNNNNNNN NNNNNNNNNN
16101 NNNNNNNNNN NNNNNNNNNN NNNNNNNNNN NNNNNNNNNN NNNNNNNNNN
16151 NNNNNNNNNN NNNNNNNNNN NNNNNNNNNN NNNNNNNNNN NNNNNNNNNN
```

FIGURE 3F

| | | | | | |
|---|---|---|---|---|---|
| 16201 | NNNNNNNNNN | NNNNNNNNNN | NNNNNNNNNN | NNNNNNNNNN | NNNNNNNNNN |
| 16251 | NNNNNNNNNN | NNNNNNNNNN | NNNNNNNNNN | NNNNNNNNNN | NNNNNNNNNN |
| 16301 | NNNNNNNNNN | NNNNNNNNNN | NNNNNNNNNN | NNNNNNNNNN | NNNNNNNNNN |
| 16351 | NNNNNNNNNN | NNNNNNNNNN | NNNNNNNNNN | NNNNNNNNNN | NNNNNNNNNN |
| 16401 | NNNNNNNNNN | NNNNNNNNNN | NNNNNNNNNN | NNNNNNNNNN | NNNNNNNNNN |
| 16451 | NNNNNNNNNN | NNNNNNNNNN | NNNNNNNNNN | NNNNNNNNNN | NNNNNNNNNN |
| 16501 | NNNNNNNNNN | NNNNNNNNNN | NNNNNNNNNN | NNNNNNNNNN | NNNNNNNNNN |
| 16551 | NNNNNNNNNN | NNNNNNNNNN | NNNNNNNNNN | NNNNNNNNNN | NNNNNNNNNN |
| 16601 | NNNNNNNNNN | NNNNNNNNNN | NNNNNNNNNN | NNNNNNNNNN | NNNNNNNNNN |
| 16651 | NNNNNNNNNN | NNNNNNNNNN | NNNNNNNNNN | NNNNNNNNNN | NNNNNNNNNN |
| 16701 | NNNNNNNNNN | NNNNNNNNNN | NNNNNNNNNN | NNNNNNNNNN | NNNNNNNNNN |
| 16751 | NNNNNNNNNN | NNNNNNNNNN | NNNNNNNNNN | NNNNNNNNNN | NNNNNNNNNN |
| 16801 | NNNNNNNNNN | NNNNNNNNNN | NNNNNNNNNN | NNNNNNNNNN | NNNNNNNNNN |
| 16851 | NNNNNNNNNN | NNNNNNNNNN | NNNNNNNNNN | NNNNNNNNNN | NNNNNNNNNN |
| 16901 | NNNNNNNNNN | NNNNNNNNNN | NNNNNNNNNN | NNNNNNNNNN | NNNNNNNNNN |
| 16951 | NNNNNNNNNN | NNNNNNNNNN | NNNNNNNNNN | NNNNNNNNNN | NNNNNNNNNN |
| 17001 | NNNNNNNNNN | NNNNNNNNNN | NNNNNNNNNN | NNNNNNNNNN | NNNNNNNNNN |
| 17051 | NNNNNNNNNN | NNNNNNNNNN | NNNNNNNNNN | NNNNNNNNNN | NNNNNNNNNN |
| 17101 | NNNNNNNNNN | NNNNNNNNNN | NNNNNNNNNN | NNNNNNNNNN | NNNNNNNNNN |
| 17151 | NNNNNNNNNN | NNNNNNNNNN | NNNNNNNNNN | NNNNNNNNNN | NNNNNNNNNN |
| 17201 | NNNNNNNNNN | NNNNNNNNNN | NNNNNNNNNN | NNNNNNNNNN | NNNNNNNNNN |
| 17251 | NNNNNNNNNN | NNNNNNNNNN | NNNNNNNNNN | NNNNNNNNNN | NNNNNNNNNN |
| 17301 | NNNNNNNNNN | NNNNNNNNNN | NNNNNNNNNN | NNNNNNNNNN | NNNNNNNNNN |
| 17351 | NNNNNNNNNN | NNNNNNNNNN | NNNNNNNNNN | NNNNNNNNNN | NNNNNNNNNN |
| 17401 | NNNNNNNNNN | NNNNNNNNNN | NNNNNNNNNN | NNNNNNNNNN | NNNNNNNNNN |
| 17451 | NNNNNNNNNN | NNNNNNNNNN | NNNNNNNNNN | NNNNNNNNNN | NNNNNNNNNN |
| 17501 | NNNNNNNNNN | NNNNNNNNNN | NNNNNNNNNN | NNNNNNNNNN | NNNNNNNNNN |
| 17551 | NNNNNNNNNN | NNNNNNNNNN | NNNNNNNNNN | NNNNNNNNNN | NNNNNNNNNN |
| 17601 | NNNNNNNNNN | NNNNNNNNNN | NNNNNNNNNN | NNNNNNNNNN | NNNNNNNNNN |
| 17651 | NNNNNNNNNN | NNNNNNNNNN | NNNNNNNNNN | NNNNNNNNNN | NNNNNNNNNN |
| 17701 | NNNNNNNNNN | NNNNNNNNNN | NNNNNNNNNN | NNNNNNNNNN | NNNNNNNNNN |
| 17751 | NNNNNNNNNN | NNNNNNNNNN | NNNNNNNNNN | NNNNNNNNNN | NNNNNNNNNN |
| 17801 | NNNNNNNNNN | NNNNNNNNNN | NNNNNNNNNN | NNNNNNNNNN | NNNNNNNNNN |
| 17851 | NNNNNNNNNN | NNNNNNNNNN | NNNNNNNNNN | NNNNNNNNNN | NNNNNNNNNN |
| 17901 | NNNNNNNNNN | NNNNNNNNNN | NNNNNNNNNN | NNNNNNNNNN | NNNNNNNNNN |
| 17951 | NNNNNNNNNN | NNNNNNNNNN | NNNNNNNNNN | NNNNNNNNNN | NNNNNNNNNN |
| 18001 | NNNNNNNNNN | NNNNNNNNNN | NNNNNNNNNN | NNNNNNNNNN | NNNNNNNNNN |
| 18051 | NNNNNNNNNN | NNNNNNNNNN | NNNNNNNNNN | NNNNNNNNNN | NNNNNNNNNN |
| 18101 | NNNNNNNNNN | NNNNNNNNNN | NNNNNNNNNN | NNNNNNNNNN | NNNNNNNNNN |
| 18151 | NNNNNNNNNN | NNNNNNNNNN | NNNNNNNNNN | NNNNNNNNNN | NNNNNNNNNN |
| 18201 | NNNNNNNNNN | NNNNNNNNNN | NNNNNNNNNN | NNNNNNNNNN | NNNNNNNNNN |
| 18251 | NNNNNNNNNN | NNNNNNNNNN | NNNNNNNNNN | NNNNNNNNNN | NNNNNNNNNN |
| 18301 | NNNNNNNNNN | NNNNNNNNNN | NNNNNNNNNN | NNNNNNNNNN | NNNNNNNNNN |
| 18351 | NNNNNNNNNN | NNNNNNNNNN | NNNNNNNNNN | NNNNNNNNNN | NNNNNNNNNN |
| 18401 | NNNNNNNNNN | NNNNNNNNNN | NNNNNNNNNN | NNNNNNNNNN | NNNNNNNNNN |
| 18451 | NNNNNNNNNN | NNNNNNNNNN | NNNNNNNNNN | NNNNNNNNNN | NNNNNNNNNN |
| 18501 | NNNNNNNNNN | NNNNNNNNNN | NNNNNNNNNN | NNNNNNNNNN | NNNNNNNNNN |
| 18551 | NNNNNNNNNN | NNNNNNNNNN | NNNNNNNNNN | NNNNNNNNNN | NNNNNNNNNN |
| 18601 | NNNNNNNNNN | NNNNNNNNNN | NNNNNNNNNN | NNNNNNNNNN | NNNNNNNNNN |
| 18651 | NNNNNNNNNN | NNNNNNNNNN | NNNNNNNNNN | NNNNNNNNNN | NNNNNNNNNN |
| 18701 | NNNNNNNNNN | NNNNNNNNNN | NNNNNNNNNN | NNNNNNNNNN | NNNNNNNNNN |
| 18751 | NNNNNNNNNN | NNNNNNNNNN | NNNNNNNNNN | NNNNNNNNNN | NNNNNNNNNN |
| 18801 | NNNNNNNNNN | NNNNNNNNNN | NNNNNNNNNN | NNNNNNNNNN | NNNNNNNNNN |
| 18851 | NNNNNNNNNN | NNNNNNNNNN | NNNNNNNNNN | NNNNNNNNNN | NNNNNNNNNN |

FIGURE 3G

```
18901 NNNNNNNNNN NNNNNNNNNN NNNNNNNNNN NNNNNNNNNN NNNNNNNNNN
18951 NNNNNNNNNN NNNNNNNNNN NNNNNNNNNN NNNNNNNNNN NNNNNNNNNN
19001 NNNNNNNNNN NNNNNNNNNN NNNNNNNNNN NNNNNNNNNN NNNNNNNNNN
19051 NNNNNNNNNN NNNNNNNNNN NNNNNNNNNN NNNNNNNNNN NNNNNNNNNN
19101 NNNNNNNNNN NNNNNNNNNN NNNNNNNNNN NNNNNNNNNN NNNNNNNNNN
19151 NNNNNNNNNN NNNNNNNNNN NNNNNNNNNN NNNNNNNNNN NNNNNNNNNN
19201 NNNNNNNNNN NNNNNNNNNN NNNNNNNNNN NNNNNNNNNN NNNNNNNNNN
19251 NNNNNNNNNN NNNNNNNNNN NNNNNNNNNN NNNNNNNNNN NNNNNNNNNN
19301 NNNNNNNNNN NNNNNNNNNN NNNNNNNNNN NNNNNNNNNN NNNNNNNNNN
19351 NNNNNNNNNN NNNNNNNNNN NNNNNNNNNN NNNNNNNNNN NNNNNNNNNN
19401 NNNNNNNNNN NNNNNNNNNN NNNNNNNNNN NNNNNNNNNN NNNNNNNNNN
19451 NNNNNNNNNN NNNNNNNNNN NNNNNNNNNN NNNNNNNNNN NNNNNNNNNN
19501 NNNNNNNNNN NNNNNNNNNN NNNNNNNNNN NNNNNNNNNN NNNNNNNNNN
19551 NNNNNNNNNN NNNNNNNNNN NNNNNNNNNN NNNNNNNNNN NNNNNNNNNN
19601 NNNNNNNNNN NNNNNNNNNN NNNNNNNNNN NNNNNNNNNN NNNNNNNNNN
19651 NNNNNNNNNN NNNNNNNNNN NNNNNNNNNN NNNNNNNNNN NNNNNNNNNN
19701 NNNNNNNNNN NNNNNNNNNN NNNNNNNNNN NNNNNNNNNN NNNNNNNNNN
19751 NNNNNNNNNN NNNNNNNNNN NNNNNNNNNN NNNNNNNNNN NNNNNNNNNN
19801 NNNNNNNNNN NNNNNNNNNN NNNNNNNNNN NNNNNNNNNN NNNNNNNNNN
19851 NNNNNNNNNN NNNNNNNNNN NNNNNNNNNN NNNNNNNNNN NNNNNNNNNN
19901 NNNNNNNNNN NNNNNNNNNN NNNNNNNNNN NNNNNNNNNN NNNNNNNNNN
19951 NNNNNNNNNN NNNNNNNNNN NNNNNNNNNN NNNNNNNNNN NNNNNNNNNN
20001 NNNNNNNNNN NNNNNNNNNN NNNNNNNNNN NNNNNNNNNN NNNNNNNNNN
20051 NNNNNNNNNN NNNNNNNNNN NNNNNNNNNN NNNNNNNNNN NNNNNNNNNN
20101 NNNNNNNNNN NNNNNNNNNN NNNNNNNNNN NNNNNNNNNN NNNNNNNNNN
20151 NNNNNNNNNN NNNNNNNNNN NNNNNNNNNN NNNNNNNNNN NNNNNNNNNN
20201 NNNNNNNNNN NNNNNNNNNN NNNNNNNNNN NNNNNNNNNN NNNNNNNNNN
20251 NNNNNNNNNN NNNNNNNNNN NNNNNNNNNN NNNNNNNNNN NNNNNNNNNN
20301 NNNNNNNNNN NNNNNNNNNN NNNNNNNNNN NNNNNNNNNN NNNNNNNNNN
20351 NNNNNNNNNN NNNNNNNNNN NNNNNNNNNN NNNNNNNNNN NNNNNNNNNN
20401 NNNNNNNNNN NNNNNNNNNN NNNNNNNNNN NNNNNNNNNN NNNNNNNNNN
20451 NNNNNNNNNN NNNNNNNNNN NNNNNNNNNN NNNNNNNNNN NNNNNNNNNN
20501 NNNNNNNNNN NNNNNNNNNN NNNNNNNNNN NNNNNNNNNN NNNNNNNNNN
20551 NNNNNNNNNN NNNNNNNNNN NNNNNNNNNN NNNNNNNNNN NNNNNNNNNN
20601 NNNNNNNNNN NNNNNNNNNN NNNNNNNNNN NNNNNNNNNN NNNNNNNNNN
20651 NNNNNNNNNN NNNNNNNNNN NNNNNNNNNN NNNNNNNNNN NNNNNNNNNN
20701 NNNNNNNNNN NNNNNNNNNN NNNNNNNNNN NNNNNNNNNN NNNNNNNNNN
20751 NNNNNNNNNN NNNNNNNNNN NNNNNNNNNN NNNNNNNNNN NNNNNNNNNN
20801 NNNNNNNNNN NNNNNNNNNN NNNNNNNNNN NNNNNNNNNN NNNNNNNNNN
20851 NNNNNNNNNN NNNNNNNNNN NNNNNNNNNN NNNNNNNNNN NNNNNNNNNN
20901 NNNNNNNNNN NNNNNNNNNN NNNNNNNNNN NNNNNNNNNN NNNNNNNNNN
20951 NNNNNNNNNN NNNNNNNNNN NNNNNNNNNN NNNNNNNNNN NNNNNNNNNN
21001 NNNNNNNNNN NNNNNNNNNN NNNNNNNNNN NNNNNNNNNN NNNNNNNNNN
21051 NNNNNNNNNN NNNNNNNNNN NNNNNNNNNN NCTGTGGGGG GCTCCACCCA
21101 GTTTGAGCTT CCCAGCTGCT TTGTTTACCT ACTCAAGCCT CAGCAATGGC
21151 GGATGTCCCT CCACCAGCCT CATTGCCACC TTGCAGTTCA ATCTCAGACT
21201 GCTGTGCTAG CAGTGAGTGA GGCTCCATGG GCGTGGGACC CTCTGAGCCA
21251 GGTGCGGGAT ATGATCTCCT GGTGTGCCAT TTGCTAGGAC TGTTGGAAGA
21301 GCACAGTATT AGGGTGGGAG TGTCCCGATT TTCCAGGTAC CTTCTGTCAT
21351 CACTTCCCTT GGCTAAGAAA GGGGATTCCC TGACCCCTTG CACTTCCTGG
21401 GTGAGGCGAT GCCCTGCCCT AGTTCAGCTC ACACTTCGTG GGCTGCACCC
21451 ACTGTCCAAC AAGCCCCAGT GCGATGAACG CGGTACCTCA GTTGGAAATG
21501 CAGAAATCAC CTGTCTTCTG CGTTGCTCAT GCTGGGAGCT GTAGACTGGA
21551 GCTGTTCCTA TTTGGCCATC TTTGAACCTC CCCCCTGACT TGCGTATGTT
```

FIGURE 3H

```
21601 AAATCTTCCC TCTATCTCTG GGACAAAGCC CATTTGATCA TGATGTATTA
21651 TGTTTTTGAT TTGCTATTGG ATTCTGTTTG CTGGTATTTT GTTGAGGACT
21701 TTTGCATCTA TGTTCATCAG GAATATTGAT CTGTAGTTTT CTTTTTTGTT
21751 ATGTCATTTC CTGGGTTTGA CACAGGGTGA TACTGGCTTC ATAGAATGAG
21801 TTTGGGAGGA TTTTCTCTTT CTCAATCTTT TTGAATAATC TCAATAGTAT
21851 TGCTTCCAAT TCTTCTTTGA CTGTCTGGTA GAATTCAGCT ATGAATCCAT
21901 CTGGCCCTAG GCTTTTTTGT TGCTGGCAAT TTCAATCAGT AAATTTTACT
21951 TAGTCAGTCT CACTGCTTGT TATCTGGTCT GCTCAGGATT TCTATTTCTT
22001 CCTGATTTAA TCTGGGATGG TTGTAAATTT CCAGGAATTT ATCCATTTCT
22051 TCTATGTTTT TTAGTTTGTG TGAATAGAGA TGTTCATAGT AATCTCAACT
22101 GATCTTTTGT ATTTCTGTTT CATTGGTTGT AGTGTCTCTA TTTTCATTTC
22151 TAATTGAACT TATTCAAAAC TTCTCTCCTC TTAGTTAATC TAGTTAATGG
22201 TCTATCAATT TTGTTTATCT TTTCAAAGAA CCAACTTTTT GTTTTACTAA
22251 CCTTGTGTAA TATTTTTGTT TCAATTTCAT TTATTTCTGC TCTGGTCTTT
22301 GTTGTTTCTT TTCTTCTCTA GCTTTGGGTT CCTTTGTTCC TGTTTCTTTA
22351 GCTCCTTGAG GTGCGATGTT AGGGTGTCAA GTTGTGATCT TTCAGACTTT
22401 TTGATGTAGG CATTTAGTGC TATAAACTTT CCTCTTAGCA CCACTTTTGC
22451 TGTATCTCAG AAGTTTTGAC AACTGTGTCA TATTATCATT CATTTCAAGT
22501 AATTTTTAAA TGTTCATCTT TATTTCATTG TTAACCCAAA ATTTATACAG
22551 GAGCAGATTT TTTAATTTCC ATGTATTTGT ATAGTTTTGA GAATTCCTTT
22601 TGGAGTTGGT TTCTAGTTTT TTCCTACTGT GGTCTGAGAA GATGCTTGAT
22651 ATGATTTTGA TTTTTAAAAA TTATTGATAC TTGTTTTGTA GCCAATCGTA
22701 TGGCCTATGT TGGAATATAT TCCATGTGCT GATGAGAAGA AAGTATATTC
22751 TATAGTTTTT GGGTAGGATG TTCTGTAAAT ATCTGTTAGG TCTACTTGTT
22801 TTAGAGTATT GTTAAGTCA TTGTTTCTTT GTTGACTTTC TGCCTCGATG
22851 ATCTGTCTAG TGCTGTCAGT GGGGTGTTGA AGTATCCCAC TATTATTGGG
22901 TTGCTCATTA TCTCTTTCCT TAGGTCTAGC AGTAATTGTT TTATGAATTT
22951 TGGAGCTCCA TAGTTAGGTA CACATATATT TTGGATTATA ATATTCTCTT
23001 GTCAGATTAA TCCTTTTATC ATTATATAAT TGTAACCACC TAACAGGTTA
23051 TTTCTGCCCA CTGCACAAGC AAAATCAATT CATGGCATTG TGGTGAAGAA
23101 AGTGTTTAAT TGATGCAAGG CCAGTCATGC CATGTGGTCA AACTAGGATG
23151 GAGATATTAC TCAAATCAAT CTCATCAAAG GCTTGTTGGT TAGGGGTTTT
23201 TCAAAGGCAG TTTTGGGGAA GGGATTGGGC TGACCAGACC AGGTGCTTGC
23251 TGCTGATTGT TTGGGTTGGA GATGAAATCA TATGGAGTTG AAGCTGTCCT
23301 CTTGTGCTGA GTCACTTCTG TGGGGCCACA GGAGTGGTTG GTGGGTCCAT
23351 ATGGGTCCAA GTGAAGCCAT CGGTGTCAGA CATGCAAAAA ACCTGAAAAG
23401 ATATCTCAAA AGGCTAATCT TAGGTTCTAC AATAGTGATG TTATCTGCAT
23451 GAGTAATTGG GGGAGTTGCA TATCTGTGAC CTCTGGAATA ATGGCTGTCA
23501 ATCATTTATA TCCACACCTT AGCAGAATTC AGGCTCTTCT CCTCCTCCTA
23551 AGTCTGGTGG TTTCTCATTA GCTTTACAAA GGTGACTGAG TTTTGGGAAA
23601 GATTATTATC ATTTAAACTA CAAACTAAAT GTCTCCCAAA GCTAGCCAAG
23651 ACTAAGCCCA GGAATAATTA AGGCAGCTTG AAGGCTAAAG GCAAGAGGGA
23701 GGTTGGCTAG ATCAGATGTC CCCCACTGCC ATAATTGTCT CAGTGATATA
23751 ATTTTTGCAA AGGTGGTTTT ATAATGACCT TCTTTGTCTT TTTCTTTTTT
23801 TTAACTGTTG TTGCTTTAAA GTCTGTTTTA TTTAATATAA GAATAGCCAC
23851 TCCTACCCAG GCACGGTGGC TCACACCTGT AAATCCCAGC ACTTTGGGAG
23901 GCTGAGGCAG GTATATCACC TGAGGTCAGG AGTTCAAGAC CAGCCAGACA
23951 GAGATGGTGA AACTCCATCT CTACTAAATT TACAAAAACA TTAGCCAGGC
24001 ATGGTGGGGG GCACCTGTAA TCCCAGCTAC TCAGGAGGCT GAGGCAGGAG
24051 AATTGCTTGT ACCCGGGAGG CAGAGGTTGC AGTGAGCCAA GATTGCGCCT
24101 TGCTCTCCAG CCTGGGCAAC AAAGTGAGAC TTCATCTCAA AAAAAAAAAA
24151 AAAAAAAAAA AAGAATAGCT ACTCCTGCTA GCCTTTGGTT TCCATATACA
24201 CAGAACATCT TTTCCCACCC CTTTACCTTG TGCTTGTGTG AATCCTTATG
24251 CATTAGATGA GTCTCTTGAA GACAGCAGAT ATTTGGTTTG TGATATTTTA
```

FIGURE 3I

```
24301 TCCATTCTGC CAATCTGTAT GTTTTCAGTG GAGCATTTAT GCCATTTATG
24351 TTTAATATTA ACATTGAGAT GTAAGGTACG ATTCTCCTCA TCATGTTGAT
24401 TATTACCTGG ATCCTTTTGT GTGTGTGTGT GTGTGTTATT GTTTTTATTT
24451 TTTTATTTTA ATTTTTTTGA GACAGAGTCT TGCTCTGTCA CCCAGGCTGG
24501 AGTGCAGTGG CGAGATCTCT GCTCACTGCA AGCTCCGCCT CCTGGGTTCA
24551 TGCCATTCTC CTGCCTCAGC CTCCCGAGTA GCTGGGACTA CAGACACCCG
24601 CCACTACGCC TGGCTAATTT TTTGTATTTT TAGTAGAGAC GGGGTTTCAC
24651 CATGTTAGCC AGGATGGTCT CGATCTCCTG ACCTCGTGAT CCACCCCCCT
24701 TGGCCTCCCA AAGTGCTGGG ATTACAGGTG TGAGCCACCG TGCCCGGCCA
24751 TGTGTGTGTG TTATTGTTTT ATAGGCCCTG TGAGTTTTAT GCTTTCAAGA
24801 GGTTTTATTC TGATGCATGT CAACTTTTGG TTTCAAGATT TAGAAGTCCT
24851 TTTAGAATTT TGTGTATGGC TGGTCTGGTA GTTACAAATT CCTTCATCAT
24901 TTGCTTGTCT GGAAAAGACT TTATTTCTCT TTCATTTATG AAACTTAGTT
24951 TTGCTGGACA CAAAATTCTT GACTGACACT TATTCTGTTT AAGGAGGCTA
25001 AAGATTGGAC CCCAATCCCT TCTGGCTTGT AAGGTTTCTG CTGAGGGAA
25051 GATTTTTATC AATGACATAA ATGTGTGATG ATGGAAACAA TCCAGTGGGA
25101 AGAGAAAATT GATGCAGGAG AGAAGAAAGA AAGCTTTTTT GGAGGGCTGC
25151 TCTTTAGTAT ATGAGAGTAG ATGGAATCTA TTCAACATGT AAAGGAGTCT
25201 TAGCTAGGCC TTAGATAGGA GTAGGAATTG TTTATCCAAA GTAAAATGAA
25251 GGAAGAGAGA TTCCAGTAGG TTGGAAGACA TGGTGGGAAG GACTTGAGGA
25301 AATTCTCCTC TATTGCTTAT TTTACTCAAT AAAGTAGGAA GCAAGGTTAC
25351 CAGCTGTGAA TGAGGAGTGG AAGAAGGCAT TAGAGACTTG ATGAGAGAAA
25401 AGAAGCCATG AAAGAGTTAT ACAAAAGTGT ATGAGGTTTA TTGGACTAGG
25451 GAAAGTATGT CTGCCAGGCG CTTTAAAGGG CCAACTGAAG TTAGTGACCA
25501 GAAATTCAAA GTGAGACAAG CCATTATGTC CAACAGCATG GGTGCAGGCA
25551 GAGAGTAGTG GGAAGCTGGA TTTAACCAGA GTCATGGTTT AGCAAAGTGA
25601 ACTCAACAAC CTGGGAGAGA GACAGGGGAA CTTAGGGAGT GCCCGAAGGC
25651 ATGATAACAT TAATAGAGAT CCTCCTCCAG TGAATGTCAC CAGCCTCCCA
25701 GTTGCTCAAC TGAGAAACCT TGACCTTTTC CTCAACCCCT AACACCCAAA
25751 CACCAAGTGG TATTGATTTC ACTTCCTAAA TATCTCCTCC TTTCCTCATT
25801 GGATTAAGCT ACTGTAATTT GTCTTCATGT TTATATCATT TCCCCATAG
25851 CAGCCAGAGG TGATGTTTTA GAAATTACAA GCCTGATCAT GTAACTACCT
25901 ACTTACAAGC TTCCAGCAGC TTCTTTTTTT TTTTCAAGTG GCAGTTTTAA
25951 GTTTGTGGGT TTTTAATTTA TATATGTGAA ATACCTTTTT ATAGGCAAAA
26001 ATAATAATAG CATGCTTCTT ACTGCCCTTA ATGTGAAATG ACTCACAAGA
26051 CCTTGGTGTG GCCAACTCTC CAGCCTCTTT TTTGGCTTAT ATTTTTCCTT
26101 CTTCCCCATA TGCCAGCCCT ACTTTCTTCT TCAATTCTT CAAAGTCAGT
26151 CATCTCTGAG GGTGCATATA CCCCCAGAGA ATGCCCAAGA TGATTCACTG
26201 GGATGAGGAA AAAAAATACT AGAACTTCCT TTTATATTTA TTTGTGATTA
26251 TATATTTTTA ATTTCTGTGA TTATATGTAT TGAAAATGTG TAAATCAGTA
26301 GTACATGGAT ACACTTTATA AATACATATA CATATATTAG AGTAGTGCTC
26351 AAATATATTT TTTATTATGC ACATGCAGTT GTAAGAATAT GTACAGAGAC
26401 CACATGTACC ATTTACCCAG TTTCACACAA ACTTGCATCT TGCAAAACTA
26451 TAGTCATAAC CTTGATATTA ATATTGATCT AATTCACTGA TCTTATTAAG
26501 ATTTTCCCAG TTCTTGTATT CATGCATGTG TATGTATTTT AACTCTATGG
26551 AATGTTATCA CATAAATAGG TTGTTATATT CCCCACCACA GTAAAGATAC
26601 AGGACAAGTC CATTATCACA AGGGCCCTTC AAGTGGCTCT TCTGTAGCCA
26651 CCTCCTAACC CCCTATACCC TGTCCCTGAC TCCTGCCAGC CACTAATCCG
26701 TTCTCCATTT CTATAATTTT GTCATTCCAA GAAAATTATA TACAAGAAAT
26751 CATACAGTAG TAACCTTTTA GGATTGGCAT TTTTCACTCA CCATACTTCT
26801 CGGGCAATTC ATCTAAACTG TTGTATCAAT AGTTGGTTCA TTTTTATTGC
26851 TGAGTGGTAT TCCACGTATG TAGGTACCAC AATTTGTTTA ACCATTCACC
26901 AGCTGAGGAC ATGTAGATTC TTTGCAGTTA GGAGCTATTA TCAATAAAGC
26951 AACTAATGAT GTTGAATATT AAAAAAATGC TTTATTGACA AAGGAAGCCA
```

FIGURE 3J

```
27001 ATCAAAAAAG CTTGTAGACC ATAACCCTAA TGTTTCAGGT CTTTCCTACC
27051 TCAAGATCTT CTGTCCTACC CATCCCTACT TTTAGAACCT CTCCCTACTT
27101 TTCTCTAGCT AACTCTTGGA CTCCAGAGAA AGTGTTAAAA GTCTTCCCTA
27151 ACCCCCAGAC CAGGAGTACA TCCCCCTGTT TTATGCTCCT AATGCTCCTG
27201 GCACTTTTCC CCCTAAGCCC ACTGTACCTG ATATTTTCTA TCTGCCCCTC
27251 CAGATCTACT CTCCACCCTT CTTCATTCTG CTCTCAGCCC AGGACTACAT
27301 CAAATCTCCT TAGTCCTCTG GGTTCCAGTT GACTTTGATC TCTAGGGAGC
27351 CCTTGCAGGG GAAGGAAGGA GAAGGAGGGC CTGATTTTAT TCCCCCAGCC
27401 CCTCACGGTA AGGCTGACTC AGGCAACTTT TGTGTCTAGA AGGAAAGCCT
27451 CAGCTTCTCT CTACACAAAA CTATCTTCCT AGGTTTTAAT ATCTGCTCCC
27501 TTCCCTTTGT CCCCTTGGTC CTGTAGACGT ATTTTGCTTG GTCTAATCCT
27551 AGGTTTTAAA ATTTGAATTA GTTGTTGATA CTTAATAATT GGAAGATTTT
27601 GCATAAAGTT TCAGATGTCT GGCTTCTCTT GAAAAAAAAT CAGAAGGTTT
27651 GACAACACTG AGCCTCCATT CCAAATAGTA GCCATTGTGT GGCCTTGAGT
27701 AGAGCCACCC CTTCCACTGG GGCAGCTACT CTTAAGGATT CACCATCCCC
27751 ACTAACTCCC TGTTCCATAC AATAACCTTG CTTTGCTATT ACCACCCTGG
27801 CACTAGGAGT CCTGGTTTAA AGAATGTGTT GCCCGCTAGG TGGGACCTGT
27851 GTCAGACTTC TCATCAGATT TGGAGAAAGG GCATGCTGGC CTCTCCCATC
27901 TGTCTACTTC TCTCTGTCTC CCCTTGCACC ACATAGAGCA CCCTTTCTCT
27951 GGGGTTTCTA TCATCCCCTC CTAGACTCCC ACTTGCTCCC AGGCTTGCTG
28001 CTCCTCTCTG CACTTCTCAC ATCTTGCCAG AGTGCTTTTT TTTTTTTCTT
28051 TTTTTTGAGG TGGAGTCTCA CTCTGTCACC TAGGCTGGAG TGCAGTGGTG
28101 TGATCTTGGC TCACTGCAAC CTCTGCCCCC TGGGTTCAAG CAATTCTCCT
28151 GTCTCAGCCT CCCAAGTAGC CAGAATTACA GGCGGCTGCC ACCATGCCTG
28201 GCTAATTTTT TGTATTTATA GTAGAGACGG GGTTTCACTT TCACCATCTT
28251 GACCAGGCTG GTCTTGAACT CTTGACCTTG TGATCCACCC GCCTCGGCCT
28301 CCCAAAGTGC TGGGATTACA GGTGTGAGGC ATCACACCCG GCCCAGAGTG
28351 CTCTTTTTAA ATGGGACTCA GATTACAACC CTTTTTCTTA AAACCTTGCT
28401 ATGTTTTCTC ATTGCCCTAT AGTTAAAGCC TGCATTTCTA AAGCAGTCCC
28451 CTGGCTTATC TGACCTTTTC CTACTACCAG GCTGATCTGG GGCCACCCCT
28501 CCTCATTCTG CTTTTCCAGA ACAGTGGGTT CCTCAAGCAC ACACCTTATG
28551 TCTTGCCTGG GCAGCACACT TGCCAAGCTC CTAGGCCAAG TATGAGGCCT
28601 CTCTCCTCAC TTCCTGGTCA CAATTTAAGT GCCCTTACCC AGATAGTGCC
28651 TTTCCATTCT CTGTCTGTAT CTCTTCTTAA TAGGTGCTAT GCTTGTAAGA
28701 AGGGATTTTT TTTTTAGTCT TTCTCTCATT GGACTGTGAG AATAGTGTTT
28751 ATCTTTTTCA CTGCCTGGTG TATAGTAGGT GCTCATTGAA CATTTATTGA
28801 AAGAGCAGAT TTAGAGATCT AGCTCTTCAT GGAATAGCAG TTTCTACCAC
28851 CTAGCGACAA TGTGGAATAC CAGGGCTTCT AAAGTGTTTA GTATGATCAT
28901 ACATTTATAT TATGAGGCCT GCCTGTGGGG TGATTGCACA TGAGGTGAGG
28951 CCATTGAGGC ACCTAGGGCA GAGGATTTAA GGAAGCTTTC ACCCTTACAA
29001 TGCCTCTCCT GCCACACTCT AGACCTGGCT CTGGGAGGGA AGCCTTTGCT
29051 AAGAACCATG AAAGGAAAGG AGAAAAAGAA AACTAGGGTG GTGCTAAAGG
29101 GACATTTGTG ATGGCAGCCT GACACCTACC ACCTGATTCT TGAACACTCA
29151 CTGTGGATAG AATGGTGTAT GATGGCCACA GGGCAGGAGG GGGCAGCAGA
29201 GTGATGATAC CTTAACTGAC ACCTGAGTCA GTAATGGGAG AACTGAGGAG
29251 AAGCAGTGGG TTCTTCTACA GGAAATCGAA GGGTGGAATT CATTAATCTA
29301 GCCCTTAAAA CAACAGCTTA CCCAACATGC TACACAAAAC CAGGTTTCTG
29351 TTTCAGATAA ATAGGTGAAG GGACTCTTAA TCCTAAAGAC TGAAAAGTAG
29401 AAAAGAAAGG GGAAGAAGAG TGCCTCAAGG ATTGCCATTG GAGGTTCTTT
29451 TGCTGGGGCT GATTGCCAGC TGAGATTATT CAAGCCCCAG AGCAAACATT
29501 CTGCTCCTGC TCCCTTAGAG CTGCCCTCCC ACCGCTCAGT ATTGCCTCCT
29551 GCGAGGGGCG GGCTGGCTGC CGCAGACACC AGTGAACCCT TTTTCCATTC
29601 CAGAAGTCCC AGTGGACCTA CTTTAATATA CCAATAACAC TCCTATTTTA
29651 AACTAGCTGT ATCCATTTTC GTTTTAATAG TCCCAGTGCT AAAGTTTTTC
```

FIGURE 3K

```
29701 AAAGCAGTTA TTTTGTAAGT AGGTCAAACA GGTACTTTGG GATCCTGTTC
29751 TGTCTGTTTG CTTGCCAGGT AACCTCTTTG TTATCTAATT CAAAGTCTGG
29801 TACAGTTTGA ACCAAAACAA AAAAGGAATG ATGTTTCACT TTGGAGTCAA
29851 GATTCATTCA TTTTCTAACA TTAATCATTT TCGTAATACA GTAAGTCTAT
29901 ATTCATGATA AAAAATAGAA AATATGAATA AGCAAAACTA AATTGAAAGG
29951 AAAACCATCT GTGATCTGCC AATTAGAAAA TCTCTATTCT AAACATTTTG
30001 GTAAATATGC TACCAGATTT TTATCTATGC AAATGTGTAT CTGTATTTTT
30051 CCTCACTTGT ATAGTGGACA TCTTTTCATA TTAATAAATA AGTTAGCATC
30101 ATTACTTTTG ATAGCTTCAT GGTGTGAAAT TATAAAATTA GACCTACCAC
30151 ACTCTATTTT AACTATCTCT CTTGCTGGGT ACTTAAGCTA TTCCCAATAT
30201 CACAGAAGCC TTTTTACACA TGCATCCTTG TACATGCATC AGATTCTTTA
30251 AGATTGCCAA AGGTGAAATG GTTGGGTCCC AGGGTGCAAC TATTTTTTAG
30301 CATTTCAATA CATAATACCA AAGTGCAATC CAGAACCATT GTACCAATTA
30351 ATGCTCCCGC CAGCAGCACA TTGCAGTGTT GATTTCCTCC TGGCCTCACC
30401 AGCACGCTGT CAACACTGGG TACTGGTGTG TCGTGTACAT GACATTACAT
30451 GCCAGGCACT GAGAGTGAAA TAAAACAGTT CATGTTGGGA ATGGGGCAAG
30501 AGAGGGAGAT AAACAAGGGA GGTGACATCT ACAGACCGGT TAGCTGAGAT
30551 TACAGTACAT TGGGGCTCCA AGTGCACAGA ATCTGAACAT CATGTTCATC
30601 CTAGGACAAG TGTTGCAGAG GCTTCCTGAA GAGGTTCATT CTGAGGCTTA
30651 CCTTGAAGGA TCATCAGGAA TTAATGATGA GTGTATTAAG CCATTCTCGC
30701 ATTTCTATAA AGAAACGCCT GAAATTGAGT AATTTTTTTT TTTTTTTTTT
30751 TTTCTGAGAC GGAGTCTTGC TTTCTTACCT AGGCTGGAGA GCAGTGGTGC
30801 GATCTCGGCT CACTGCAACC TCTGCCTCCC TGGGTTCAAG TGATTCTCCT
30851 GCCTCAGCCA CCCGAGTAGC ACAGGTGCCT GCCACCGGGT CCATCTAATT
30901 TTTGTATTTT TAGTAGAGAC AGGGTTTCAC CATGTTGGCC AGGCTGGTCT
30951 CAAACTCCCA ACCTCGTGAT CCTCCCGCCT TGGCCTCCCG AAGTGCTGGG
31001 ATTACAGGCG TGAGCTGCCG CGCCCAGCCA AAATTGAGTA ATTTATAAGA
31051 AAAAAAGGTT TTATTAGCTC ATGATTCTGC AGGCTGTACA GGAAGCGTGG
31101 TGGCATCTGC TTCTGTAGAG GCCTCAGGAA GCTCCAATCA TGGTGGAAGG
31151 TGGAAGGCAC ATCACACTGT GAAAGCAGGA GCAAGAGTTG GGGGAACATG
31201 CCATAAGATC CCATCACTTT TAAAGAACCA GATCTCATGT GAACTCAGAG
31251 CGAGAGCTCA CTTATCACTA AGGAGATGGC CCAAGCCATT CATGAGACAT
31301 CAGCCTCCAT GACCCAAACA CGTCCCACCA GACTCCACCT CCAACATTGG
31351 GGATTACATT TCAATGAGAT TTGGGTGGGG ACAAATGTCC AAACTATATT
31401 GATGAGTGAA AGCAAGAGTA AGAACAGGG AAGGAATGAT GGAGAGAATG
31451 AACCAGGTAG AGAAAATCTT CTAGGCATGA ATGTTCAGCC CCTTTTCAGG
31501 GAGCAACAAA AAGTTCTGTA TTGGTTGCAA TGAAGGGTGC ATGGGGCATT
31551 GGGGATGGTG GACAGGAATG ATGGACAGTG AGGCTGATGA GATGAGCTGG
31601 GTCTCATCAA GAAGTTCTCT CCGGGCTTAG CAAAGGAGCT CTAGCTTTAT
31651 CTGGAAACTT TCCTTGGGAG GCAGGACTTG GCATCAAAAC CTGTGTGTGG
31701 AAGACTCACA CCGATCCAAG GGAAGGGCAC TGATGCTGGG CTTAAGCATT
31751 GCTTTGTCAT TCCCTGATGA GCTCTCTCAG CTTGGGAACA GCCACTCTCT
31801 GTCTAGTAAA GGAAAGGAGC TGATCCAGGT CCTCTCCAGT TCTAACTATG
31851 CTCCTGTGAA TTCTGGCACA ATTTTTACTT TTTTTCCTTG CAGAAAAGGT
31901 GGCCATTAAG ATCCTGGACA AGACCAAGTT AGACCAGAAA ACCCAGAGGC
31951 TACTATCCCG AGAAATCTCC AGCATGGAAA AGCTGCACCA TCCCAACATC
32001 ATCCGCCTTT ACGAAGTGGT GGAGACCCTA TCCAAGCTGC ACTTGGTGAT
32051 GGAGTATGCA GGGGGTGGGG AGCTCTTCGG AAAAATTAGC ACTGAGGGGA
32101 AGCTCTCTGA ACCAGAAAGC AAGCTCATCT TCTCCCAGAT TGTGTCTGCC
32151 GTGAAGCACA TGGTGAGCAG GGGTGACGAG TGAGAACCTT GCTCCCATTG
32201 CACTGACACT GGGAGCACAG GGCTTTAGGT TACTAACCCT CAAGTGTCCC
32251 AGAGGGCTTT TGTCCTACAA AGCAGACAGT AGTCCCTTCT GAGAGTCAGA
32301 AGTCTGGCTG GGATCATGCT CCTTGCCTGT GAAGCAACAT CCAGGGATGT
32351 CCAGTTACAC GTCAACCTCC TAGCTTCTGC AGACATTGGC AGGAATCACT
```

FIGURE 3L

```
32401 GGGAGCAGCT GATGAATATC ACCCACTCCC TGGCCATACC CATTTCTCCA
32451 ACCTCATCTT CCACTATCTG GATAGCTGGC TCCTCACTGC TTCTTGGTTT
32501 TGCTTTCCTA CTTCTGTCTA GGATGCCCTC ATATGACATC TCACATTCTA
32551 AATCCTATCC ATACTTCATG CCCAGCTTGG TTCTCTCTCT CTCTCTCTCC
32601 CCCACCCCCC CTCTCCGTGT GTGTGTGTGT GTGTGTGTGT GTGTGTGTGT
32651 GTGTGAGAGA GAGAGAGAGA GAGAGAGAGA TGTTCTTCAA TCTCACATCA
32701 GTTATACTGA TATTTTGCCT TCAGTAAGAT CCCCTAGCTC TTATTGCCTC
32751 TGTGCCCAGT AGATTAACAC TTGGTTGTGT CTTTCTTTTT TCCCTTCCTT
32801 CCTGCCTGCC TTCCATCCTT CCTTCCTTCC TTTTCTTCCT CCCTTCCTTT
32851 CTTTTCCTTC CTTCCTTCCT TCCTTTCTTT CTGTTTCTTT TTTTTTTTTT
32901 TAGACAGAGT CTTCCTCTGT CACCCAGGAT GGAGTGCAGT GGCATGATCT
32951 TGGCTCACTG CAACCTCCGC CTCCCGGGTT CAAGCGATTC TCCTGCCTCA
33001 GCCTCCCAAG TAGCTGGGAT TACAGGCATG TGCCACCATG CCTAGCTGAT
33051 TTTGTGTTTT TAATAGAGAT GAGGTTTCAC CATGTTTGTC AGGCTTGTCT
33101 TGAACTCCTG ACCTCAAGCG ATCCACCTGC CTCGGTCTCC CAAAGTAGTG
33151 GGATTACAGG CGTGAGCCAC CGTGCCTGGC CGCTTGTGTC ATTCTTATTT
33201 TAGTTCTTTG GTTACTTCTT TAGATAAATC TGGACTCCTA ATGCACACTC
33251 TGTAGTTCTC CCAAGAACTG GCTGTTTTGC TGCCTCCTTA ATTTTGGCCG
33301 TATTGCGGGC CATACAGGAG GAACCTGACT TGCAGGCCTG AGTATCACTT
33351 TTACTACCAA AAGTTTTAGT CAGTCACCAT CTTTACTCAG ATCCCAGTTG
33401 AACGGATCTG TCAGAAAAGA GACACTTGGC TAGGGTCTAT ATTAGTTGAG
33451 AGGCTATTTC CAATTCACTT CTCAGCCTGC ATGGTTGTAG GAGCAAGAAC
33501 TGGGATCAGT GAGCCACAGT GAACCTCATT ACATGCCAGG CACTGAAAAA
33551 GTCAGATAAA ACAGTCCATG CTAGCAATGG GGCAAAAGAG GGAGAATTTG
33601 CAAGGGAATC TGTGGCCTAG AGGGCCCAAA ATAGCAGTAG GGAAGGAGAG
33651 GAGGAAGAAA AAGAAGTGAG CCAGGGAGAA GAGCTTGACT GTAGTGGTGG
33701 TGGATGTTTC AGACCTGTGA TATATGACCA ATCATCATTT AAGTGGCTTT
33751 GGGCTGTGGT GAGCTTTCCC AGGGCCAGAG AATAAGCCAG ACCCATACCA
33801 AGTAATAGAA CAGATGGGCA AAGAGTCTTC CACATTCTAC TTGGAAAAGT
33851 AACTTGGTGG GAGAACAGAA GAGAATCCAG CAATAGAAGG TACAGATGTT
33901 AGTCTTCAGC AGCTCTACTC CCTGCCATTT CTCCAACGCT CTGCAAACAG
33951 GAAGTGTGTT TCATAGCCAT AGATCCACAT CTTATTGAGT TTGTTTATAT
34001 GCCAAGACCA TGCTGAGCAC TGTTCTCATC ATACGTAGTT AGCGTCATAT
34051 ATAGTTCTCA CCACAGCCTA TGGTTATCAG TATCCCACTT TACAGAGAAG
34101 GAAACTGACA TTCACAGTAC CCAGCTGGTA TAGTTGAACC TAGAATTGAC
34151 CAGACTGTCC CCTCCAAAGC CTGGATTCTT ATTCCAGGAG GGCCATCAGG
34201 AAAGCTGACA AACACAAAGC CATTTTCCAA GAGCCCTTGG GACTGAACAG
34251 GTCAAGGGTC CTCTGAAGAT TGTCTGGATT CAGGATGCAA GGGTGGGAGT
34301 GGAGCATGTG CCCACAATCC ACAGTGTGTT CTGTGGCTAG ATCCTTGCCA
34351 AATGCAACCA CCTCCCTTCG GCTGAATTCT GTAAGGATAA AAGAGTCCAC
34401 CCCAAAAAGC ATGGCCGGAA AGTCAGGGGA GGGCTCCAAG CCTTCCTGGT
34451 CAAACGATCC ATCAGCCAGA AAAACCCATG TATGACCTCA ACAACTAAGG
34501 ATTACTGTTT CATTGTATTT CAGAATGTGT AGTTTCATAA GATCTGGGTC
34551 TGATTTCTGG TGTTAGTTTC TGAGTCCACA TGTGTGGAAC AGACTCCAAC
34601 CCTTACCACA TAGAATAGGA ACTTTGGTCT ATTTGGGGAG GTGTAGGCAT
34651 TACATTGGGC TAAAGGTTAT GACAGGGTTT GCTATCATGA CTTAAGGTGA
34701 TCCTCACTGA ATTTGTTATT CCACCATCAT TATCTCACTG TTTCAGAGCA
34751 ACTGATACAT TTTTTATTTT GACATTTTAC TGTAAAAATG ACTTTTCTCT
34801 ATGTCTTCTT CCACAGCATG AAAACCAAAT TATTCATAGA GATCTGAAAG
34851 CAGAAAATGT ATTCTATACC AGTAATACTT GTGTGAAGGT GGGCGATTTT
34901 GGATTCAGCA CAGTAAGCAA AAAAGGTGAA ATGCTGAACA CTTTCTGTGG
34951 GTCTCCTCCC TACGCTGCGC CTGAACTCTT CCGGGACGAG CACTACATCG
35001 GCATTTACGT GGATATCTGG GCCTTGGGGG TGCTTTTGTA CTTCATGGTG
35051 ACTGGCACCA TGCCATTTCG GGCAGAAACC GTGGCCAAAC TAAAAAAGAG
```

FIGURE 3M

```
35101 CATCCTCGAG GGCACATACA GTGTACCGCC GCACGTGTCA GAGCCCTGCC
35151 ACCGACTCAT CCGAGGAGTC CTTCAGCAGA TCCCCACGGA GAGGTACGGA
35201 ATCGACTGCA TCATGAATGA TGAATGGATG CAAGGGGTGC CATACCCTAC
35251 ACCTTTGGAA CCTTTCCAAC TGGATCCCAA ACATTTGTCG GAAACCAGCA
35301 CTCTCAAGGA AGAAGAAAAT GAGGTCAAAA GCACTTTAGA ACATTTGGGC
35351 ATTACAGAAG AGCATATTCG AAATAACCAA GGGAGAGATG CTCGCAGCTC
35401 AATCACAGGG GTCTATAGAA TTATTTTACA TAGAGTCCAA AGGAAGAAGG
35451 CTTTGGAAAG TGTCCCAGTC ATGATGCTAC CAGACCCTAA AGAAAGAGAC
35501 CTCAAAAAAG GGTCCCGTGT CTACAGAGGG ATAAGACACA CATCCAAATT
35551 TTGCTCGATT TTATAAATTG CACTAGACTG CTTGTAACTA ACCAAGATGA
35601 TTGTTGCTGC TTCTAAATTT TTTTCAAGGA CAACTTGAGT GGAGACATTT
35651 TTGTAATTTT TAAATAAACT TAAATTTGAG ATATGCATTT TTTTTCTCCA
35701 AAAAGTCTAT TAGCTCAGAT TCTGGCTTGA TTTGGGATCT TGTTTTATTA
35751 TCAAATTTCA GCATTCATTC ATTTAATCAA GAAATATTTA TCCAGTGCCT
35801 CCTGTGTGTC AGGCACTATT TAAGGTGCTA GGGAAACAGC AAGAAATAAA
35851 TAGGCAAGGT CCCTCCTCTC ATGTGCAGGA CGTTCTAGCC CAGGACAAAG
35901 GTACTAACAA CTACATTTTT TAAAAAAGAG AAAGATCAGT GATAGATGCT
35951 ATGCAGAGGA TTCAAAAAGG GTGATCTGAT ATCAGAGGCT TGCTACTTTG
36001 GATTAGTCAT TAAGGAAGGC CACTTTGAGT ACATATAAGT TTAAGATCTG
36051 AATGAGAAGC AGGAGTGACT TTTACAAAAT GCCAGAGCAT TCCAGGCAGC
36101 TAGGGGTTTC AGACTCAGTT CCCCCCAAAA CAGAGCCTAA GACAAAGGCT
36151 TCCATATAAA GTAGTTTATT TGGGAACTGA TCCCAGAGCA CAGGAGTGAA
36201 GGACAGAGGA AACAGGGAAA GCTAATACAC AGACACATTA GCAAGTTAGC
36251 TAGTGCTACA GTTTCTGGTG CTTGGTTTTG CAGGATCCTC CAGAGGAGCC
36301 TGATGAAACA CATCTCAGGT GTCTGCCCTG GGTATGAAAG GGGAAAGCAT
36351 TTAACCATAA GCTCTTGCTC ACCGCTGATC AAGGGTGGCC CTTTGTGTCA
36401 TCTGCCCTGC ACTCCAGAT TGGGCTGTGT GAATGCCAAG TGGGTTCCCT
36451 AAGCTTCCCT TGCCTTCATG TCAGAGAAGT CTTGGAGCAG GAGGGAAGAG
36501 GTACACCACC AGTACGATAC CTCCTTTCTT TGCCTGCTTG TCCACTGGCA
36551 TGGGGAGCCC AAAGTGACCA TGTGACACTT GTAGATTCCA ATTCACTGGA
36601 GCCCTTATCA AGTCCCCTGA TGAAAGCATC CCTGATCCCC TGGGAACCAA
36651 ACCTTTTAAT CTAGCCTAGA TTGTAGAAAA AAAAAGAATA GAAATTAATC
36701 AAGTGAGTCA CCAATTGCGT GATGGTGACA GGAGTCAATC TACTTCCACC
36751 TAGTGGTTTC CAGACCTGTG TTTTAATGAT AGGGACATGT ATCAGTCATT
36801 ATTAAAGCAT GTTACTGAAT CCTGGAGGAC AGCACCCCAA CCCTGCAGGC
36851 TGCTGTCTCA TCTCTGGTGT CTTAGCTGAG TCATTCCATT GTTCTACTCA
36901 TGTTGGCTGC TTCTGATGTT GAGGTATATG GTAAGATGAG GGGATCCCGT
36951 TGTCATGTGC CCATTGCACC ACCTCCTTTA TCAAAAAAGT GGTCCTTGAG
37001 GCAATGTTTG AGATATCATG ACAGTGAGTC AGTTATTCTC TATGTCTTAG
37051 TGTGCTTGTA TGGAAAGACA CATTGCAGGC AGAAAAGGCA AACCCATACC
37101 CTGAGATATC AATTCCAATA AGGATGAATC ACTCCTGGGC CCATCTGAAT
37151 TCATGACTCC ATGGATCTGA TAATGCCCAG CTCATACGTT AACAGCTCTG
37201 TTTGCCTAGT CCTCAGTATC TCATAATCAG GTTCTCAGCC TCCACTGGGG
37251 CCCAGTAGCA CATCGGGAGT CTGAGTAGTT CTGTCGCAGG AAGCATGGCG
37301 TTACTACAGG ATCCCACAGA GCTGTGCTGT TATCTCTTAT TGGGGCTTTC
37351 CAGAGGCCCC ACACTACACA GCCTGAGTAG CAGTTTGCTC AGAAGCCAAA
37401 ATTGCTGCAA TCTTTCTTTT ATGGGATCCA CTTGAAACTG GCAGCCGTGT
37451 TAAATGGGTG GGAGGAATAC ACCAGATACA ATATATGTGC TTCCAAAGTC
37501 CAGAGGGACC TACTAAATCC TATGCCTCTA TCTTAGTGTT AAGAGGTGGG
37551 AGGTGCAAGA AATTGTTCTT TACTATAGAA GAAATATCTA GGCATGCCTC
37601 AACTCATTGG TCTTCTAAAC TCTTCATCAA TGTGGCATGC CCCAGATTCT
37651 TCATAGAGTC TATAATCCAC ACCCTGGCAC ATGTAAGCCT TACTAGGGCA
37701 TTGGTAATAC TTGCCACTTC CTGATAGCCA ATCCCCCTAG CATGCTCTCA
37751 CAATATAGTG GGCCAGCATG ATGTCCTGTA GAATGTCAAG ATGATCAAGG
```

FIGURE 3N

```
37801 TCCTTTTGGA TTATATTGTG ATATAGAGAA GGAGATTTAA GATTGTTTTG
37851 GGGCAATAGA GTAAATGAGA ATCGCTCTCC ATCCCAGAGA AATGTGAACT
37901 GCTTTTGATC CTCCTTTCTG ATGGAAATTT AGAAGAATGA ATTTGCCAAA
37951 TCAATAGCTG CATATCAAAT GCCAGAGGCT GCCAGTAAAG ATACCACATC
38001 CAATATGGCA GCTACAACTG AGACTAGCAG TAGTCCACCA TCATTCTCCA
38051 TTATCCATCT GCTCTTTTTC AGAAGTGTAA TGGTAACTTA AATGAGATTA
38101 TGATGGAGCC CATTACACTT GCATCCCAAA ATTTTTTGAT GGTGACACTG
38151 ATGTCTGCCA TTCCTCATGT GGATTGCTCA TGATTTATTA ACATGGCCAG
38201 AAAGAGGTTT CCTCTTTCTC CCATAATGGT TGTTACTTCA CAGGTCTAAG
38251 ACCTCCACAG AGGTCTAAGT ATATTGATCC CAAATATGTA CTTAGAGGTT
38301 GGGAGAATAA TTCCAAGGTG GGAACCATTA TGTGATAGAC TTTGGCCAGG
38351 ACTCCCTTTA TCATATGGTT TCCATAACCC CTCATCTACG TACAAAGCCA
38401 TAATGGTATC CGGTTCTGAA AAATTCTGGG TATGTACATC ATATATACTT
38451 GTGAAAGCAA GGCCTTTCCT CAAGACCAGT CCTCCTTTTC ATTGTGCACT
38501 GGATCTGTAA ATTGACTTAG CTCTGGAAGC TGATGAAGAG ACCGTGATTT
38551 TCCCATTGTG ACAG (SEQ ID NO:3)
```

FEATURES:
Start:    3000
Exon:     3000-3291
Intron:   3292-31893
Exon:     31894-32162
Intron:   32163-34816
Exon:     34817-35563
Stop:     35564

CHROMOSOME MAP POSITION:
Chromosome 5

ALLELIC VARIANTS (SNPs):
DNA

| Position | Major | Minor | Domain |
|---|---|---|---|
| 1681 | C | A | Beyond ORF(5') |
| 6888 | T | – | Intron |
| 7939 | A | G | Intron |
| 9790 | G | A | Intron |
| 11689 | G | A | Intron |
| 12145 | A | G | Intron |
| 12437 | A | – G | Intron |
| 12437 | G | – | Intron |
| 22982 | C | T | Intron |
| 23239 | C | T | Intron |
| 23859 | A | G | Intron |
| 24862 | G | A | Intron |
| 25097 | G | A | Intron |
| 25751 | C | T | Intron |
| 25934 | T | – | Intron |
| 26179 | G | A | Intron |
| 26277 | A | G | Intron |
| 26354 | – | T | Intron |
| 26356 | T | – | Intron |
| 26359 | T | G | Intron |
| 29484 | G | A | Intron |
| 29885 | A | T | Intron |

FIGURE 30

| | | | |
|---|---|---|---|
| 30601 | C | T | Intron |
| 30920 | C | T | Intron |
| 31057 | C | A G | Intron |
| 31097 | G | A | Intron |
| 31204 | T | C | Intron |
| 32660 | T | A | Intron |
| 32875 | T | - | Intron |
| 33477 | C | G | Intron |
| 34059 | C | T | Intron |
| 36681 | - | A | Beyond ORF(3') |
| 36821 | C | T | Beyond ORF(3') |
| 38079 | A | G | Beyond ORF(3') |
| 38432 | A | T | Beyond ORF(3') |

Context:

DNA
Position
1681    TTGAGCAGAGTTGGAAATCCATACTTCCAAGGCAGTCTCTCATGTTTTCAGTCAAATTTT
TGGTTTGGAATGCTCAAGTCCAAAAATCAAGTTTAACACATATTTACTTAGTAAACACTT
TCTATATGTAAGAACTTATACTCCATTTTTGAAGGAGAGAGGAGGTGAGCAGGACATACCT
ACAAGTCAAAACCAGTTCCCACCTTCACTGAGATGGGACATTTTGGAAAATGCACGAAGT
GCTGTGGGAATTCAGAGAGGAAGAGAGTATTTCCTGCTGGAGAGTGCAGAAAAAAAACAT
[C,A]
CCGATGACATCGTAGGTGGGCAGCATTTCTTGTCACTGGCAATGCTGTAAACCCTCCTTT
TCCACATCTTCAAAATAAGGTGCTGGGCCTAGAAACTGACACCTGCTCAGAAAAATTCAA
AAAGTGAATGTAGGAGGAAAAATCAGCCTTTGTCATAAAATGACATAGGAAGAAAGAGTG
GAAGCAACTAGTATAGGACAAGTTGTGCAAGAACATGAAGTAGTAAAGGAGATAAAATAT
TATTATTTGAATAAATATGAGAAATTTTGAAAACCATTAGTAATCCGGAATCTTTCATCT 6888    CTGCCTCCTGGGTTCATGCCGTTCTCCTGCCTCAACCTCCCGAGGAGCTGGGACTACAGA
CACCCACCACCACGCCTGGCTAATTTTTTGTATTTTTAGTAGAGACGGGGTTTCACCATG
TTAGCCAGGATGGTCTCGATCTCCTGACCTCGTGATCTGCCCGCCTCGGCCTCCCAAAGT
GCTGGGATTACAGGCATGAGCCACCGCGCCTGGCCGGATTAGTTTTAAATATGCTAATGG
AATCATTCACTGTTGCTCCATGAACACTATGATTTTTCAATGTCATTAAATATAGATTTT
[T,-]
AAAATATATTTATGTGTATATATTATCTATATATGTGTATTTATTATCTATACTCTCATC
TTTTAAAGAGGACATATTGTTTCACATATAGCTGTGGCATAAATTCTTTAACTTAGCCAC
TATTGGTTAACATTTGGATCATTTCTAAAGTTTTGCTCTTAATTATAATGCTACAGAGAT
TATTCTTTTCCATACTTCTTTGCATATACGTATGATTTCTCTCAGCATACATTCCTAGAA
GTTAGCTGTCTTGGTCAGAGGGCATGCATTGAAAAATTTTAACACACAGCACCAAAAGAG 7939    GTTGCCTCAGCTGTAAAATAGAGATAATGATTTTTAGAATTGTTGGGGAAATTGGAAATA
ATATATGTGAAGTACATGACATATAGTAACCACTCAAAATGGTAGCTGCCATTGCTATAA
CTTTACTTTTTAATTAATCTTATTTCAAAAAGGTATTTAATGTTATTACAACAATAAAAA
CCAGTATCACTTACTATGAATAGAAGGTGATGGTAAAAATAAATACAATGCAAACAAATT
AAAAAGCATTAAAGGAAAATTACAAGTAACAAAGTAATTTTTAAAACATGCTAACAATCA
[A,G]
TCTCAGACTTTCTCTTTGCCTTAATTAGGAGAATTAAAGGAGAGCTGAAATGGGAATCAT
GTTTTTACGCTGTGATTCAGTGCTATTTAAGGCTGTTTCCACGCCCTAAAATCATTTCAA
CCTCATGAGTCTTAAAGGTTCCACTTTGGGAAGCACTGACATCATCTAGTCCTTCCATGT
TTTACAAACGAGGAGATGGAGGCTCAGAAGAGGCTGTCCCAAGGTTTAGAACCTGTTTAC
AGGAATTCACATGGAATTGAGTACTCACATGTATTGAGTACAGGGGAATTCTATGGACCC

FIGURE 3P

9790    GAATGTGGGTGTTTTTTTCTGTTGCTGCCCTTCTGACTTCTTCCTTCTGCTACTCTAGTC
TCATGTTTCTAGGATCCTTTCTTCCTCCCACTTTATTTATCTATTTATCTATTAATTCAT
TCTTTCCTTCCTTCCTTTTTTTTTTTTTTTTATCTTTTGAGGAAGAGTTTTGCTTCATTGCC
CAGGCTGGAGTGCAGTGATGCGATCAAAGCTCACTGCTGCCTTGGACTCCTGGGCTCAAG
TGATTCACCCACCTCAGCCTCCCAAAGCACTGGGCATTACAGGTGTGAGACACCATGACT
[G,A]
GCCTTCATTCCTTTATATATATATATAATATAATATATAATGTAATATATAATATAATAT
ATAATATAATATATGTGTGTGTGTGTGTGTGTGTGTGTGTGTGTAAGCAC

11689   TTCTAGAGATGAAGTCTCAACTATGGTTATCCAGGCCGTTCAAGAACTTCTGGGCTCAAG
CAATCCTCCTGCCTCAGTTTCCTAAGTAGCATGGGGGACAGCTATGCACCACTGCACCTG
ACTGCTCACTGGTTTTAAAAATTGATTCCCCCCTCTTGAATACATTCATTAAAATAGCAA
TTCAAAATTGTATTTTCTTACTTTAAAAATGGTTAGTTAGTGATTTAGGGAATTCACCCT
AAAAATAAATCATATATTGGAAATACTACAACCAAAAAAATGTTCATTGTCGTGTTATTT
[G,A]
TAGTGTCGAGAACTAGTAATAACTTATGGGATCCAATGATATAGGAATGGTCAGGTAAAG
CATATACACTGGGCAGAAGATTCCATAGCCATGAGAAATCATGATTATGAAGACTCTGTG
GTAACATGAAGATGGGCAGGACATGAGTGTAAGTGAAAAGCCAGGTGCAAATGGAGCGC
ACACTATTATGATAATACTTACTCCAGGTTCTTCAGTGAGATTATTCACTCAGCAAATAC
TTGTTGAGCACCTACTATGCAATAGCCACTATTCTAGAGACTGGTGATACAGCAGTGAAC

12145   GAAAAGCCAGGTGCAAATGGAGCGCACACTATTATGATAATACTTACTCCAGGTTCTTCA
GTGAGATTATTCACTCAGCAAATACTTGTTGAGCACCTACTATGCAATAGCCACTATTCT
AGAGACTGGTGATACAGCAGTGAACAAAATAGACAGCAATCTCTGTCCTTATGGAACTTA
CACTCTAGTGAGAGGGAAGCCAGACAAAAATAAATGTGTAAAATATTCATTGTATTATGT
AGCGATAAGTGATAAGAAAGAAAAGAGGGCCGGGCGCGGTCGGTCACGCCTGTAATCCCA
[A,G]
CACTTTGGGAGGCCAAGGTGGGTGGATTATGAGATCAAGAGATGGAGGCCATCCTGGCCG
ACATGGTGAAACCACAATTCTACTAAAAATACAAAAATTAGCTGGGCATGGTGGTGTGCA
CCTTTAGTCTCAGCTACTCAGGAGACTGAGGCAGGAAAATCGCTTGAACCCAGGAGGGGG
AGGTGGCAGTGAGCCAAGATCGTGCCACTGTACTCCAGCCTGGTGACAGAGCCAGACTCT
GTCTCAAAAAAAAAAAAGAAAGAAAGAAAGAAAGAAAGAAAGAAAGAGCAGGAGGG

12437   TAATCCCAGCACTTTGGGAGGCCAAGGTGGGTGGATTATGAGATCAAGAGATGGAGGCCA
TCCTGGCCGACATGGTGAAACCACAATTCTACTAAAAATACAAAAATTAGCTGGGCATGG
TGGTGTGCACCTTTAGTCTCAGCTACTCAGGAGACTGAGGCAGGAAAATCGCTTGAACCC
AGGAGGGGGAGGTGGCAGTGAGCCAAGATCGTGCCACTGTACTCCAGCCTGGTGACAGAG
CCAGACTCTGTCTCAAAAAAAAAAAAGAAAGAAAGAAAGAAAGAAAGAAAGAAAGAAAGA
[A,-,G]
CAGGAGGGGAGATAGAAAGCATTGAGGATGACAGTTTTTAGATAAGTTGGCCAGGACAGC
CTTACTGAGGAGGTAATAATTAAACTGAAAGAAATGAGGGAAATGGCTATACATGGGGGA
ACTCCATCAAGCAGAAGGCGTAGCAGGCGTAAGAGTGTCCAGATGGGAGATGCCTGCAGT
ACTCTTGAAACAGCTGAGGGGAAAGGGCAGAGAGTAACAGGGAACAGATTGTGGAGGACC
AAGTTTGTCAAAGTAAGAAGTTTGGCTTTTCCTGGGATTTTACAGGAGCCATCAGAAGGA

12437   TAATCCCAGCACTTTGGGAGGCCAAGGTGGGTGGATTATGAGATCAAGAGATGGAGGCCA
TCCTGGCCGACATGGTGAAACCACAATTCTACTAAAAATACAAAAATTAGCTGGGCATGG
TGGTGTGCACCTTTAGTCTCAGCTACTCAGGAGACTGAGGCAGGAAAATCGCTTGAACCC
AGGAGGGGGAGGTGGCAGTGAGCCAAGATCGTGCCACTGTACTCCAGCCTGGTGACAGAG
CCAGACTCTGTCTCAAAAAAAAAAAAGAAAGAAAGAAAGAAAGAAAGAAAGAAAGA
[G,-]
CAGGAGGGGAGATAGAAAGCATTGAGGATGACAGTTTTTAGATAAGTTGGCCAGGACAGC
CTTACTGAGGAGGTAATAATTAAACTGAAAGAAATGAGGGAAATGGCTATACATGGGGGA
ACTCCATCAAGCAGAAGGCGTAGCAGGCGTAAGAGTGTCCAGATGGGAGATGCCTGCAGT

FIGURE 3Q

```
          ACTCTTGAAACAGCTGAGGGGAAAGGGCAGAGAGTAACAGGGAACAGATTGTGGAGGACC
          AAGTTTGTCAAAGTAAGAAGTTTGGCTTTTCCTGGGATTTTACAGGAGCCATCAGAAGGA

22982     TGTTTTGTAGCCAATCGTATGGCCTATGTTGGAATATATTCCATGTGCTGATGAGAAGAA
          AGTATATTCTATAGTTTTTGGGTAGGATGTTCTGTAAATATCTGTTAGGTCTACTTGTTT
          TAGAGTATTGTTTAAGTCATTGTTTCTTTGTTGACTTTCTGCCTCGATGATCTGTCTAGT
          GCTGTCAGTGGGGTGTTGAAGTATCCCACTATTATTGGGTTGCTCATTATCTCTTTCCTT
          AGGTCTAGCAGTAATTGTTTTATGAATTTTGGAGCTCCATAGTTAGGTACACATATATTT
          [C,T]
          GGATTATAATATTCTCTTGTCAGATTAATCCTTTTATCATTATATAATTGTAACCACCTA
          ACAGGTTATTTCTGCCCACTGCACAAGCAAAATCAATTCATGGCATTGTGGTGAAGAAAG
          TGTTTAATTGATGCAAGGCCAGTCATGCCATGTGGTCAAACTAGGATGGAGATATTACTC
          AAATCAATCTCATCAAAGGCTTGTTGGTTAGGGGTTTTTCAAAGGCAGTTTTGGGGAAGG
          GATTGGGCTGACCAGACCAGGTGCTTGCTGCTGATTGTTTGGGTTGGAGATGAAATCATA

23239     TTTTATGAATTTTGGAGCTCCATAGTTAGGTACACATATATTTTGGATTATAATATTCTC
          TTGTCAGATTAATCCTTTTATCATTATATAATTGTAACCACCTAACAGGTTATTTCTGCC
          CACTGCACAAGCAAAATCAATTCATGGCATTGTGGTGAAGAAAGTGTTTAATTGATGCAA
          GGCCAGTCATGCCATGTGGTCAAACTAGGATGGAGATATTACTCAAATCAATCTCATCAA
          AGGCTTGTTGGTTAGGGGTTTTTCAAAGGCAGTTTTGGGGAAGGGATTGGGCTGACCAGA
          [C,T]
          CAGGTGCTTGCTGCTGATTGTTTGGGTTGGAGATGAAATCATATGGAGTTGAAGCTGTCC
          TCTTGTGCTGAGTCACTTCTGTGGGGCCACAGGAGTGGTTGGTGGGTCCATATGGGTCCA
          AGTGAAGCCATCGGTGTCAGACATGCAAAAAACCTGAAAAGATATCTCAAAAGGCTAATC
          TTAGGTTCTACAATAGTGATGTTATCTGCATGAGTAATTGGGGGAGTTGCATATCTGTGA
          CCTCTGGAATAATGGCTGTCAATCATTTATATCCACACCTTAGCAGAATTCAGGCTCTTC

23859     GGTTTCTCATTAGCTTTACAAAGGTGACTGAGTTTTGGGAAAGATTATTATCATTTAAAC
          TACAAACTAAATGTCTCCCAAAGCTAGCCAAGACTAAGCCCAGGAATAATTAAGGCAGCT
          TGAAGGCTAAAGGCAAGAGGGAGGTTGGCTAGATCAGATGTCCCCCACTGCCATAATTGT
          CTCAGTGATATAATTTTTGCAAAGGTGGTTTTATAATGACCTTCTTTGTCTTTTTCTTTT
          TTTTAACTGTTGTTGCTTTAAAGTCTGTTTTATTTAATATAAGAATAGCCACTCCTACCC
          [A,G]
          GGCACGGTGGCTCACACCTGTAAATCCCAGCACTTTGGGAGGCTGAGGCAGGTATATCAC
          CTGAGGTCAGGAGTTCAAGACCAGCCAGACAGAGATGGTGAAACTCCATCTCTACTAAAT
          TTACAAAAACATTAGCCAGGCATGGTGGGGGCACCTGTAATCCCAGCTACTCAGGAGGC
          TGAGGCAGGAGAATTGCTTGTACCCGGGAGGCAGAGGTTGCAGTGAGCCAAGATTGCGCC
          TTGCTCTCCAGCCTGGGCAACAAAGTGAGACTTCATCTCAAAAAAAAAAAAAAAAAAAA

24862     TGCCTCAGCCTCCCGAGTAGCTGGGACTACAGACACCCGCCACTACGCCTGGCTAATTTT
          TTGTATTTTTAGTAGAGACGGGGTTTCACCATGTTAGCCAGGATGGTCTCGATCTCCTGA
          CCTCGTGATCCACCCCCCTTGGCCTCCCAAAGTGCTGGGATTACAGGTGTGAGCCACCGT
          GCCCGGCCATGTGTGTGTGTTATTGTTTTATAGGCCCTGTGAGTTTTATGCTTTCAAGAG
          GTTTTATTCTGATGCATGTCAACTTTTGGTTTCAAGATTTAGAAGTCCTTTTAGAATTTT
          [G,A]
          TGTATGGCTGGTCTGGTAGTTACAAATTCCTTCATCATTTGCTTGTCTGGAAAAGACTTT
          ATTTCTCTTTCATTTATGAAACTTAGTTTTGCTGGACACAAAATTCTTGACTGACACTTA
          TTCTGTTTAAGGAGGCTAAAGATTGGACCCCAATCCCTTCTGGCTTGTAAGGTTTCTGCT
          GAGGGGAAGATTTTTATCAATGACATAAATGTGTGATGATGGAAACAATCCAGTGGGAAG
          AGAAAATTGATGCAGGAGAGAAGAAAGAAAGCTTTTTTGGAGGGCTGCTCTTTAGTATAT

25097     AAGAGGTTTTATTCTGATGCATGTCAACTTTTGGTTTCAAGATTTAGAAGTCCTTTTAGA
          ATTTTGTGTATGGCTGGTCTGGTAGTTACAAATTCCTTCATCATTTGCTTGTCTGGAAAA
          GACTTTATTTCTCTTTCATTTATGAAACTTAGTTTTGCTGGACACAAAATTCTTGACTGA
```

FIGURE 3R

```
        CACTTATTCTGTTTAAGGAGGCTAAAGATTGGACCCCAATCCCTTCTGGCTTGTAAGGTT
        TCTGCTGAGGGGAAGATTTTTATCAATGACATAAATGTGTGATGATGGAAACAATCCAGT
        [G,A]
        GGAAGAGAAAATTGATGCAGGAGAGAAGAAAGAAAGCTTTTTTGGAGGGCTGCTCTTTAG
        TATATGAGAGTAGATGGAATCTATTCAACATGTAAAGGAGTCTTAGCTAGGCCTTAGATA
        GGAGTAGGAATTGTTTATCCAAAGTAAAATGAAGGAAGAGAGATTCCAGTAGGTTGGAAG
        ACATGGTGGGAAGGACTTGAGGAAATTCTCCTCTATTGCTTATTTTACTCAATAAAGTAG
        GAAGCAAGGTTACCAGCTGTGAATGAGGAGTGGAAGAAGGCATTAGAGACTTGATGAGAG

25751   GAAAGTATGTCTGCCAGGCGCTTTAAAGGGCCAACTGAAGTTAGTGACCAGAAATTCAAA
        GTGAGACAAGCCATTATGTCCAACAGCATGGGTGCAGGCAGAGAGTAGTGGGAAGCTGGA
        TTTAACCAGAGTCATGGTTTAGCAAAGTGAACTCAACAACCTGGGAGAGAGACAGGGGAA
        CTTAGGGAGTGCCCGAAGGCATGATAACATTAATAGAGATCCTCCTCCAGTGAATGTCAC
        CAGCCTCCCAGTTGCTCAACTGAGAAACCTTGACCTTTTCCTCAACCCCTAACACCCAAA
        [C,T]
        ACCAAGTGGTATTGATTTCACTTCCTAAATATCTCCTCCTTTCCTCATTGGATTAAGCTA
        CTGTAATTTGTCTTCATGTTTATATCATTTCCCCCATAGCAGCCAGAGGTGATGTTTTAG
        AAATTACAAGCCTGATCATGTAACTACCTACTTACAAGCTTCCAGCAGCTTCTTTTTTTT
        TTTCAAGTGGCAGTTTTAAGTTTGTGGGTTTTTAATTTATATATGTGAAATACCTTTTTA
        TAGGCAAAAATAATAATAGCATGCTTCTTACTGCCCTTAATGTGAAATGACTCACAAGAC

25934   AGGGAGTGCCCGAAGGCATGATAACATTAATAGAGATCCTCCTCCAGTGAATGTCACCAG
        CCTCCCAGTTGCTCAACTGAGAAACCTTGACCTTTTCCTCAACCCCTAACACCCAAACAC
        CAAGTGGTATTGATTTCACTTCCTAAATATCTCCTCCTTTCCTCATTGGATTAAGCTACT
        GTAATTTGTCTTCATGTTTATATCATTTCCCCCATAGCAGCCAGAGGTGATGTTTTAGAA
        ATTACAAGCCTGATCATGTAACTACCTACTTACAAGCTTCCAGCAGCTTCTTTTTTTTTT
        [T,-]
        CAAGTGGCAGTTTTAAGTTTGTGGGTTTTTAATTTATATATGTGAAATACCTTTTTATAG
        GCAAAAATAATAATAGCATGCTTCTTACTGCCCTTAATGTGAAATGACTCACAAGACCTT
        GGTGTGGCCAACTCTCCAGCCTCTTTTTTGGCTTATATTTTTCCTTCTTCCCCATATGCC
        AGCCCTACTTCTTCTTTCAATTCTTCAAAGTCAGTCATCTCTGAGGGTGCATATACCCC
        CAGAGAATGCCCAAGATGATTCACTGGGATGAGGAAAAAAAATACTAGAACTTCCTTTTA

26179   AAGCCTGATCATGTAACTACCTACTTACAAGCTTCCAGCAGCTTCTTTTTTTTTTTTCAAG
        TGGCAGTTTTAAGTTTGTGGGTTTTTAATTTATATATGTGAAATACCTTTTTATAGGCAA
        AAATAATAATAGCATGCTTCTTACTGCCCTTAATGTGAAATGACTCACAAGACCTTGGTG
        TGGCCAACTCTCCAGCCTCTTTTTTGGCTTATATTTTTCCTTCTTCCCCATATGCCAGCC
        CTACTTCTTCTTTCAATTCTTCAAAGTCAGTCATCTCTGAGGGTGCATATACCCCCAGA
        [G,A]
        AATGCCCAAGATGATTCACTGGGATGAGGAAAAAAAATACTAGAACTTCCTTTTATATTT
        ATTTGTGATTATATATTTTTAATTTCTGTGATTATATGTATTGAAAATGTGTAAATCAGT
        AGTACATGGATACACTTTATAAATACATATACATATATTAGAGTAGTGCTCAAATATATT
        TTTTATTATGCACATGCAGTTGTAAGAATATGTACAGAGACCACATGTACCATTTACCCA
        GTTTCACACAAACTTGCATCTTGCAAAACTATAGTCATAACCTTGATATTAATATTGATC

26277   TGAAATACCTTTTTATAGGCAAAAATAATAATAGCATGCTTCTTACTGCCCTTAATGTGA
        AATGACTCACAAGACCTTGGTGTGGCCAACTCTCCAGCCTCTTTTTTGGCTTATATTTTT
        CCTTCTTCCCCATATGCCAGCCCTACTTCTTCTTTCAATTCTTCAAAGTCAGTCATCTC
        TGAGGGTGCATATACCCCCAGAGAATGCCCAAGATGATTCACTGGGATGAGGAAAAAAAA
        TACTAGAACTTCCTTTTATATTTATTTGTGATTATATATTTTTAATTTCTGTGATTATAT
        [A,G]
        TATTGAAAATGTGTAAATCAGTAGTACATGGATACACTTTATAAATACATATACATATAT
        TAGAGTAGTGCTCAAATATATTTTTTATTATGCACATGCAGTTGTAAGAATATGTACAGA
        GACCACATGTACCATTTACCCAGTTTCACACAAACTTGCATCTTGCAAAACTATAGTCAT
```

FIGURE 3S

```
              AACCTTGATATTAATATTGATCTAATTCACTGATCTTATTAAGATTTTCCCAGTTCTTGT
              ATTCATGCATGTGTATGTATTTTAACTCTATGGAATGTTATCACATAAATAGGTTGTTAT

26354   TGGTGTGGCCAACTCTCCAGCCTCTTTTTTGGCTTATATTTTTCCTTCTTCCCCATATGC
              CAGCCCTACTTTCTTCTTTCAATTCTTCAAAGTCAGTCATCTCTGAGGGTGCATATACCC
              CCAGAGAATGCCCAAGATGATTCACTGGGATGAGGAAAAAAAATACTAGAACTTCCTTTT
              ATATTTATTTGTGATTATATATTTTTAATTTCTGTGATTATATGTATTGAAAATGTGTAA
              ATCAGTAGTACATGGATACACTTTATAAATACATATACATATATTAGAGTAGTGCTCAAA
              [-,T]
              ATATTTTTTATTATGCACATGCAGTTGTAAGAATATGTACAGAGACCACATGTACCATTT
              ACCCAGTTTCACACAAACTTGCATCTTGCAAAACTATAGTCATAACCTTGATATTAATAT
              TGATCTAATTCACTGATCTTATTAAGATTTTCCCAGTTCTTGTATTCATGCATGTGTATG
              TATTTTAACTCTATGGAATGTTATCACATAAATAGGTTGTTATATTCCCCACCACAGTAA
              AGATACAGGACAAGTCCATTATCACAAGGGCCCTTCAAGTGGCTCTTCTGTAGCCACCTC

26356   GTGTGGCCAACTCTCCAGCCTCTTTTTTGGCTTATATTTTTCCTTCTTCCCCATATGCCA
              GCCCTACTTTCTTCTTTCAATTCTTCAAAGTCAGTCATCTCTGAGGGTGCATATACCCCC
              AGAGAATGCCCAAGATGATTCACTGGGATGAGGAAAAAAAATACTAGAACTTCCTTTTAT
              ATTTATTTGTGATTATATATTTTTAATTTCTGTGATTATATGTATTGAAAATGTGTAAAT
              CAGTAGTACATGGATACACTTTATAAATACATATACATATATTAGAGTAGTGCTCAAATA
              [T,-]
              ATTTTTTATTATGCACATGCAGTTGTAAGAATATGTACAGAGACCACATGTACCATTTAC
              CCAGTTTCACACAAACTTGCATCTTGCAAAACTATAGTCATAACCTTGATATTAATATTG
              ATCTAATTCACTGATCTTATTAAGATTTTCCCAGTTCTTGTATTCATGCATGTGTATGTA
              TTTTAACTCTATGGAATGTTATCACATAAATAGGTTGTTATATTCCCCACCACAGTAAAG
              ATACAGGACAAGTCCATTATCACAAGGGCCCTTCAAGTGGCTCTTCTGTAGCCACCTCCT

26359   TGGCCAACTCTCCAGCCTCTTTTTTGGCTTATATTTTTCCTTCTTCCCCATATGCCAGCC
              CTACTTTCTTCTTTCAATTCTTCAAAGTCAGTCATCTCTGAGGGTGCATATACCCCCAGA
              GAATGCCCAAGATGATTCACTGGGATGAGGAAAAAAAATACTAGAACTTCCTTTTATATT
              TATTTGTGATTATATATTTTTAATTTCTGTGATTATATGTATTGAAAATGTGTAAATCAG
              TAGTACATGGATACACTTTATAAATACATATACATATATTAGAGTAGTGCTCAAATATAT
              [T,G]
              TTTTATTATGCACATGCAGTTGTAAGAATATGTACAGAGACCACATGTACCATTTACCCA
              GTTTCACACAAACTTGCATCTTGCAAAACTATAGTCATAACCTTGATATTAATATTGATC
              TAATTCACTGATCTTATTAAGATTTTCCCAGTTCTTGTATTCATGCATGTGTATGTATTT
              TAACTCTATGGAATGTTATCACATAAATAGGTTGTTATATTCCCCACCACAGTAAAGATA
              CAGGACAAGTCCATTATCACAAGGGCCCTTCAAGTGGCTCTTCTGTAGCCACCTCCTAAC

29484   CAGGAGGGGGCAGCAGAGTGATGATACCTTAACTGACACCTGAGTCAGTAATGGGAGAAC
              TGAGGAGAAGCAGTGGGTTCTTCTACAGGAAATCGAAGGGTGGAATTCATTAATCTAGCC
              CTTAAAACAACAGCTTACCCAACATGCTACACAAAACCAGGTTTCTGTTTCAGATAAATA
              GGTGAAGGGACTCTTAATCCTAAAGACTGAAAAGTAGAAAAGAAAGGGGAAGAAGAGTGC
              CTCAAGGATTGCCATTGGAGGTTCTTTTGCTGGGGCTGATTGCCAGCTGAGATTATTCAA
              [G,A]
              CCCCAGAGCAAACATTCTGCTCCTGCTCCCTTAGAGCTGCCCTCCCACCGCTCAGTATTG
              CCTCCTGCGAGGGGCGGGCTGGCTGCCGCAGACACCAGTGAACCCTTTTTCCATTCCAGA
              AGTCCCAGTGGACCTACTTTAATATACCAATAACACTCCTATTTTAAACTAGCTGTATCC
              ATTTTCGTTTTAATAGTCCCAGTGCTAAAGTTTTTCAAAGCAGTTATTTTGTAAGTAGGT
              CAAACAGGTACTTTGGGATCCTGTTCTGTCTGTTTGCTTGCCAGGTAACCTCTTTGTTAT

29885   AACCCTTTTTCCATTCCAGAAGTCCCAGTGGACCTACTTTAATATACCAATAACACTCCT
              ATTTTAAACTAGCTGTATCCATTTTCGTTTTAATAGTCCCAGTGCTAAAGTTTTTCAAAG
              CAGTTATTTTGTAAGTAGGTCAAACAGGTACTTTGGGATCCTGTTCTGTCTGTTTGCTTG
```

FIGURE 3T

```
        CCAGGTAACCTCTTTGTTATCTAATTCAAAGTCTGGTACAGTTTGAACCAAAACAAAAA
        GGAATGATGTTTCACTTTGGAGTCAAGATTCATTCATTTTCTAACATTAATCATTTTCGT
        [A,T]
        ATACAGTAAGTCTATATTCATGATAAAAAATAGAAAATATGAATAAGCAAAACTAAATTG
        AAAGGAAAACCATCTGTGATCTGCCAATTAGAAAATCTCTATTCTAAACATTTTGGTAAA
        TATGCTACCAGATTTTTATCTATGCAAATGTGTATCTGTATTTTTCCTCACTTGTATAGT
        GGACATCTTTTCATATTAATAAATAAGTTAGCATCATTACTTTTGATAGCTTCATGGTGT
        GAAATTATAAAATTAGACCTACCACACTCTATTTTAACTATCTCTCTTGCTGGGTACTTA

30601   CATTTCAATACATAATACCAAAGTGCAATCCAGAACCATTGTACCAATTAATGCTCCCGC
        CAGCAGCACATTGCAGTGTTGATTTCCTCCTGGCCTCACCAGCACGCTGTCAACACTGGG
        TACTGGTGTGTCGTGTACATGACATTACATGCCAGGCACTGAGAGTGAAATAAAACAGTT
        CATGTTGGGAATGGGGCAAGAGAGGGAGATAAACAAGGGAGGTGACATCTACAGACCGGT
        TAGCTGAGATTACAGTACATTGGGGCTCCAAGTGCACAGAATCTGAACATCATGTTCATC
        [C,T]
        TAGGACAAGTGTTGCAGAGGCTTCCTGAAGAGGTTCATTCTGAGGCTTACCTTGAAGGAT
        CATCAGGAATTAATGATGAGTGTATTAAGCCATTCTCGCATTTCTATAAAGAAACGCCTG
        AAATTGAGTAATTTTTTTTTTTTTTTTTTTCTGAGACGGAGTCTTGCTTTCTTACCTA
        GGCTGGAGAGCAGTGGTGCGATCTCGGCTCACTGCAACCTCTGCCTCCCTGGGTTCAAGT
        GATTCTCCTGCCTCAGCCACCCGAGTAGCACAGGTGCCTGCCACCGGGTCCATCTAATTT

30920   GGCTTCCTGAAGAGGTTCATTCTGAGGCTTACCTTGAAGGATCATCAGGAATTAATGATG
        AGTGTATTAAGCCATTCTCGCATTTCTATAAAGAAACGCCTGAAATTGAGTAATTTTTTT
        TTTTTTTTTTTTTTTCTGAGACGGAGTCTTGCTTTCTTACCTAGGCTGGAGAGCAGTGGTG
        CGATCTCGGCTCACTGCAACCTCTGCCTCCCTGGGTTCAAGTGATTCTCCTGCCTCAGCC
        ACCCGAGTAGCACAGGTGCCTGCCACCGGGTCCATCTAATTTTTGTATTTTTAGTAGAGA
        [C,T]
        AGGGTTTCACCATGTTGGCCAGGCTGGTCTCAAACTCCCAACCTCGTGATCCTCCCGCCT
        TGGCCTCCCGAAGTGCTGGGATTACAGGCGTGAGCTGCCGCGCCCAGCCAAAATTGAGTA
        ATTTATAAGAAAAAAAGGTTTTATTAGCTCATGATTCTGCAGGCTGTACAGGAAGCGTGG
        TGGCATCTGCTTCTGTAGAGGCCTCAGGAAGCTCCAATCATGGTGGAAGGTGGAAGGCAC
        ATCACACTGTGAAAGCAGGAGCAAGAGTTGGGGGAACATGCCATAAGATCCCATCACTTT

31057   AGACGGAGTCTTGCTTTCTTACCTAGGCTGGAGAGCAGTGGTGCGATCTCGGCTCACTGC
        AACCTCTGCCTCCCTGGGTTCAAGTGATTCTCCTGCCTCAGCCACCCGAGTAGCACAGGT
        GCCTGCCACCGGGTCCATCTAATTTTTGTATTTTTAGTAGAGACAGGGTTTCACCATGTT
        GGCCAGGCTGGTCTCAAACTCCCAACCTCGTGATCCTCCCGCCTTGGCCTCCCGAAGTGC
        TGGGATTACAGGCGTGAGCTGCCGCGCCCAGCCAAAATTGAGTAATTTATAAGAAAAAAA
        [C,A,G]
        GTTTTATTAGCTCATGATTCTGCAGGCTGTACAGGAAGCGTGGTGGCATCTGCTTCTGTA
        GAGGCCTCAGGAAGCTCCAATCATGGTGGAAGGTGGAAGGCACATCACACTGTGAAAGCA
        GGAGCAAGAGTTGGGGGAACATGCCATAAGATCCCATCACTTTTAAAGAACCAGATCTCA
        TGTGAACTCAGAGCGAGAGCTCACTTATCACTAAGGAGATGGCCCAAGCCATTCATGAGA
        CATCAGCCTCCATGACCCAAACACGTCCCACCAGACTCCACCTCCAACATTGGGGATTAC

31097   GTGCGATCTCGGCTCACTGCAACCTCTGCCTCCCTGGGTTCAAGTGATTCTCCTGCCTCA
        GCCACCCGAGTAGCACAGGTGCCTGCCACCGGGTCCATCTAATTTTTGTATTTTTAGTAG
        AGACAGGGTTTCACCATGTTGGCCAGGCTGGTCTCAAACTCCCAACCTCGTGATCCTCCC
        GCCTTGGCCTCCCGAAGTGCTGGGATTACAGGCGTGAGCTGCCGCGCCCAGCCAAAATTG
        AGTAATTTATAAGAAAAAAGGTTTTATTAGCTCATGATTCTGCAGGCTGTACAGGAAGC
        [G,A]
        TGGTGGCATCTGCTTCTGTAGAGGCCTCAGGAAGCTCCAATCATGGTGGAAGGTGGAAGG
        CACATCACACTGTGAAAGCAGGAGCAAGAGTTGGGGGAACATGCCATAAGATCCCATCAC
        TTTTAAAGAACCAGATCTCATGTGAACTCAGAGCGAGAGCTCACTTATCACTAAGGAGAT
```

FIGURE 3U

```
              GGCCCAAGCCATTCATGAGACATCAGCCTCCATGACCCAAACACGTCCCACCAGACTCCA
              CCTCCAACATTGGGGATTACATTTCAATGAGATTTGGGTGGGGACAAATGTCCAAACTAT

31204         GTATTTTTAGTAGAGACAGGGTTTCACCATGTTGGCCAGGCTGGTCTCAAACTCCCAACC
              TCGTGATCCTCCCGCCTTGGCCTCCCGAAGTGCTGGGATTACAGGCGTGAGCTGCCGCGC
              CCAGCCAAAATTGAGTAATTTATAAGAAAAAAAGGTTTTATTAGCTCATGATTCTGCAGG
              CTGTACAGGAAGCGTGGTGGCATCTGCTTCTGTAGAGGCCTCAGGAAGCTCCAATCATGG
              TGGAAGGTGGAAGGCACATCACACTGTGAAAGCAGGAGCAAGAGTTGGGGGAACATGCCA
              [T,C]
              AAGATCCCATCACTTTTAAAGAACCAGATCTCATGTGAACTCAGAGCGAGAGCTCACTTA
              TCACTAAGGAGATGGCCCAAGCCATTCATGAGACATCAGCCTCCATGACCCAAACACGTC
              CCACCAGACTCCACCTCCAACATTGGGGATTACATTTCAATGAGATTTGGGTGGGGACAA
              ATGTCCAAACTATATTGATGAGTGAAAGCAAGAGTAAAGAACAGGGAAGGAATGATGGAG
              AGAATGAACCAGGTAGAGAAAATCTTCTAGGCATGAATGTTCAGCCCCTTTTCAGGGAGC

32660         CGTCAACCTCCTAGCTTCTGCAGACATTGGCAGGAATCACTGGGAGCAGCTGATGAATAT
              CACCCACTCCCTGGCCATACCCATTTCTCCAACCTCATCTTCCACTATCTGGATAGCTGG
              CTCCTCACTGCTTCTTGGTTTTGCTTTCCTACTTCTGTCTAGGATGCCCTCATATGACAT
              CTCACATTCTAAATCCTATCCATACTTCATGCCCAGCTTGGTTCTCTCTCTCTCTCTCTC
              CCCCACCCCCCCTCTCCGTGTGTGTGTGTGTGTGTGTGTGTGTGTGTGTGTGTGAGAG
              [T,A]
              GAGAGAGAGAGAGAGAGAGAGATGTTCTTCAATCTCACATCAGTTATACTGATATTTTGCCT
              TCAGTAAGATCCCCTAGCTCTTATTGCCTCTGTGCCCAGTAGATTAACACTTGGTTGTGT
              CTTTCTTTTTTCCCTTCCTTCCTGCCTGCCTTCCATCCTTCCTTCCTTCCTTTTCTTCCT
              CCCTTCCTTTCTTTTCCTTCCTTCCTTCCTTCCTTTCTTTCTGTTTCTTTTTTTTTTTTT
              TAGACAGAGTCTTCCTCTGTCACCCAGGATGGAGTGCAGTGGCATGATCTTGGCTCACTG

32875         GCTTGGTTCTCTCTCTCTCTCTCTCCCCCACCCCCCCTCTCCGTGTGTGTGTGTGTGTGT
              GTGTGTGTGTGTGTGTGTGAGAGAGAGAGAGAGAGAGAGAGAGAGATGTTCTTCAATCTC
              ACATCAGTTATACTGATATTTTGCCTTCAGTAAGATCCCCTAGCTCTTATTGCCTCTGTG
              CCCAGTAGATTAACACTTGGTTGTGTCTTTCTTTTTTCCCTTCCTTCCTGCCTGCCTTCC
              ATCCTTCCTTCCTTCCTTTTCTTCCTCCCTTCCTTTCTTTTCCTTCCTTCCTTCCTTCCT
              [T,-]
              TCTTTCTGTTTCTTTTTTTTTTTTTTTAGACAGAGTCTTCCTCTGTCACCCAGGATGGAGT
              GCAGTGGCATGATCTTGGCTCACTGCAACCTCCGCCTCCCGGGTTCAAGCGATTCTCCTG
              CCTCAGCCTCCCAAGTAGCTGGGATTACAGGCATGTGCCACCATGCCTAGCTGATTTTGT
              GTTTTTAATAGAGATGAGGTTTCACCATGTTTGTCAGGCTTGTCTTGAACTCCTGACCTC
              AAGCGATCCACCTGCCTCGGTCTCCCAAAGTAGTGGGATTACAGGCGTGAGCCACCGTGC

33477         TGGCCGCTTGTGTCATTCTTATTTTAGTTCTTTGGTTACTTCTTTAGATAAATCTGGACT
              CCTAATGCACACTCTGTAGTTCTCCCAAGAACTGGCTGTTTTGCTGCCTCCTTAATTTTG
              GCCGTATTGCGGGCCATACAGGAGGAACCTGACTTGCAGGCCTGAGTATCACTTTTACTA
              CCAAAAGTTTTAGTCAGTCACCATCTTTACTCAGATCCCAGTTGAACGGATCTGTCAGAA
              AAGAGACACTTGGCTAGGGTCTATATTAGTTGAGAGGCTATTTCCAATTCACTTCTCAGC
              [C,G]
              TGCATGGTTGTAGGAGCAAGAACTGGGATCAGTGAGCCACAGTGAACCTCATTACATGCC
              AGGCACTGAAAAAGTCAGATAAAACAGTCCATGCTAGCAATGGGGCAAAAGAGGGAGAAT
              TTGCAAGGGAATCTGTGGCCTAGAGGGCCCAAAATAGCAGTAGGGAAGGAGAGGAGGAAG
              AAAAAGAAGTGAGCCAGGGAGAAGAGCTTGACTGTAGTGGTGGTGGATGTTTCAGACCTG
              TGATATATGACCAATCATCATTTAAGTGGCTTTGGGCTGTGGTGAGCTTTCCCAGGGCCA

34059         GTGAGCTTTCCCAGGGCCAGAGAATAAGCCAGACCCATACCAAGTAATAGAACAGATGGG
              CAAAGAGTCTTCCACATTCTACTTGGAAAAGTAACTTGGTGGGAGAACAGAAGAGAATCC
              AGCAATAGAAGGTACAGATGTTAGTCTTCAGCAGCTCTACTCCCTGCCATTTCTCCAACG
```

FIGURE 3V

```
         CTCTGCAAACAGGAAGTGTGTTTCATAGCCATAGATCCACATCTTATTGAGTTTGTTTAT
         ATGCCAAGACCATGCTGAGCACTGTTCTCATCATACGTAGTTAGCGTCATATATAGTTCT
         [C,T]
         ACCACAGCCTATGGTTATCAGTATCCCACTTTACAGAGAAGGAAACTGACATTCACAGTA
         CCCAGCTGGTATAGTTGAACCTAGAATTGACCAGACTGTCCCCTCCAAAGCCTGGATTCT
         TATTCCAGGAGGGCCATCAGGAAAGCTGACAAACACAAAGCCATTTTCCAAGAGCCCTTG
         GGACTGAACAGGTCAAGGGTCCTCTGAAGATTGTCTGGATTCAGGATGCAAGGGTGGGAG
         TGGAGCATGTGCCCACAATCCACAGTGTGTTCTGTGGCTAGATCCTTGCCAAATGCAACC

36681    AAGGGTGGCCCTTTGTGTCATCTGCCCTGCACTCCCAGATTGGGCTGTGTGAATGCCAAG
         TGGGTTCCCTAAGCTTCCCTTGCCTTCATGTCAGAGAAGTCTTGGAGCAGGAGGGAAGAG
         GTACACCACCAGTACGATACCTCCTTTCTTTGCCTGCTTGTCCACTGGCATGGGGAGCCC
         AAAGTGACCATGTGACACTTGTAGATTCCAATTCACTGGAGCCCTTATCAAGTCCCCTGA
         TGAAAGCATCCCTGATCCCCTGGGAACCAAACCTTTTAATCTAGCCTAGATTGTAGAAAA
         [-,A]
         AAAAGAATAGAAATTAATCAAGTGAGTCACCAATTGCGTGATGGTGACAGGAGTCAATCT
         ACTTCCACCTAGTGGTTTCCAGACCTGTGTTTTAATGATAGGGACATGTATCAGTCATTA
         TTAAAGCATGTTACTGAATCCTGGAGGACAGCACCCCAACCCTGCAGGCTGCTGTCTCAT
         CTCTGGTGTCTTAGCTGAGTCATTCCATTGTTCTACTCATGTTGGCTGCTTCTGATGTTG
         AGGTATATGGTAAGATGAGGGGATCCCGTTGTCATGTGCCCATTGCACCACCTCCTTTAT

36821    CTCCTTTCTTTGCCTGCTTGTCCACTGGCATGGGGAGCCCAAAGTGACCATGTGACACTT
         GTAGATTCCAATTCACTGGAGCCCTTATCAAGTCCCCTGATGAAAGCATCCCTGATCCCC
         TGGGAACCAAACCTTTTAATCTAGCCTAGATTGTAGAAAAAAAAAGAATAGAAATTAATC
         AAGTGAGTCACCAATTGCGTGATGGTGACAGGAGTCAATCTACTTCCACCTAGTGGTTTC
         CAGACCTGTGTTTTAATGATAGGGACATGTATCAGTCATTATTAAAGCATGTTACTGAAT
         [C,T]
         CTGGAGGACAGCACCCCAACCCTGCAGGCTGCTGTCTCATCTCTGGTGTCTTAGCTGAGT
         CATTCCATTGTTCTACTCATGTTGGCTGCTTCTGATGTTGAGGTATATGGTAAGATGAGG
         GGATCCCGTTGTCATGTGCCCATTGCACCACCTCCTTTATCAAAAAAGTGGTCCTTGAGG
         CAATGTTTGAGATATCATGACAGTGAGTCAGTTATTCTCTATGTCTTAGTGTGCTTGTAT
         GGAAAGACACATTGCAGGCAGAAAAGGCAAACCCATACCCTGAGATATCAATTCCAATAA

38079    TAGAATGTCAAGATGATCAAGGTCCTTTTGGATTATATTGTGATATAGAGAAGGAGATTT
         AAGATTGTTTTGGGGCAATAGAGTAAATGAGAATCGCTCTCCATCCCAGAGAAATGTGAA
         CTGCTTTTGATCCTCCTTTCTGATGGAAATTTAGAAGAATGAATTTGCCAAATCAATAGC
         TGCATATCAAATGCCAGAGGCTGCCAGTAAAGATACCACATCCAATATGGCAGCTACAAC
         TGAGACTAGCAGTAGTCCACCATCATTCTCCATTATCCATCTGCTCTTTTTCAGAAGTGT
         [A,G]
         ATGGTAACTTAAATGAGATTATGATGGAGCCCATTACACTTGCATCCCAAAATTTTTTGA
         TGGTGACACTGATGTCTGCCATTCCTCATGTGGATTGCTCATGATTTATTAACATGGCCA
         GAAAGAGGTTTCCTCTTTCTCCCATAATGGTTGTTACTTCACAGGTCTAAGACCTCCACA
         GAGGTCTAAGTATATTGATCCCAAATATGTACTTAGAGGTTGGGAGAATAATTCCAAGGT
         GGGAACCATTATGTGATAGACTTTGGCCAGGACTCCCTTTATCATATGGTTTCCATAACC

38432    TTTTTTGATGGTGACACTGATGTCTGCCATTCCTCATGTGGATTGCTCATGATTTATTAA
         CATGGCCAGAAAGAGGTTTCCTCTTTCTCCCATAATGGTTGTTACTTCACAGGTCTAAGA
         CCTCCACAGAGGTCTAAGTATATTGATCCCAAATATGTACTTAGAGGTTGGGAGAATAAT
         TCCAAGGTGGGAACCATTATGTGATAGACTTTGGCCAGGACTCCCTTTATCATATGGTTT
         CCATAACCCCTCATCTACGTACAAAGCCATAATGGTATCCGGTTCTGAAAAATTCTGGGT
         [A,T]
         TGTACATCATATATACTTGTGAAAGCAAGGCCTTTCCTCAAGACCAGTCCTCCTTTTCAT
         TGTGCACTGGATCTGTAAATTGACTTAGCTCTGGAAGCTGATGAAGAGACCGTGATTTTC
         CCATTGTGACAG
```

FIGURE 3W

SEQUENCE LISTING

```
<160> NUMBER OF SEQ ID NOS: 6

<210> SEQ ID NO 1
<211> LENGTH: 1544
<212> TYPE: DNA
<213> ORGANISM: Human

<400> SEQUENCE: 1
ctaccacgtt cactgccttc ctctcactaa agccgagagg gaggctgctc agctctcagg      60
aaaactcttt tgaaccctgg gcacctgctg tcctcagttg gcatctccca ccctctgagc     120
ctcttctgtt cctgcacaac ctgcctcttc gctgagatgt agacgtgagc ccccgtggac     180
gatgactgca gtgtatatga atggaggtgg cctggtgaac ccccactatg cccggtggga     240
tcggcgcgac agtgtagaaa gtggctgtca gaccgagagt agcaaggagg gtgaggaggg     300
acagccccgc cagctgacgc ccttcgagaa actgacacag gacatgtccc aggatgagaa     360
ggtggtgagg gagatcacgc tggggaaacg gataggcttc taccgaattc gaggggaaat     420
cggaagtgga aacttctccc aagtgaagct tgggattcac tccctaacca aagaaaaggt     480
ggccattaag atcctggaca agaccaagtt agaccagaaa acccagaggc tactatcccg     540
agaaatctcc agcatggaaa agctgcacca tcccaacatc atccgccttt acgaagtggt     600
ggagaccctc tccaagctgc acttggtgat ggagtatgca gggggtgggg agctcttcgg     660
aaaaattagc actgagggga agctctctga accagaaagc aagctcatct tctcccagat     720
tgtgtctgcc gtgaagcaca tgcatgaaaa ccaaattatt catagagatc tgaaagcaga     780
aaatgtattc tataccagta atacttgtgt gaaggtgggc gattttggat tcagcacagt     840
aagcaaaaaa ggtgaaatgc tgaacacttt ctgtgggtct cctccctacg ctgcgcctga     900
actcttccgg gacgagcact acatcggcat ttacgtggat atctgggcct tggggggtgct     960 tttgtacttc atggtgactg gcaccatgcc atttcgggca gaaaccgtgg ccaaactaaa    1020
aaagagcatc ctcgagggca catacagtgt accgccgcac gtgtcagagc cctgccaccg    1080
actcatccga ggagtccttc agcagatccc cacggagagg tacggaatcg actgcatcat    1140
gaatgatgaa tggatgcaag gggtgccata ccctacacct ttggaacctt tccaactgga    1200
tcccaaacat ttgtcggaaa ccagcactct caaggaagaa gaaatgagg tcaaaagcac     1260 tttagaacat ttgggcatta cagaagagca tattcgaaat aaccaaggga gagatgctcg    1320
cagctcaatc acagggtct atagaattat tttacataga gtccaaagga agaaggcttt     1380
```

```
ggaaagtgtc ccagtcatga tgctaccaga ccctaaagaa agagacctca aaaagggtc    1440 ccgtgtctac agagggataa gacacacatc caaattttgc tcgattttat aaattgcact   1500
agactgcttg taactaacca agatgattgt tgctgcttct aaat                   1544
```

<210> SEQ ID NO 2
<211> LENGTH: 436
<212> TYPE: PRT
<213> ORGANISM: Human

<400> SEQUENCE: 2

```
Met Thr Ala Val Tyr Met Asn Gly Gly Leu Val Asn Pro His Tyr
 1               5                  10                  15

Ala Arg Trp Asp Arg Asp Ser Val Glu Ser Gly Cys Gln Thr Glu
                20                  25                  30

Ser Ser Lys Glu Gly Glu Glu Gly Gln Pro Arg Gln Leu Thr Pro Phe
            35                  40                  45

Glu Lys Leu Thr Gln Asp Met Ser Gln Asp Glu Lys Val Val Arg Glu
        50                  55                  60

Ile Thr Leu Gly Lys Arg Ile Gly Phe Tyr Arg Ile Arg Gly Glu Ile
65                  70                  75                  80

Gly Ser Gly Asn Phe Ser Gln Val Lys Leu Gly Ile His Ser Leu Thr
                85                  90                  95

Lys Glu Lys Val Ala Ile Lys Ile Leu Asp Lys Thr Lys Leu Asp Gln
            100                 105                 110

Lys Thr Gln Arg Leu Leu Ser Arg Glu Ile Ser Ser Met Glu Lys Leu
        115                 120                 125

His His Pro Asn Ile Ile Arg Leu Tyr Glu Val Val Glu Thr Leu Ser
    130                 135                 140

Lys Leu His Leu Val Met Glu Tyr Ala Gly Gly Gly Glu Leu Phe Gly
145                 150                 155                 160

Lys Ile Ser Thr Glu Gly Lys Leu Ser Glu Pro Glu Ser Lys Leu Ile
                165                 170                 175

Phe Ser Gln Ile Val Ser Ala Val Lys His Met His Glu Asn Gln Ile
            180                 185                 190

Ile His Arg Asp Leu Lys Ala Glu Asn Val Phe Tyr Thr Ser Asn Thr
        195                 200                 205

Cys Val Lys Val Gly Asp Phe Gly Phe Ser Thr Val Ser Lys Lys Gly
    210                 215                 220

Glu Met Leu Asn Thr Phe Cys Gly Ser Pro Pro Tyr Ala Ala Pro Glu
225                 230                 235                 240

Leu Phe Arg Asp Glu His Tyr Ile Gly Ile Tyr Val Asp Ile Trp Ala
                245                 250                 255

Leu Gly Val Leu Leu Tyr Phe Val Thr Gly Thr Met Pro Phe Arg
            260                 265                 270

Ala Glu Thr Val Ala Lys Leu Lys Ser Ile Leu Glu Gly Thr Tyr
        275                 280                 285

Ser Val Pro Pro His Val Ser Glu Pro Cys His Arg Leu Ile Arg Gly
    290                 295                 300

Val Leu Gln Gln Ile Pro Thr Leu Arg Tyr Gly Ile Asp Cys Ile Met
305                 310                 315                 320

Asn Asp Glu Trp Met Gln Gly Val Pro Tyr Pro Thr Pro Leu Glu Pro
                325                 330                 335

Phe Gln Leu Asp Pro Lys His Leu Ser Glu Thr Ser Thr Leu Lys Glu
            340                 345                 350
```

```
Glu Glu Asn Glu Val Lys Ser Thr Leu Glu His Leu Gly Ile Thr Glu
            355                 360                 365

Glu His Ile Arg Asn Asn Gln Gly Arg Asp Ala Arg Ser Ser Ile Thr
    370                 375                 380

Gly Val Tyr Arg Ile Ile Leu His Arg Val Gln Arg Lys Lys Ala Leu
385                 390                 395                 400

Glu Ser Val Pro Val Met Met Leu Pro Asp Pro Lys Glu Arg Asp Leu
                405                 410                 415

Lys Lys Gly Ser Arg Val Tyr Arg Gly Ile Arg His Thr Ser Lys Phe
            420                 425                 430

Cys Ser Ile Leu
        435

<210> SEQ ID NO 3
<211> LENGTH: 38564
<212> TYPE: DNA
<213> ORGANISM: Human
<220> FEATURE:
<221> NAME/KEY: misc_feature
<222> LOCATION: (1)...(38564)
<223> OTHER INFORMATION: n = A,T,C or G

<400> SEQUENCE: 3
aaagcacaag ttcctgccca cctggtgctt ttttttttt tcagatggcg tttcactctt      60
gtcgcccacg ctggagtgca atggcatgat ctcagctcac tgcaccctct gcctcctggg    120
ttcaaacaat tctcctgcct cagcctccca gtagctggga ttacaggtg tgcgccacca    180
tgcttggcta attttgtat tttagtaga gatggagttt caccatgttg gccaggctgg    240
tctcaaactc ctaacctcag gtgatccacc cacctcagcc tcccaaagtg ttgggattac    300
aggcttgagc cactgtgccc ggcgccctcc tagtgctgat gtagttgtgg cccaagtaca    360
ttagtgacaa ggacagcaca gtaatgagga cacagagcca gtaagttctt cagagagtct    420
gttagaacac aaagtgatca agtgatcaa agtactgca ttctatggaa atctatatt    480
tttctttttc cttaggttaa gctaaagttt cttgcagaat tactacttca ttctagtctg    540
tcataagctg catggtgttt ttctgccagg aatctgggga gatctagtgc cacttgacct    600
tcacagagat tcttaacctg atgggtttca gaatgtcatc ttaaaattgg atgcaaattg    660
tatgggtgag ggtttttttt ttttcctcc tggggataaa gtcataggtt ttgttagcat    720
ctcaaaggag tctgtgagcc caggatgatt aagaatcagt gattttggct gagtacagtg    780
gttcacacct gtaattccag cactttggga ggtagaggtg ggtaaagaaa aggaagaaga    840
atcagtgact tagattttct tcactctaat taaggacctt tacctttttt gtttgtttgc    900
tttgctttgt tttttgaga cagggtccgg cattgtcacc caggctggag tacagtggct    960
tgatctcagc tcactgcaac ctccacttcc tgggctcaag ccatcctccc acctcagtct   1020
gtaggtgtag ctgagactac aggtgcacac cctgctaagg ggtacaccac cacaccctgc   1080
taggaggtac aacaccacac cctgctaagg ggaactttat acttaaaaat gtttttaaaa   1140
aacatcctaa ttggtctcta acctagagat gtgcttagtt actgatacct ggtccctttt   1200
aagcctatgt tcgtcatcct tcttccagat tcctttctct ctatccagaa ataggagcag   1260
tactgggcat caacctcctc tttacttccc ttatttatgt ttatttggca accccatact   1320
taaccttaag tataagctta ggaagcctta tttatactta attgtaataa tgtgatatta   1380
ttgagcagag ttggaaatcc atacttccaa ggcagtctct catgttttca gtcaaatttt   1440
```

```
tggtttggaa tgctcaagtc caaaaatcaa gtttaacaca tatttactta gtaaacacttt    1500
tctatatgta agaacttata ctccattttg aaggagagag gaggtgagca ggacatacct    1560
acaagtcaaa accagttccc accttcactg agatgggaca ttttggaaaa tgcacgaagt    1620
gctgtgggaa ttcagagagg aagagagtat ttcctgctgg agagtgcaga aaaaaaacat    1680
cccgatgaca tcgtaggtgg gcagcatttc ttgtcactgg caatgctgta aaccctcctt    1740
ttccacatct tcaaaataag gtgctgggcc tagaaactga cacctgctca gaaaaattca    1800
aaaagtgaat gtaggaggaa aaatcagcct ttgtcataaa atgacatagg aagaaagagt    1860
ggaagcaact agtataggac aagttgtgca agaacatgaa gtagtaaagg agataaaata    1920
ttattatttg aataaatatg agaaattttg aaaaccatta gtaatccgga atctttcatc    1980
tttgctatca tattatttt aaaatttggt tttaaagcaa cacaaggcaa tgtgcatatt    2040
ttcttaaact ttaagaaata gaaaaattgt tttgctagaa atatgtacgg accttagggg    2100
ctttctaaa atgtaggttg agaggtgtgt gtatatgctc ttttcttctt actagatcac    2160
atgtaatcaa gcatctacta ctgatatgag tcataaattt gtggggtact tttagatcaa    2220
tgcttacaaa gcagttgcac attcattaca aatcctgtac agtacattag cataagctaa    2280
taaatttctt actctctatt cttaggttga accagccaaa ttttcgagac agctcacggc    2340
ttagaggaag gttcatctaa ataaaggccg gctaaagtga cattgcaggg attaaatcct    2400
tctttggctg cctgtgtgac cagaaggctt atttgcaagt ttcttctttc ctggggtcca    2460
gattattagg tctccagcgc cctgcagctt gacagaaaga gaagcatgaa atgaaggtca    2520
gagatgagat cccgcagcag ggacgtgggg gcctcccagg ggcatttacg caccagagtg    2580
caagattctc tggccatcaa gggaaatagc aaacagaagc ctttgtcctg ggcacagcc    2640
acctaccaca aagcatcaga ctccacgtct ggccagaaag ttcctggagt cccatcaggc    2700
cagtgggtat gtaacatgtg cctaattgta cagctagagc ctgcaagttc aacgtgaggg    2760
aaggtgggaa atgtcttgag tgaggcgagc agctcctggc tgggctgggc agactcagct    2820
accacgttca ctgccttcct ctcactaaag ccgagaggga ggctgctcag ctctcaggaa    2880
aactcttttg aaccctgggc acctgctgtc ctcagttggc atctcccacc ctctgagcct    2940
cttctgctcc tgcacaacct gcctcttcgc tgagatggag acgtgagccc ccgtggacga    3000
tgactgcagt gtatatgaat ggaggtggcc tggtgaaccc ccattatgcc cggtgggatc    3060
ggcgcgacag tgtagaaagt ggctgtcaga ccgagagtag caaggagggt gaggagggac    3120
agccccgcca gctgacgccc ttcgagaaac tgacacagga catgtcccag gatgagaagg    3180
tggtgaggga gatcacgctg gggaaacgga taggcttcta ccgaattcga ggggaaatcg    3240
gaagtggaaa cttctcccaa gtgaagcttg ggattcactc cataaccaaa ggtaggatcc    3300
gacttcccaa gggtcatccc tggcagtatt gggacctagt gtaggaaagg ggttaggtgg    3360
ccagggccaa ggaagcaagt aaagtgacct cagcagagcc cctgcaaggc ccacatcctg    3420
tgccagccgc cttctgtggt cttctcagtt aattttcaca gtaaccatgt gaggtcaata    3480
tttttttcca ttttgcagat aaagaaactg agatccaaag aaggcaaatg tgtcttcagt    3540
tcnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
```

-continued

```
nnnnnnnnnn nnnnnnnnnn nnnnnnnnnn nnnnnnnnnn nnnnnnnnnn nnnnnnnnnn      3900
nnnnnnnnnn nnnnnnnnnn nnnnnnnnnn nnnnnnnnnn nnnnnnnnnn nnnnnnnnnn      3960
nnnnnnnnnn nnnnnnnnnn nnnnnnnnnn nnnnnnnnnn nnnnnnnnnn nnnnnnnnnn      4020
nnnnnnnnnn nnnnnnnnnn nnnnnnnnnn nnnnnnnnnn nnnnnnnnnn nnnnnnnnnn      4080
nnnnnnnnnn nnnnnnnnnn nnnnnnnnnn nnnnnnnnnn nnnnnnnnnn nnnnnnnnnn      4140
nnnnnnnnnn nnnnnnnnnn nnnnnnnnnn nnnnnnnnnn nnnnnnnnnn nnnnnnnnnn      4200
nnnnnnnnnn nnnnnnnnnn nnnnnnnnnn nnnnnnnnnn nnnnnnnnnn nnnnnnnnnn      4260
nnnnnnnnnn nnnnnnnnnn nnnnnnnnnn nnnnnnnnnn nnnnnnnnnn nnnnnnnnnn      4320
nnnnnnnnnn nnnnnnnnnn nnnnnnnnnn nnnnnnnnnn nnnnnnnnnn nnnnnnnnnn      4380
nnnnnnnnnn nnnnnnnnnn nnnnnnnnnn nnnnnnnnnn nnnnnnnnnn nnnnnnnnnn      4440
nnnnnnnnnn nnnnnnnnnn nnnnnnnnnn nnnnnnnnnn nnnnnnnnnn nnnnnnnnnn      4500
nnnnnnnnnn nnnnnnnnnn nnnnnnnnnn nnnnnnnnnn nnnnnnnnnn nnnnnnnnnn      4560
nnnnnnnnnn nnnnnnnnnn nnnnnnnnnn nnnnnnnnnn nnnnnnnnnn nnnnnnnnnn      4620
nnnnnnnnnn nnnnnnnnnn nnnnnnnnnn nnnnnnnnnn nnnnnnnnnn nnnnnnnnnn      4680
nnnnnnnnnn nnnnnnnnnn nnnnnnnnnn nnnnnnnnnn nnnnnnnnnn nnnnnnnnnn      4740
nnnnnnnnnn nnnnnnnnnn nnnnnnnnnn nnnnnnnnnn nnnnnnnnnn nnnnnnnnnn      4800
nnnnnnnnnn nnnnnnnnnn nnnnnnnnnn nnnnnnnnnn nnnnnnnnnn nnnnnnnnnn      4860
nnnnnnnnnn nnnnnnnnnn nnnnnnnnnn nnnnnnnnnn nnnnnnnnnn nnnnnnnnnn      4920
nnnnnnnnnn nnnnnnnnnn nnnnnnnnnn nnnnnnnnnn nnnnnnnnnn nnnnnnnnnn      4980
nnnnnnnnnn nnnnnnnnnn nnnnnnnnnn nnnnnnnnnn nnnnnnnnnn nnnnnnnnnn      5040
nnnnnnnnnn nnnnnnnnnn nnnnnnnnnn nnnnnnnnnn nnnnnnnnnn nnnnnnnnnn      5100
nnnnnnnnnn nnnnnnnnnn nnnnnnnnnn nnnnnnnnnn nnnnnnnnnn nnnnnnnnnn      5160
nnnnnnnnnn nnnnnnnnnn nnnnnnnnnn nnnnnnnnnn nnnnnnnnnn nnnnnnnnnn      5220
nnnnnnnnnn nnnnnnnnnn nnnnnnnnnn nnnnnnnnnn nnnnnnnnnn nnnnnnnnnn      5280
nnnnnnnnnn nnnnnnnnnn nnnnnnnnnn nnnnnnnnnn nnnnnnnnnn nnnnnnnnnn      5340
nnnnnnnnnn nnnnnnnnnn nnnnnnnnnn nnnnnnnnnn nnnnnnnnnn nnnnnnnnnn      5400
nnnnnnnnnn nnnnnnnnnn nnnnnnnnnn nnnnnnnnnn nnnnnnnnnn nnnnnnnnnn      5460
nnnnnnnnnn nnnnnnnnnn nnnnnnnnnn nnnnnnnnnn nnnnnnnnnn nnnnnnnnnn      5520
nnnnnnnnnn nnnnnnnnnn nnnnnnnnnn nnnnnnnnnn nnnnnnnnnn nnnnnnnnnn      5580
nnnnnnnnnn nnnnnnnnnn nnnnnnnnnn nnnnnnnnnn nnnnnnnnnn nnnnnnnnnn      5640
nnnnnnnnnn nnnnnnnnnn nnnnnnnnnn nnnnnnnnnn nnnnnnnnnn nnnnnnnnnn      5700
nnnnnnnnnn nnnnnnnnnn nnnnnnnnnn nnnnnnnnnn nnnnnnnnnn nnnnnnnnnn      5760
nnnnnnnnnn nnnnnnnnnn nnnnnnnnnn nnnnnnnnnn nnnnnnnnnn nnnnnnnnnn      5820
nnnnnnnnnn nnnnnnnnnn nnnnnnnnnn nnnnnnnnnn nnnnnnnnnn nnnnnnnnnn      5880
nnnnnnnnnn nnnnnnnnnn nnnnnnnnnn nnnnnnnnnn nnnnnnnnnn nnnnnnnnnn      5940
nnnnnnnnnn nnnnnnnnnn nnnnnnnnnn nnnnnnnnnn nnnnnnnnnn nnnnnnnnnn      6000
nnnnnnnnnn nnnnnnnnnn nnnnnnnnnn nnnnnnnnnn nnnnnnnnnn nnnnnnnnnn      6060
nnnnnnnnnn nnnnnnnnnn nnnnnnnnnn nnnnnnnnnn nnnnnnnnnn nnnnnnnnnn      6120
nnnnnttgac acataaaata aaccatcaga gttggtaact gattggatgt agaactgaag      6180
```

-continued

```
atggaaggat ggacgaaggc aatgaccttg ctttagttga ctatgtgaac caaaacaggt    6240
gatgccttta ataggaatag gagaaagagc aaatttggga gggaaaaagt tgagtgaaaa    6300
cactgacatc cagaaggagc tgtctactgg gcatgctcca gtcatggaca agggcatgag    6360
gtcagaccag gtatttgcat tgagaagatt gtagaaatgg atgcagtcac tgaaggagac    6420
tgtggagaag ggtgatgagc aaccttttta cacttagtaa ctagttctac atcctagttg    6480
acattttatg tatggattag tttttttttt tttttttttt tgagatggag tctcgctctg    6540
ttgcccacgc tggagtgtag tggtgtgatc ttggctcact gcaagctctg cctcctgggt    6600
tcatgccgtt ctcctgcctc aacctcccga ggagctggga ctacagacac ccaccaccac    6660
gcctggctaa ttttttgtat tttagtaga cgggtttt caccatgtta gccaggatgg    6720
tctcgatctc ctgacctcgt gatctgcccg cctcggcctc ccaaagtgct gggattacag    6780
gcatgagcca ccgcgcctgg ccggattagt tttaaatatg ctaatggaat cattcactgt    6840
tgctccatga acactatgat ttttcaatgt cattaaatat agatttttaa aatatattta    6900
tgtgtatata ttatctatat atgtgtattt attatctata ctctcatctt ttaaagagga    6960
catattgttt cacatatagc tgtggcataa attctttaac ttagccacta ttggttaaca    7020
tttggatcat ttctaaagtt ttgctcttaa ttataatgct acagagatta ttctttccca    7080
tacttctttg catatacgta tgatttctct cagcatacat tcctagaagt tagctgtctt    7140
ggtcagaggg catgcattga aaaattttaa cacacagcac caaaagagca gcttttgaat    7200
ccttactcat agagtacatc tatctgtaac tcaaatctca cagggactaa tgttgctttt    7260
caatagtcta gagccagcat gaaagacaaa agatgaaaca catagagcga tgaaaggcca    7320
aaaatcgaga cagaagatgt gatttggaag gttacaagag aagttggata aagccaaaca    7380
aggaaaggaa tttagaaaaa agtgtccaat gctgcagaag ggtcacagag ctacagtctg    7440
agcaaaggct actgcataag gccaactttg agaagtttca tacaagtgtg ggttcagatg    7500
ttagattcca atagaaagga agcaggatgg gacagtagga aaagcgtgga cttggggacc    7560
agacaaattt atctgaaata ctcattcagt aacttactag gcttctgact ttaggcatat    7620
taatctcttt ggtcctcagt tgcctcagct gtaaaataga gataatgatt tttagaattg    7680
ttggggaaat tggaaataat atatgtgaag tacatgacat atagtaacca ctcaaaatgg    7740
tagctgccat tgctataact ttactttta attaatctta tttcaaaaag gtatttaatg    7800
ttattacaac aataaaaacc agtatacttt actatgaata aaggtgatg gtaaaaataa    7860
atacaatgca aacaaattaa aaagcattaa aggaaaatta caagtaacaa agtaattttt    7920
aaaacatgct aacaatcaat ctcagacttt ctctttgcct taattaggag aattaaagga    7980
gagctgaaat gggaatcatg ttttttacgct gtgattcagt gctatttaag gctgtttcca    8040
cgccctaaaa tcatttcaac ctcatgagtc ttaaaggttc cactttggga agcactgaca    8100
tcatctagtc cttccatgtt ttacaaacga ggagatggag gctcagaaga ggctgtccca    8160
aggtttagaa cctgttttaca ggaattcaca tggaattgag tactcacatg tattgagtac    8220
agggaattc tatggaccca cagcagggaa gtagggccgg gtcttaagat gatattcttt    8280
tgatcttcac tttctctggg gctgtgtgct ttctcatttc tacttttctt gatgaatttg    8340
ttccatcttt atacctcttt ctgcaaaaag gttttccaca cttaattatc agaaggtata    8400
tcatggccaa aaatggttgt tgccagtccc acatctacat aaactctcaa tgttattgac    8460
cgcctccatc ccatgtgttt cattctgttt cagttcaaat tttaaaaaga aagaatatac    8520
ttaattacta gccagctgaa aatgaactac ctttgagtca agggcatgcc cgtgtcagtg    8580
```

-continued

```
agctgtaacc ctttgagtca cgtgggccac tactgtctca gcagagccaa aggtccaaag   8640
aagtctctgg gaagggagaa aattgacaga catatccacc atagagacat tagctagcta   8700
agccgagaag tttctacaag ccgggagcaa gacagtgccc aattctgtag acaggatatt   8760
atgtgaaagg acaaaaaaaa aagtggaat aataattagt gtttatatac tgacttactt   8820
ctcgggttcc aaagacttct tgtctgttgt attacaaaat taacttcaaa cttgtcccca   8880
tgagtttcag agagcatggc attttcccac tgtgtgggtg tgggtgggtg ccttgtgtgg   8940
cctcactgac atgccctcct tatacctaac ctgctacaaa gtagctctat tgtcaaagaa   9000
acagtctcac ccgctggttc tgggacagta tgtgcaaaaa gggacaggaa ataaatagc    9060 agtttgtaca aatatggccc ccacaccaaa ccaacttgcc cagaattgtc atccggtttt   9120
ctaggaatat aaggacagtt tgaataagat aatagaggag attcccagga agcagagag    9180 tttcagtgcc aggagcagct cccaggacag tagtctaaaa aattgaaaaa aaaaaaaata   9240
aagaaataca aagcaccaag tgctctggat ctctacaaag gaggctccaa tatgggtccc   9300
tgctggctgg ggtttatttt tatagctcac agtttggaat tcccttgggc tctccaagct   9360
gatagtgaag gttgacagtc atcatgagcc ccttttaggc ctgattagaa atttctcata   9420
agagatgata cacttagctt ctgaatattt tatgtcccat ctgttgtcac aaacaaaaga   9480
agtggcagcg aatgtgggtg ttttttttctg ttgctgccct tctgacttct tccttctgct   9540
actctagtct catgtttcta ggatcctttc ttcctcccac tttatttatc tatttatcta   9600
ttaattcatt cttttccttcc ttccttttttt tttttttat cttttgagga agagttttgc   9660
ttcattgccc aggctggagt gcagtgatgc gatcaaagct cactgctgcc ttggactcct   9720
gggctcaagt gattcaccca cctcagcctc ccaaagcact gggcattaca ggtgtgagac   9780
accatgactg gccttcattc ctttatatat atatataata taatatataa tgtaatatat   9840
aatataatat ataatataat atatgtgtgt gtgtgtgtgt gtgtgtgtgt gtgtgtgtaa   9900
gcacatgcct gataaggaac ttacagcagt ttaacagagg cagacaggaa aaaattgatg   9960
agtgctgtcc agagtaaggc agcaagaatg tgcttacctg tgccccgtgg atccaggaag  10020
ggtctattga gcaggaaaag cttgcaatgg gtcttgaggt ctgaggagca atttcacagg  10080
agaaggagga aagagaactc cagaaagaga gataggatat aaagtacatg gaagcatgaa  10140
ccagtgtggg gagtatttgg agatttaaaa gtaattcagc aaagctagag catgaggtgc  10200
acccacagag tcatgggaaa gagataaggt ggatggggct tgatcatgga aaatcttctt  10260
gcatatctgg attttgtcat ttaggtattg gaaagctact gaagagtttt tttttttttt  10320
gagacggagt cttgccctgt cacccagcct ggagtacaat ggtgtgatct ctgttcattg  10380
aaacctctgc ctcctgggtt caagtgattc tcctgcctca gtctcctgag tagctgggat  10440
tacaggcaca cgccaccatg ctcggcaatt ttttttttgta tctttagtag atgggggtt   10500 tcaccatctt ggccaggctg gtctcgaatt cctgacctcg tgatccgccc gcctcagcct  10560
cccaaagtgc tgggattaca ggcatgagcc actgcgctca gtcgtttagg agctttaagc  10620
aagccattaa tgcaagtgat taatatgatc ttatttcagt gcggaatgtg aattgaagtt  10680
ggaaagtaag gagagtcaag gaagtcagaa aaaaatgtta gtcaaatggt ccagatggat  10740
gatgttgttc atctcaacta aggagaagtg gcagtgagaa tggagagaag agcatgtatt  10800
tgaaaaatgt cttaggatat tgaaaaacct tgtgatcaat ggtatgggtg agagcaggac  10860
gggacatggg agaggaagaa ttgacgatga ctcccagttt ccagttttaa tgccttacca  10920
```

```
gtaaataatt acaggagaag tggatttgag agtaaatata tggaagcact gacttggagg    10980
tatatggaat tcatgaaatg aatgggtcta gcagctttct tggagcccaa gagaaagtat    11040
gatacataaa gatttgaggc ttaacaaact ctgggatgta gtgacatctt gggagtccta    11100
gttacaagct ccttggtgtc agatactata tcacattgat ccttaaagtt cctccatgtg    11160
tgttataaat aataaacact cgacaaatat ttggtgagtt aagttagtat aacttctcat    11220
gaaaatccag gagtggtgga ggaagaaata ttcgagggag caatgcatag cagcaccttc    11280
tggtaggtgc tgtatgctgt gatctccctg gaggacaggg ctagagcacg aactcagtct    11340
gtagcagagc ttcataaaga tagcccaatg gttttgtcgt tttgcttttt ctagagatga    11400
agtctcaact atggttatcc aggccgttca agaacttctg ggctcaagca atcctcctgc    11460
ctcagtttcc taagtagcat gggggacagc tatgcaccac tgcacctgac tgctcactgg    11520 tttttaaaaat tgattccccc ctcttgaata cattcattaa aatagcaatt caaaattgta    11580
ttttcttact ttaaaaatgg ttagttagtg atttagggaa ttcaccctaa aaataaatca    11640
tatattggaa atactacaac caaaaaaatg ttcattgtcg tgttatttat agtgtcgaga    11700
actagtaata acttatggga tccaatgata taggaatggt caggtaaagc atatacactg    11760
ggcagaagat tccatagcca tgagaaatca tgattatgaa gactctgtgg taacatggaa    11820
gatgggcagg acatgagtgt aagtgaaaag ccaggtgcaa atggagcgca cactattatg    11880
ataatactta ctccaggttc ttcagtgaga ttattcactc agcaaatact tgttgagcac    11940
ctactatgca atagccacta ttctagagac tggtgataca gcagtgaaca aaatagacag    12000
caatctctgt ccttatggaa cttacactct agtgagaggg aagccagaca aaataaatg    12060 tgtaaaatat tcattgtatt atgtagcgat aagtgataag aaagaaaaga gggccgggcg    12120
cggtcggtca cgcctgtaat cccagcactt gggaggcca aggtgggtgg attatgagat    12180
caagagatgg aggccatcct ggccgacatg gtgaaaccac aattctacta aaaatacaaa    12240
aattagctgg gcatggtggt gtgcaccttt agtctcagct actcaggaga ctgaggcagg    12300
aaaatcgctt gaacccagga gggggaggtg gcagtgagcc aagatcgtgc cactgtactc    12360
cagcctggtg acagagccag actctgtctc aaaaaaaaaa aagaaagaaa gaaagaaaga    12420
aagaaagaaa gaaagagcag gaggggagat agaaagcatt gaggatgaca gttttttagat    12480 aagttggcca ggacagcctt actgaggagg taataattaa actgaaagaa atgagggaaa    12540
tggctataca tggggaact ccatcaagca gaaggcgtag caggcgtaag agtgtccaga    12600
tgggagatgc ctgcagtact cttgaaacag ctgagggaa agggcagaga gtaacaggga    12660
acagattgtg gaggaccaag tttgtcaaag taagaagttt ggcttttcct gggattttac    12720
aggagccatc agaaggaact ggggatttca caagggaac cagggatttc ctgggatttc    12780
acaggagcca tcagagggaa ctgggggagt gacatgatct ggcttannnn nnnnnnnnnn    12840
nnnnnnnnnn nnnnnnnnnn nnnnnnnnnn nnnnncttg ggcaacatag caagaccctg    12900
tctttaaaac caaaaccaaa accaaaaaaa ccacacacat ataacctttt tatgtttaac    12960
gcatatcaat accaaaaaag tttaaaaatc atgagtattc attttgatga attttccaaa    13020
ctgaaaagac cctgaaagc accaccaaca tcaagacaca gaacacttct ggtactcaga    13080
gcgctgccct ccacctgctc gtcatcctcc attctattct ctacatcctg aagtgtaacc    13140
actattctga cttctaatac catagattgc ttttgactgt tttaaacttt acataaatgg    13200
catcatccaa tgtgtattct tttgtcttac ttcaattgtc caattttgag tttgtgacta    13260
ccatccatac tgttttatgt agttcagatg tttcatgctc attgccatat atacagtaat    13320
```

```
tcattgtatg aatgtagtac cacaatttat ttatccattc aactgttgct gatgtgacta    13380
gtttctagtt tccagtttgg ggctattatg aataacattg atgtgaacat tctagtgcaa    13440
gcgttttttgg taaactttt tttttttttt gaggcagggt tttgctttgt cacccaggct    13500
ggaatgtggt ggcacaatca cagctcactg caaccttgac tttctgtatt tgagtgatcc    13560
tccaacctca gcctctggag tagctggaac cacagggca tgccatcatg cctggctaat    13620
tttttaaatg ttttgtagat atggggtcct gctatgttgc ccagactggt ctcaaactcc    13680
agggctcgag taatcctctt gccttggcct cccagagtgt tggtattaca gatgtgagcc    13740
actgagtctg gctcgtatgc attttattg gggacattt tacttataaa tttttttca    13800
atgacttttg gggtacaagt ggttttggt tacaatgatg aactgtatac tggtgaaatc    13860
ttagatttta gtgcacctat cacctgagta gtgtacattg tacccaatac gtagttttta    13920
atccctcacc ccctcccacc ctacccttc taagtctcca aagcccatgc cttttcatac    13980
ccatagctaa actctcattt ctaagtaaga acatacagta tttgatttc cattcctgag    14040
ttacttcact tggaacaatg gcctccagct ccatccaagt tgctgcaaaa tacattattt    14100
tattctttt catagctgag tagtattcta tggtatatac accacgtttt ctttacccac    14160
tcattggttg gttgacactt aggttggttc cagatctttg caattgtgaa ttgtgctgcc    14220
ataaacatgc atgcaggtgt tttttgatat aaggacttct tttcctttgg ggagataccc    14280
agtaggggat tgttggatca aatggtagat ctactctcag atttagattt taatttactt    14340
ttagatttta gatttagaaa tctccattct gttttccata gaggctgtac taatttacat    14400
tcccaccagc agtgtataaa tgttacctt tcaccacatt catgccaaca tctactgttt    14460
tttgactttt taataatgac cattctggct ggggtaaagc ggtatctcac tgtggttta    14520
attggattt ttgtgatgat tagtgatgta gagtgttttt ccatatgttt gttggccatt    14580
tgtatgtctt cttttgagaa atatttattc atatcatttg cccactttt aatgagatct    14640
ttttttgttt tttgttgct aatttgtttg agttccctgt aaattctgga tattagttct    14700
ttgtcagata catagtttgc aaatattttc tcccattctg tggattgcct gtttgctttg    14760
atgattattt tttctgttgt gcagaagctt tcagtttaat gaggtcccat ttatttattt    14820
ttgttttgt tgcatttact tttggggtct tagtcacaaa ttcttatcta agtcaatgtc    14880
cagtagagtt tttcctgttt tcttctataa ttttgtggt ttcaggtctt agatttaagt    14940
ctttaatcat attgagttga tttttgtata aggtgagtgg gatccagttt tattctccta    15000
catggggcta tccagttttc ccagcaacat ttactaaata gggtgtcctt tccctaattt    15060
atgttttgt atgctttgtt gaagatcagt tggttgttan nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
nnnnnnnnnn nnnnnnnnnn nnnnnnnnnn nnnnnnnnnn nnnnnnnnnn nnnnnnnnnn    15300
nnnnnnnnnn nnnnnnnnnn nnnnnnnnnn nnnnnnnnnn nnnnnnnnnn nnnnnnnnnn    15360
nnnnnnnnnn nnnnnnnnnn nnnnnnnnnn nnnnnnnnnn nnnnnnnnnn nnnnnnnnnn    15420
nnnnnnnnnn nnnnnnnnnn nnnnnnnnnn nnnnnnnnnn nnnnnnnnnn nnnnnnnnnn    15480
nnnnnnnnnn nnnnnnnnnn nnnnnnnnnn nnnnnnnnnn nnnnnnnnnn nnnnnnnnnn    15540
nnnnnnnnnn nnnnnnnnnn nnnnnnnnnn nnnnnnnnnn nnnnnnnnnn nnnnnnnnnn    15600
nnnnnnnnnn nnnnnnnnnn nnnnnnnnnn nnnnnnnnnn nnnnnnnnnn nnnnnnnnnn    15660
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 15720 |
| nnnnnnnnnn | nnnnnnnnnn | nnnnnnnnnn | nnnnnnnnnn | nnnnnnnnnn | nnnnnnnnnn | 15780 |
| nnnnnnnnnn | nnnnnnnnnn | nnnnnnnnnn | nnnnnnnnnn | nnnnnnnnnn | nnnnnnnnnn | 15840 |
| nnnnnnnnnn | nnnnnnnnnn | nnnnnnnnnn | nnnnnnnnnn | nnnnnnnnnn | nnnnnnnnnn | 15900 |
| nnnnnnnnnn | nnnnnnnnnn | nnnnnnnnnn | nnnnnnnnnn | nnnnnnnnnn | nnnnnnnnnn | 15960 |
| nnnnnnnnnn | nnnnnnnnnn | nnnnnnnnnn | nnnnnnnnnn | nnnnnnnnnn | nnnnnnnnnn | 16020 |
| nnnnnnnnnn | nnnnnnnnnn | nnnnnnnnnn | nnnnnnnnnn | nnnnnnnnnn | nnnnnnnnnn | 16080 |
| nnnnnnnnnn | nnnnnnnnnn | nnnnnnnnnn | nnnnnnnnnn | nnnnnnnnnn | nnnnnnnnnn | 16140 |
| nnnnnnnnnn | nnnnnnnnnn | nnnnnnnnnn | nnnnnnnnnn | nnnnnnnnnn | nnnnnnnnnn | 16200 |
| nnnnnnnnnn | nnnnnnnnnn | nnnnnnnnnn | nnnnnnnnnn | nnnnnnnnnn | nnnnnnnnnn | 16260 |
| nnnnnnnnnn | nnnnnnnnnn | nnnnnnnnnn | nnnnnnnnnn | nnnnnnnnnn | nnnnnnnnnn | 16320 |
| nnnnnnnnnn | nnnnnnnnnn | nnnnnnnnnn | nnnnnnnnnn | nnnnnnnnnn | nnnnnnnnnn | 16380 |
| nnnnnnnnnn | nnnnnnnnnn | nnnnnnnnnn | nnnnnnnnnn | nnnnnnnnnn | nnnnnnnnnn | 16440 |
| nnnnnnnnnn | nnnnnnnnnn | nnnnnnnnnn | nnnnnnnnnn | nnnnnnnnnn | nnnnnnnnnn | 16500 |
| nnnnnnnnnn | nnnnnnnnnn | nnnnnnnnnn | nnnnnnnnnn | nnnnnnnnnn | nnnnnnnnnn | 16560 |
| nnnnnnnnnn | nnnnnnnnnn | nnnnnnnnnn | nnnnnnnnnn | nnnnnnnnnn | nnnnnnnnnn | 16620 |
| nnnnnnnnnn | nnnnnnnnnn | nnnnnnnnnn | nnnnnnnnnn | nnnnnnnnnn | nnnnnnnnnn | 16680 |
| nnnnnnnnnn | nnnnnnnnnn | nnnnnnnnnn | nnnnnnnnnn | nnnnnnnnnn | nnnnnnnnnn | 16740 |
| nnnnnnnnnn | nnnnnnnnnn | nnnnnnnnnn | nnnnnnnnnn | nnnnnnnnnn | nnnnnnnnnn | 16800 |
| nnnnnnnnnn | nnnnnnnnnn | nnnnnnnnnn | nnnnnnnnnn | nnnnnnnnnn | nnnnnnnnnn | 16860 |
| nnnnnnnnnn | nnnnnnnnnn | nnnnnnnnnn | nnnnnnnnnn | nnnnnnnnnn | nnnnnnnnnn | 16920 |
| nnnnnnnnnn | nnnnnnnnnn | nnnnnnnnnn | nnnnnnnnnn | nnnnnnnnnn | nnnnnnnnnn | 16980 |
| nnnnnnnnnn | nnnnnnnnnn | nnnnnnnnnn | nnnnnnnnnn | nnnnnnnnnn | nnnnnnnnnn | 17040 |
| nnnnnnnnnn | nnnnnnnnnn | nnnnnnnnnn | nnnnnnnnnn | nnnnnnnnnn | nnnnnnnnnn | 17100 |
| nnnnnnnnnn | nnnnnnnnnn | nnnnnnnnnn | nnnnnnnnnn | nnnnnnnnnn | nnnnnnnnnn | 17160 |
| nnnnnnnnnn | nnnnnnnnnn | nnnnnnnnnn | nnnnnnnnnn | nnnnnnnnnn | nnnnnnnnnn | 17220 |
| nnnnnnnnnn | nnnnnnnnnn | nnnnnnnnnn | nnnnnnnnnn | nnnnnnnnnn | nnnnnnnnnn | 17280 |
| nnnnnnnnnn | nnnnnnnnnn | nnnnnnnnnn | nnnnnnnnnn | nnnnnnnnnn | nnnnnnnnnn | 17340 |
| nnnnnnnnnn | nnnnnnnnnn | nnnnnnnnnn | nnnnnnnnnn | nnnnnnnnnn | nnnnnnnnnn | 17400 |
| nnnnnnnnnn | nnnnnnnnnn | nnnnnnnnnn | nnnnnnnnnn | nnnnnnnnnn | nnnnnnnnnn | 17460 |
| nnnnnnnnnn | nnnnnnnnnn | nnnnnnnnnn | nnnnnnnnnn | nnnnnnnnnn | nnnnnnnnnn | 17520 |
| nnnnnnnnnn | nnnnnnnnnn | nnnnnnnnnn | nnnnnnnnnn | nnnnnnnnnn | nnnnnnnnnn | 17580 |
| nnnnnnnnnn | nnnnnnnnnn | nnnnnnnnnn | nnnnnnnnnn | nnnnnnnnnn | nnnnnnnnnn | 17640 |
| nnnnnnnnnn | nnnnnnnnnn | nnnnnnnnnn | nnnnnnnnnn | nnnnnnnnnn | nnnnnnnnnn | 17700 |
| nnnnnnnnnn | nnnnnnnnnn | nnnnnnnnnn | nnnnnnnnnn | nnnnnnnnnn | nnnnnnnnnn | 17760 |
| nnnnnnnnnn | nnnnnnnnnn | nnnnnnnnnn | nnnnnnnnnn | nnnnnnnnnn | nnnnnnnnnn | 17820 |
| nnnnnnnnnn | nnnnnnnnnn | nnnnnnnnnn | nnnnnnnnnn | nnnnnnnnnn | nnnnnnnnnn | 17880 |
| nnnnnnnnnn | nnnnnnnnnn | nnnnnnnnnn | nnnnnnnnnn | nnnnnnnnnn | nnnnnnnnnn | 17940 |
| nnnnnnnnnn | nnnnnnnnnn | nnnnnnnnnn | nnnnnnnnnn | nnnnnnnnnn | nnnnnnnnnn | 18000 |
| nnnnnnnnnn | nnnnnnnnnn | nnnnnnnnnn | nnnnnnnnnn | nnnnnnnnnn | nnnnnnnnnn | 18060 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 18120 |
| nnnnnnnnnn | nnnnnnnnnn | nnnnnnnnnn | nnnnnnnnnn | nnnnnnnnnn | nnnnnnnnnn | 18180 |
| nnnnnnnnnn | nnnnnnnnnn | nnnnnnnnnn | nnnnnnnnnn | nnnnnnnnnn | nnnnnnnnnn | 18240 |
| nnnnnnnnnn | nnnnnnnnnn | nnnnnnnnnn | nnnnnnnnnn | nnnnnnnnnn | nnnnnnnnnn | 18300 |
| nnnnnnnnnn | nnnnnnnnnn | nnnnnnnnnn | nnnnnnnnnn | nnnnnnnnnn | nnnnnnnnnn | 18360 |
| nnnnnnnnnn | nnnnnnnnnn | nnnnnnnnnn | nnnnnnnnnn | nnnnnnnnnn | nnnnnnnnnn | 18420 |
| nnnnnnnnnn | nnnnnnnnnn | nnnnnnnnnn | nnnnnnnnnn | nnnnnnnnnn | nnnnnnnnnn | 18480 |
| nnnnnnnnnn | nnnnnnnnnn | nnnnnnnnnn | nnnnnnnnnn | nnnnnnnnnn | nnnnnnnnnn | 18540 |
| nnnnnnnnnn | nnnnnnnnnn | nnnnnnnnnn | nnnnnnnnnn | nnnnnnnnnn | nnnnnnnnnn | 18600 |
| nnnnnnnnnn | nnnnnnnnnn | nnnnnnnnnn | nnnnnnnnnn | nnnnnnnnnn | nnnnnnnnnn | 18660 |
| nnnnnnnnnn | nnnnnnnnnn | nnnnnnnnnn | nnnnnnnnnn | nnnnnnnnnn | nnnnnnnnnn | 18720 |
| nnnnnnnnnn | nnnnnnnnnn | nnnnnnnnnn | nnnnnnnnnn | nnnnnnnnnn | nnnnnnnnnn | 18780 |
| nnnnnnnnnn | nnnnnnnnnn | nnnnnnnnnn | nnnnnnnnnn | nnnnnnnnnn | nnnnnnnnnn | 18840 |
| nnnnnnnnnn | nnnnnnnnnn | nnnnnnnnnn | nnnnnnnnnn | nnnnnnnnnn | nnnnnnnnnn | 18900 |
| nnnnnnnnnn | nnnnnnnnnn | nnnnnnnnnn | nnnnnnnnnn | nnnnnnnnnn | nnnnnnnnnn | 18960 |
| nnnnnnnnnn | nnnnnnnnnn | nnnnnnnnnn | nnnnnnnnnn | nnnnnnnnnn | nnnnnnnnnn | 19020 |
| nnnnnnnnnn | nnnnnnnnnn | nnnnnnnnnn | nnnnnnnnnn | nnnnnnnnnn | nnnnnnnnnn | 19080 |
| nnnnnnnnnn | nnnnnnnnnn | nnnnnnnnnn | nnnnnnnnnn | nnnnnnnnnn | nnnnnnnnnn | 19140 |
| nnnnnnnnnn | nnnnnnnnnn | nnnnnnnnnn | nnnnnnnnnn | nnnnnnnnnn | nnnnnnnnnn | 19200 |
| nnnnnnnnnn | nnnnnnnnnn | nnnnnnnnnn | nnnnnnnnnn | nnnnnnnnnn | nnnnnnnnnn | 19260 |
| nnnnnnnnnn | nnnnnnnnnn | nnnnnnnnnn | nnnnnnnnnn | nnnnnnnnnn | nnnnnnnnnn | 19320 |
| nnnnnnnnnn | nnnnnnnnnn | nnnnnnnnnn | nnnnnnnnnn | nnnnnnnnnn | nnnnnnnnnn | 19380 |
| nnnnnnnnnn | nnnnnnnnnn | nnnnnnnnnn | nnnnnnnnnn | nnnnnnnnnn | nnnnnnnnnn | 19440 |
| nnnnnnnnnn | nnnnnnnnnn | nnnnnnnnnn | nnnnnnnnnn | nnnnnnnnnn | nnnnnnnnnn | 19500 |
| nnnnnnnnnn | nnnnnnnnnn | nnnnnnnnnn | nnnnnnnnnn | nnnnnnnnnn | nnnnnnnnnn | 19560 |
| nnnnnnnnnn | nnnnnnnnnn | nnnnnnnnnn | nnnnnnnnnn | nnnnnnnnnn | nnnnnnnnnn | 19620 |
| nnnnnnnnnn | nnnnnnnnnn | nnnnnnnnnn | nnnnnnnnnn | nnnnnnnnnn | nnnnnnnnnn | 19680 |
| nnnnnnnnnn | nnnnnnnnnn | nnnnnnnnnn | nnnnnnnnnn | nnnnnnnnnn | nnnnnnnnnn | 19740 |
| nnnnnnnnnn | nnnnnnnnnn | nnnnnnnnnn | nnnnnnnnnn | nnnnnnnnnn | nnnnnnnnnn | 19800 |
| nnnnnnnnnn | nnnnnnnnnn | nnnnnnnnnn | nnnnnnnnnn | nnnnnnnnnn | nnnnnnnnnn | 19860 |
| nnnnnnnnnn | nnnnnnnnnn | nnnnnnnnnn | nnnnnnnnnn | nnnnnnnnnn | nnnnnnnnnn | 19920 |
| nnnnnnnnnn | nnnnnnnnnn | nnnnnnnnnn | nnnnnnnnnn | nnnnnnnnnn | nnnnnnnnnn | 19980 |
| nnnnnnnnnn | nnnnnnnnnn | nnnnnnnnnn | nnnnnnnnnn | nnnnnnnnnn | nnnnnnnnnn | 20040 |
| nnnnnnnnnn | nnnnnnnnnn | nnnnnnnnnn | nnnnnnnnnn | nnnnnnnnnn | nnnnnnnnnn | 20100 |
| nnnnnnnnnn | nnnnnnnnnn | nnnnnnnnnn | nnnnnnnnnn | nnnnnnnnnn | nnnnnnnnnn | 20160 |
| nnnnnnnnnn | nnnnnnnnnn | nnnnnnnnnn | nnnnnnnnnn | nnnnnnnnnn | nnnnnnnnnn | 20220 |
| nnnnnnnnnn | nnnnnnnnnn | nnnnnnnnnn | nnnnnnnnnn | nnnnnnnnnn | nnnnnnnnnn | 20280 |
| nnnnnnnnnn | nnnnnnnnnn | nnnnnnnnnn | nnnnnnnnnn | nnnnnnnnnn | nnnnnnnnnn | 20340 |
| nnnnnnnnnn | nnnnnnnnnn | nnnnnnnnnn | nnnnnnnnnn | nnnnnnnnnn | nnnnnnnnnn | 20400 |

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 20460 |
| nnnnnnnnnn | nnnnnnnnnn | nnnnnnnnnn | nnnnnnnnnn | nnnnnnnnnn | nnnnnnnnnn | 20520 |
| nnnnnnnnnn | nnnnnnnnnn | nnnnnnnnnn | nnnnnnnnnn | nnnnnnnnnn | nnnnnnnnnn | 20580 |
| nnnnnnnnnn | nnnnnnnnnn | nnnnnnnnnn | nnnnnnnnnn | nnnnnnnnnn | nnnnnnnnnn | 20640 |
| nnnnnnnnnn | nnnnnnnnnn | nnnnnnnnnn | nnnnnnnnnn | nnnnnnnnnn | nnnnnnnnnn | 20700 |
| nnnnnnnnnn | nnnnnnnnnn | nnnnnnnnnn | nnnnnnnnnn | nnnnnnnnnn | nnnnnnnnnn | 20760 |
| nnnnnnnnnn | nnnnnnnnnn | nnnnnnnnnn | nnnnnnnnnn | nnnnnnnnnn | nnnnnnnnnn | 20820 |
| nnnnnnnnnn | nnnnnnnnnn | nnnnnnnnnn | nnnnnnnnnn | nnnnnnnnnn | nnnnnnnnnn | 20880 |
| nnnnnnnnnn | nnnnnnnnnn | nnnnnnnnnn | nnnnnnnnnn | nnnnnnnnnn | nnnnnnnnnn | 20940 |
| nnnnnnnnnn | nnnnnnnnnn | nnnnnnnnnn | nnnnnnnnnn | nnnnnnnnnn | nnnnnnnnnn | 21000 |
| nnnnnnnnnn | nnnnnnnnnn | nnnnnnnnnn | nnnnnnnnnn | nnnnnnnnnn | nnnnnnnnnn | 21060 |
| nnnnnnnnnn | nnnnnnnnnn | nctgtggggg | gctccaccca | gtttgagctt | cccagctgct | 21120 |
| ttgtttacct | actcaagcct | cagcaatggc | ggatgtccct | ccaccagcct | cattgccacc | 21180 |
| ttgcagttca | atctcagact | gctgtgctag | cagtgagtga | ggctccatgg | gcgtgggacc | 21240 |
| ctctgagcca | ggtgcgggat | atgatctcct | ggtgtgccat | ttgctaggac | tgttggaaga | 21300 |
| gcacagtatt | agggtgggag | tgtcccgatt | ttccaggtac | cttctgtcat | cacttccctt | 21360 |
| ggctaagaaa | ggggattccc | tgaccccttg | cacttcctgg | gtgaggcgat | gccctgccct | 21420 |
| agttcagctc | acacttcgtg | ggctgcaccc | actgtccaac | aagccccagt | gcgatgaacg | 21480 |
| cggtacctca | gttggaaatg | cagaaatcac | ctgtcttctg | cgttgctcat | gctgggagct | 21540 |
| gtagactgga | gctgttccta | tttggccatc | tttgaacctc | cccctgact | tgcgtatgtt | 21600 |
| aaatcttccc | tctatctctg | ggacaaagcc | catttgatca | tgatgtatta | tgttttgat | 21660 |
| ttgctattgg | attctgtttg | ctggtatttt | gttgaggact | tttgcatcta | tgttcatcag | 21720 |
| gaatattgat | ctgtagtttt | cttttttgtt | atgtcatttc | ctgggtttga | cacagggtga | 21780 |
| tactggcttc | atagaatgag | tttgggagga | ttttctcttt | ctcaatcttt | ttgaataatc | 21840 |
| tcaatagtat | tgcttccaat | tcttctttga | ctgtctggta | gaattcagct | atgaatccat | 21900 |
| ctggccctag | gctttttgt | tgctggcaat | ttcaatcagt | aaattttact | tagtcagtct | 21960 |
| cactgcttgt | tatctggtct | gctcaggatt | tctatttctt | cctgatttaa | tctgggatgg | 22020 |
| ttgtaaattt | ccaggaattt | atccatttct | tctatgtttt | ttagtttgtg | tgaatagaga | 22080 |
| tgttcatagt | aatctcaact | gatcttttgt | atttctgttt | cattggttgt | agtgtctcta | 22140 |
| ttttcatttc | taattgaact | tattcaaaac | ttctctcctc | ttagttaatc | tagttaatgg | 22200 |
| tctatcaatt | ttgtttatct | tttcaaagaa | ccaactttt | gttttactaa | ccttgtgtaa | 22260 |
| tattttttgtt | tcaatttcat | ttatttctgc | tctggtcttt | gttgtttctt | ttcttctcta | 22320 |
| gctttgggtt | cctttgttcc | tgtttcttta | gctccttgag | gtgcgatgtt | agggtgtcaa | 22380 |
| gttgtgatct | ttcagacttt | ttgatgtagg | catttagtgc | tataaacttt | cctcttagca | 22440 |
| ccacttttgc | tgtatctcag | aagttttgac | aactgtgtca | tattatcatt | catttcaagt | 22500 |
| aattttttaaa | tgttcatctt | tatttcattg | ttaacccaaa | atttatacag | gagcagattt | 22560 |
| tttaatttcc | atgtatttgt | atagttttga | gaattccttt | tggagttggt | ttctagtttt | 22620 |
| ttcctactgt | ggtctgagaa | gatgcttgat | atgattttga | tttttaaaaa | ttattgatac | 22680 |
| ttgttttgta | gccaatcgta | tggcctatgt | tggaatatat | tccatgtgct | gatgagaaga | 22740 |
| aagtatattc | tatagttttt | gggtaggatg | ttctgtaaat | atctgttagg | tctacttgtt | 22800 |

```
ttagagtatt gtttaagtca ttgtttcttt gttgactttc tgcctcgatg atctgtctag   22860
tgctgtcagt ggggtgttga agtatcccac tattattggg ttgctcatta tctctttcct   22920
taggtctagc agtaattgtt ttatgaattt tggagctcca tagttaggta cacatatatt   22980
ttggattata atattctctt gtcagattaa tccttttatc attatataat tgtaaccacc   23040
taacaggtta tttctgccca ctgcacaagc aaaatcaatt catggcattg tggtgaagaa   23100
agtgtttaat tgatgcaagg ccagtcatgc catgtggtca aactaggatg agatattac    23160 tcaaatcaat ctcatcaaag gcttgttggt tagggttttt tcaaaggcag ttttggggaa   23220
gggattgggc tgaccagacc aggtgcttgc tgctgattgt ttgggttgga gatgaaatca   23280
tatggagttg aagctgtcct cttgtgctga gtcacttctg tggggccaca ggagtggttg   23340
gtgggtccat atgggtccaa gtgaagccat cggtgtcaga catgcaaaaa acctgaaaag   23400
atatctcaaa aggctaatct taggttctac aatagtgatg ttatctgcat gagtaattgg   23460
gggagttgca tatctgtgac ctctggaata atggctgtca atcatttata tccacacctt   23520
agcagaattc aggctcttct cctcctccta agtctggtgg tttctcatta gctttacaaa   23580
ggtgactgag ttttgggaaa gattattatc atttaaacta caaactaaat gtctcccaaa   23640
gctagccaag actaagccca ggaataatta aggcagcttg aaggctaaag caagaggga   23700 ggttggctag atcagatgtc ccccactgcc ataattgtct cagtgatata attttgcaa   23760 aggtggtttt ataatgacct tctttgtctt tttctttttt ttaactgttg ttgctttaaa   23820
gtctgtttta tttaatataa gaatagccac tcctacccag gcacggtggc tcacacctgt   23880
aaatcccagc actttgggag gctgaggcag gtatatcacc tgaggtcagg agttcaagac   23940
cagccagaca gagatggtga aactccatct ctactaaatt tacaaaaaca ttagccaggc   24000
atggtggggg gcacctgtaa tcccagctac tcaggaggct gaggcaggag aattgcttgt   24060
acccgggagg cagaggttgc agtgagccaa gattgcgcct tgctctccag cctgggcaac   24120
aaagtgagac ttcatctcaa aaaaaaaaaa aaaaaaaaa aagaatagct actcctgcta   24180
gcctttggtt tccatataca cagaacatct tttcccaccc ctttaccttg tgcttgtgtg   24240
aatccttatg cattagatga gtctcttgaa gacagcagat atttggtttg tgatattta   24300 tccattctgc caatctgtat gttttcagtg gagcatttat gccatttatg tttaatatta   24360
acattgagat gtaaggtacg attctcctca tcatgttgat tattacctgg atcctttgt    24420 gtgtgtgtgt gtgtgttatt gttttttattt ttttattta atttttttga gacagagtct   24480
tgctctgtca cccaggctgg agtgcagtgg cgagatctct gctcactgca agctccgcct   24540
cctgggttca tgccattctc ctgcctcagc ctcccgagta gctggactac agacacccg    24600 ccactacgcc tggctaattt tttgtatttt tagtagagac ggggtttcac catgttagcc   24660
aggatggtct cgatctcctg acctcgtgat ccaccccct tggcctccca aagtgctggg   24720
attacaggtg tgagccaccg tgcccggcca tgtgtgtgtg ttattgtttt ataggccctg   24780
tgagttttat gctttcaaga ggttttattc tgatgcatgt caacttttgg tttcaagatt   24840
tagaagtcct tttagaattt tgtgtatggc tggtctggta gttacaaatt ccttcatcat   24900
ttgcttgtct ggaaaagact ttatttctct ttcatttatg aaacttagtt ttgctggaca   24960
caaaattctt gactgacact tattctgttt aaggaggcta agattggac cccaatccct    25020 tctggcttgt aaggtttctg ctgagggaa gatttttatc aatgacataa atgtgtgatg    25080
atggaaacaa tccagtggga agagaaaatt gatgcaggag agaagaaaga aagcttttt    25140
```

```
ggagggctgc tctttagtat atgagagtag atggaatcta ttcaacatgt aaaggagtct   25200
tagctaggcc ttagatagga gtaggaattg tttatccaaa gtaaaatgaa ggaagagaga   25260
ttccagtagg ttggaagaca tggtgggaag gacttgagga aattctcctc tattgcttat   25320
tttactcaat aaagtaggaa gcaaggttac cagctgtgaa tgaggagtgg aagaaggcat   25380
tagagacttg atgagagaaa agaagccatg aaagagttat acaaaagtgt atgaggttta   25440
ttggactagg gaaagtatgt ctgccaggcg ctttaaaggg ccaactgaag ttagtgacca   25500
gaaattcaaa gtgagacaag ccattatgtc caacagcatg ggtgcaggca gagagtagtg   25560
ggaagctgga tttaaccaga gtcatggttt agcaaagtga actcaacaac ctgggagaga   25620
gacaggggaa cttagggagt gcccgaaggc atgataacat taatagagat cctcctccag   25680
tgaatgtcac cagcctccca gttgctcaac tgagaaacct tgaccttttc ctcaacccct   25740
aacacccaaa caccaagtgg tattgatttc acttcctaaa tatctcctcc tttcctcatt   25800
ggattaagct actgtaattt gtcttcatgt ttatatcatt tcccccatag cagccagagg   25860
tgatgtttta gaaattacaa gcctgatcat gtaactacct acttacaagc ttccagcagc   25920 ttctttttt ttttcaagtg gcagttttaa gtttgtgggt tttaatttta tatatgtgaa   25980
ataccttttt ataggcaaaa ataataatag catgcttctt actgcccttt atgtgaaatg   26040
actcacaaga ccttggtgtg gccaactctc cagcctcttt tttggcttat attttttcctt  26100 cttccccata tgccagccct actttcttct ttcaattctt caaagtcagt catctctgag   26160
ggtgcatata ccccccagaga atgcccaaga tgattcactg ggatgaggaa aaaaaatact   26220
agaacttcct tttatattta tttgtgatta tatattttta atttctgtga ttatatgtat   26280
tgaaaatgtg taaatcagta gtacatggat acacttttata aatacatata catatattag   26340
agtagtgctc aaatatattt tttattatgc acatgcagtt gtaagaatat gtacagagac   26400
cacatgtacc atttacccag tttcacacaa acttgcatct tgcaaaacta tagtcataac   26460
cttgatatta atattgatct aattcactga tcttattaag attttcccag ttcttgtatt   26520
catgcatgtg tatgtatttt aactctatgg aatgttatca cataaatagg ttgttatatt   26580
ccccaccaca gtaaagatac aggacaagtc cattatcaca agggcccttc aagtggctct   26640
tctgtagcca cctcctaacc ccctataccc tgtccctgac tcctgccagc cactaatccg   26700
ttctccattt ctataatttt gtcattccaa gaaaattata tacaagaaat catacagtag   26760 taaccttta ggattggcat ttttcactca ccatacttct cgggcaattc atctaaactg    26820
ttgtatcaat agttggttca ttttttattgc tgagtggtat tccacgtatg taggtaccac   26880
aatttgttta accattcacc agctgaggac atgtagattc tttgcagtta ggagctatta   26940
tcaataaagc aactaatgat gttgaatatt aaaaaaatgc tttattgaca aaggaagcca   27000
atcaaaaaag cttgtagacc ataaccctaa tgtttcaggt cttcctacc tcaagatctt    27060 ctgtcctacc catccctact tttagaacct ctccctactt ttctctagct aactcttgga   27120
ctccagagaa agtgttaaaa gtcttcccta accccagac caggagtaca tcccctgtt     27180 ttatgctcct aatgctcctg gcacttttcc ccctaagccc actgtacctg atattttcta   27240
tctgcccctc cagatctact ctccacccctt cttcattctg ctctcagccc aggactacat   27300
caaatctcct tagtcctctg ggttccagtt gactttgatc tctagggagc ccttgcaggg   27360
gaaggaagga gaaggagggc ctgatttttat tccccagcc cctcacggta aggctgactc    27420
aggcaacttt tgtgtctaga aggaaagcct cagcttctct ctacacaaaa ctatcttcct   27480
aggttttaat atctgctccc ttcccttttgt cccttggtc ctgtagacgt attttgcttg   27540
```

```
gtctaatcct aggttttaaa atttgaatta gttgttgata cttaataatt ggaagatttt    27600
gcataaagtt tcagatgtct ggcttctctt gaaaaaaaat cagaaggttt gacaacactg    27660
agcctccatt ccaaatagta gccattgtgt ggccttgagt agagccaccc cttccactgg    27720
ggcagctact cttaaggatt caccatcccc actaactccc tgttccatac aataaccttg    27780
ctttgctatt accaccctgg cactaggagt cctggtttaa agaatgtgtt gcccgctagg    27840
tgggacctgt gtcagacttc tcatcagatt tggagaaagg gcatgctggc ctctcccatc    27900
tgtctacttc tctctgtctc cccttgcacc acatagagca ccctttctct ggggtttcta    27960
tcatcccctc ctagactccc acttgctccc aggcttgctg ctcctctctg cacttctcac    28020
atcttgccag agtgcttttt ttttttctt tttttgagg tggagtctca ctctgtcacc    28080
taggctggag tgcagtggtg tgatcttggc tcactgcaac ctctgccccc tgggttcaag    28140
caattctcct gtctcagcct cccaagtagc cagaattaca gcggctgcc accatgcctg    28200 gctaattttt tgtatttata gtagagacgg ggtttcactt tcaccatctt gaccaggctg    28260
gtcttgaact cttgacccttg tgatccaccc gcctcggcct cccaaagtgc tgggattaca    28320
ggtgtgaggc atcacacccg gcccagagtg ctcttttttaa atgggactca gattacaacc    28380 cttttttctta aaaccttgct atgttttctc attgccctat agttaaagcc tgcatttcta    28440
aagcagtccc ctggcttatc tgacctttc ctactaccag gctgatctgg ggccacccct    28500
cctcattctg cttttccaga acagtgggtt cctcaagcac acaccttatg tcttgcctgg    28560
gcagcacact tgccaagctc ctaggccaag tatgaggcct ctctcctcac ttcctggtca    28620
caatttaagt gcccttaccc agatagtgcc tttccattct ctgtctgtat ctcttcttaa    28680
taggtgctat gcttgtaaga agggattttt tttttagtct ttctctcatt ggactgtgag    28740
aatagtgttt atcttttca ctgcctggtg tatagtaggt gctcattgaa catttattga    28800
aagagcagat ttagagatct agctcttcat ggaatagcag tttctaccac ctagcgacaa    28860
tgtggaatac cagggcttct aaagtgttta gtatgatcat acatttatat tatgaggcct    28920
gcctgtgggg tgattgcaca tgaggtgagg ccattgaggc acctagggca gaggatttaa    28980
ggaagctttc acccttacaa tgcctctcct gccacactct agacctggct ctgggaggga    29040
agcctttgct aagaaccatg aaaggaaagg agaaaaagaa aactagggtg gtgctaaagg    29100
gacatttgtg atggcagcct gacacctacc acctgattct tgaacactca ctgtggatag    29160
aatggtgtat gatggccaca gggcaggagg gggcagcaga gtgatgatac cttaactgac    29220
acctgagtca gtaatgggag aactgaggag aagcagtggg ttcttctaca ggaaatcgaa    29280
gggtggaatt cattaatcta gcccttaaaa caacagctta cccaacatgc tacacaaaac    29340
caggtttctg tttcagataa ataggtgaag ggactcttaa tcctaaagac tgaaaagtag    29400
aaaagaaagg ggaagaagag tgcctcaagg attgccattg gaggttctttt tgctgggct    29460 gattgccagc tgagattatt caagccccag agcaaacatt ctgctcctgc tcccttagag    29520 ctgcctccc accgctcagt attgcctcct gcgaggggcg ggctggctgc cgcagacacc    29580
agtgaaccct ttttccattc cagaagtccc agtggaccta ctttaatata ccaataacac    29640 tcctattta aactagctgt atccatttc gttttaatag tcccagtgct aaagtttttc    29700
aaagcagtta ttttgtaagt aggtcaaaca ggtactttgg gatcctgttc tgtctgtttg    29760
cttgccaggt aacctcttg ttatctaatt caaagtctgg tacagtttga accaaaacaa    29820
aaaaggaatg atgtttcact ttggagtcaa gattcattca ttttctaaca ttaatcattt    29880
```

-continued

| | | | | |
|---|---|---|---|---|
| tcgtaataca | gtaagtctat | attcatgata | aaaatagaa | aatatgaata agcaaaacta | 29940 |
| aattgaaagg | aaaaccatct | gtgatctgcc | aattagaaaa | tctctattct aaacattttg | 30000 |
| gtaaatatgc | taccagattt | ttatctatgc | aaatgtgtat | ctgtattttt cctcacttgt | 30060 |
| atagtggaca | tcttttcata | ttaataaata | agttagcatc | attacttttg atagcttcat | 30120 |
| ggtgtgaaat | tataaaatta | gacctaccac | actctatttt | aactatctct cttgctgggt | 30180 |
| acttaagcta | ttcccaatat | cacagaagcc | ttttacaca | tgcatccttg tacatgcatc | 30240 |
| agattcttta | agattgccaa | aggtgaaatg | gttgggtccc | agggtgcaac tattttttag | 30300 |
| catttcaata | cataatacca | aagtgcaatc | cagaaccatt | gtaccaatta atgctcccgc | 30360 |
| cagcagcaca | ttgcagtgtt | gatttcctcc | tggcctcacc | agcacgctgt caacactggg | 30420 |
| tactggtgtg | tcgtgtacat | gacattacat | gccaggcact | gagagtgaaa taaaacagtt | 30480 |
| catgttggga | atggggcaag | agagggagat | aaacaaggga | ggtgacatct acagaccggt | 30540 |
| tagctgagat | tacagtacat | tggggctcca | agtgcacaga | atctgaacat catgttcatc | 30600 |
| ctaggacaag | tgttgcagag | gcttcctgaa | gaggttcatt | ctgaggctta ccttgaagga | 30660 |
| tcatcaggaa | ttaatgatga | gtgtattaag | ccattctcgc | atttctataa agaaacgcct | 30720 |
| gaaattgagt | aatttttttt | tttttttttt | tttctgagac | ggagtcttgc tttcttacct | 30780 |
| aggctggaga | gcagtggtgc | gatctcggct | cactgcaacc | tctgcctccc tgggttcaag | 30840 |
| tgattctcct | gcctcagcca | cccgagtagc | acaggtgcct | gccaccgggt ccatctaatt | 30900 |
| tttgtatttt | tagtagagac | agggtttcac | catgttggcc | aggctggtct caaactccca | 30960 |
| acctcgtgat | cctcccgcct | tggcctcccg | aagtgctggg | attacaggcg tgagctgccg | 31020 |
| cgcccagcca | aaattgagta | atttataaga | aaaaaggtt | ttattagctc atgattctgc | 31080 |
| aggctgtaca | ggaagcgtgg | tggcatctgc | ttctgtagag | gcctcaggaa gctccaatca | 31140 |
| tggtggaagg | tggaaggcac | atcacactgt | gaaagcagga | gcaagagttg ggggaacatg | 31200 |
| ccataagatc | ccatcacttt | taaagaacca | gatctcatgt | gaactcagag cgagagctca | 31260 |
| cttatcacta | aggagatggc | ccaagccatt | catgagacat | cagcctccat gacccaaaca | 31320 |
| cgtcccacca | gactccacct | ccaacattgg | ggattacatt | tcaatgagat ttgggtgggg | 31380 |
| acaaatgtcc | aaactatatt | gatgagtgaa | agcaagagta | agaacaggg aaggaatgat | 31440 |
| ggagagaatg | aaccaggtag | agaaaatctt | ctaggcatga | atgttcagcc ccttttcagg | 31500 |
| gagcaacaaa | aagttctgta | ttggttgcaa | tgaagggtgc | atggggcatt ggggatggtg | 31560 |
| gacaggaatg | atggacagtg | aggctgatga | gatgagctgg | gtctcatcaa gaagttctct | 31620 |
| ccgggcttag | caaaggagct | ctagctttat | ctggaaactt | tccttgggag gcaggacttg | 31680 |
| gcatcaaaac | ctgtgtgtgg | aagactcaca | ccgatccaag | ggaagggcac tgatgctggg | 31740 |
| cttaagcatt | gctttgtcat | tccctgatga | gctctctcag | cttgggaaca gccactctct | 31800 |
| gtctagtaaa | ggaaaggagc | tgatccaggt | cctctccagt | tctaactatg ctcctgtgaa | 31860 |
| ttctggcaca | attttttactt | tttttccttg | cagaaaaggt | ggccattaag atcctggaca | 31920 |
| agaccaagtt | agaccagaaa | acccagaggc | tactatcccg | agaaatctcc agcatggaaa | 31980 |
| agctgcacca | tcccaacatc | atccgccttt | acgaagtggt | ggagaccta tccaagctgc | 32040 |
| acttggtgat | ggagtatgca | gggggtgggg | agctcttcgg | aaaaattagc actgagggga | 32100 |
| agctctctga | accagaaagc | aagctcatct | tctcccagat | tgtgtctgcc gtgaagcaca | 32160 |
| tggtgagcag | gggtgacgag | tgagaacctt | gctcccattg | cactgacact gggagcacag | 32220 |
| ggctttaggt | tactaaccct | caagtgtccc | agagggcttt | tgtcctacaa agcagacagt | 32280 |

```
agtcccttct gagagtcaga agtctggctg ggatcatgct ccttgcctgt gaagcaacat    32340
ccagggatgt ccagttacac gtcaacctcc tagcttctgc agacattggc aggaatcact    32400
gggagcagct gatgaatatc acccactccc tggccatacc catttctcca acctcatctt    32460
ccactatctg gatagctggc tcctcactgc ttcttggttt tgctttccta cttctgtcta    32520
ggatgccctc atatgacatc tcacattcta aatcctatcc atacttcatg cccagcttgg    32580
ttctctctct ctctctctcc cccaccccc ctctccgtgt gtgtgtgtgt gtgtgtgtgt    32640
gtgtgtgtgt gtgtgagaga gagagagaga gagagagaga tgttcttcaa tctcacatca    32700
gttatactga tattttgcct tcagtaagat cccctagctc ttattgcctc tgtgcccagt    32760
agattaacac ttggttgtgt cttctttttt tcccttcctt cctgcctgcc ttccatcctt    32820
ccttccttcc ttttcttcct cccttccttt cttttccttc cttccttcct tcctttcttt    32880
ctgtttcttt ttttttttt tagacagagt cttcctctgt cacccaggat ggagtgcagt    32940
ggcatgatct tggctcactg caacctccgc ctcccgggtt caagcgattc tcctgcctca    33000
gcctcccaag tagctgggat tacaggcatg tgccaccatg cctagctgat tttgtgtttt    33060
taatagagat gaggtttcac catgtttgtc aggcttgtct tgaactcctg acctcaagcg    33120
atccacctgc ctcggtctcc caaagtagtg ggattacagg cgtgagccac cgtgcctggc    33180
cgcttgtgtc attcttattt tagttctttg gttacttctt tagataaatc tggactccta    33240
atgcacactc tgtagttctc ccaagaactg gctgttttgc tgcctcctta attttggccg    33300
tattgcgggc catacaggag gaacctgact tgcaggcctg agtatcactt ttactaccaa    33360 aagtttagt cagtcaccat ctttactcag atcccagttg aacggatctg tcagaaaaga    33420
gacacttggc tagggtctat attagttgag aggctatttc caattcactt ctcagcctgc    33480
atggttgtag gagcaagaac tgggatcagt gagccacagt gaacctcatt acatgccagg    33540
cactgaaaaa gtcagataaa acagtccatg ctagcaatgg ggcaaaagag ggagaatttg    33600
caagggaatc tgtggcctag agggcccaaa atagcagtag ggaaggagag gaggaagaaa    33660
aagaagtgag ccagggagaa gagcttgact gtagtggtgg tggatgtttc agacctgtga    33720
tatatgacca atcatcattt aagtggcttt gggctgtggt gagctttccc agggccagag    33780
aataagccag acccatacca agtaatagaa cagatgggca aagagtcttc cacattctac    33840
ttggaaaagt aacttggtgg gagaacagaa gagaatccag caatagaagg tacagatgtt    33900
agtcttcagc agctctactc cctgccattt ctccaacgct ctgcaaacag gaagtgtgtt    33960
tcatagccat agatccacat cttattgagt ttgtttatat gccaagacca tgctgagcac    34020
tgttctcatc atacgtagtt agcgtcatat atagttctca ccacagccta tggttatcag    34080
tatcccactt tacagagaag gaaactgaca ttcacagtac ccagctggta tagttgaacc    34140
tagaattgac cagactgtcc cctccaaagc ctggattctt attccaggag gccatcagg    34200 aaagctgaca aacacaaagc cattttccaa gagcccttgg gactgaacag gtcaagggtc    34260
ctctgaagat tgtctggatt caggatgcaa gggtgggagt ggagcatgtg cccacaatcc    34320
acagtgtgtt ctgtggctag atccttgcca aatgcaacca cctcccttcg gctgaattct    34380
gtaaggataa aagagtccac cccaaaaagc atggccggaa agtcagggga gggctccaag    34440
ccttcctggt caaacgatcc atcagccaga aaaacccatg tatgacctca acaactaagg    34500
attactgttt cattgtatttt cagaatgtgt agtttcataa gatctgggtc tgatttctgg    34560
tgttagtttc tgagtccaca tgtgtggaac agactccaac ccttaccaca tagaataggga    34620
```

-continued

```
actttggtct atttggggag gtgtaggcat tacattgggc taaaggttat gacagggttt   34680
gctatcatga cttaaggtga tcctcactga atttgttatt ccaccatcat tatctcactg   34740
tttcagagca actgatacat ttttttatttt gacattttac tgtaaaaatg acttttctct   34800
atgtcttctt ccacagcatg aaaaccaaat tattcataga gatctgaaag cagaaaatgt   34860
attctatacc agtaatactt gtgtgaaggt gggcgatttt ggattcagca cagtaagcaa   34920
aaaaggtgaa atgctgaaca ctttctgtgg gtctcctccc tacgctgcgc ctgaactctt   34980
ccgggacgag cactacatcg gcatttacgt ggatatctgg gccttggggg tgcttttgta   35040
cttcatggtg actggcacca tgccatttcg ggcagaaacc gtggccaaac taaaaaagag   35100
catcctcgag ggcacataca gtgtaccgcc gcacgtgtca gagccctgcc accgactcat   35160
ccgaggagtc cttcagcaga tccccacgga gaggtacgga atcgactgca tcatgaatga   35220
tgaatggatg caagggtgc cataccctac acctttggaa cctttccaac tggatcccaa   35280
acatttgtcg gaaaccagca ctctcaagga agaagaaaat gaggtcaaaa gcactttaga   35340
acatttgggc attacagaag agcatattcg aaataaccaa gggagagatg ctcgcagctc   35400
aatcacaggg gtctatagaa ttatttaca tagagtccaa aggaagaagg ctttggaaag   35460
tgtcccagtc atgatgctac cagaccctaa agaaagagac ctcaaaaaag ggtcccgtgt   35520
ctacagaggg ataagacaca catccaaatt ttgctcgatt ttataaattg cactagactg   35580
cttgtaacta accaagatga ttgttgctgc ttctaaattt ttttcaagga caacttgagt   35640
ggagacattt ttgtaatttt taaataaact taaatttgag atatgcattt tttttctcca   35700
aaaagtctat tagctcagat tctggcttga tttgggatct tgttttatta tcaaatttca   35760
gcattcattc atttaatcaa gaaatattta tccagtgcct cctgtgtgtc aggcactatt   35820
taaggtgcta gggaaacagc aagaaataaa taggcaaggt ccctcctctc atgtgcagga   35880
cgttctagcc caggacaaag gtactaacaa ctacattttt taaaaagag aaagatcagt   35940
gatagatgct atgcagagga ttcaaaaagg gtgatctgat atcagaggct tgctactttg   36000
gattagtcat taaggaaggc cactttgagt acatataagt ttaagatctg aatgagaagc   36060
aggagtgact tttacaaaat gccagagcat tccaggcagc tagggggtttc agactcagtt   36120
ccccccaaaa cagagcctaa gacaaaggct tccatataaa gtagtttatt tgggaactga   36180
tcccagagca caggagtgaa ggacagagga acagggaaa gctaatacac agacacatta   36240
gcaagttagc tagtgctaca gtttctggtg cttggttttg caggatcctc cagaggagcc   36300
tgatgaaaca catctcaggt gtctgccctg ggtatgaaag gggaaagcat ttaaccataa   36360
gctcttgctc accgctgatc aagggtggcc cttttgtgtca tctgccctgc actcccagat   36420
tgggctgtgt gaatgccaag tgggttccct aagcttccct tgccttcatg tcagagaagt   36480
cttggagcag gagggaagag gtacaccacc agtacgatac ctcctttctt tgcctgcttg   36540
tccactggca tggggagccc aaagtgacca tgtgacactt gtagattcca attcactgga   36600
gcccttatca agtcccctga tgaaagcatc cctgatcccc tgggaaccaa accttttaat   36660
ctagcctaga ttgtagaaaa aaaaagaata gaaattaatc aagtgagtca ccaattgcgt   36720
gatggtgaca ggagtcaatc tacttccacc tagtggtttc cagacctgtg ttttaatgat   36780
agggacatgt atcagtcatt attaaagcat gttactgaat cctggaggac agcacccaa   36840
ccctgcaggc tgctgtctca tctctggtgt cttagctgag tcattccatt gttctactca   36900
tgttggctgc ttcgatgtt gaggtatatg gtaagatgag gggatcccgt tgtcatgtgc   36960
ccattgcacc acctccttta tcaaaaaagt ggtccttgag gcaatgtttg agatatcatg   37020
```

-continued

```
acagtgagtc agttattctc tatgtcttag tgtgcttgta tggaaagaca cattgcaggc    37080
agaaaaggca aacccatacc ctgagatatc aattccaata aggatgaatc actcctgggc    37140
ccatctgaat tcatgactcc atggatctga taatgcccag ctcatacgtt aacagctctg    37200
tttgcctagt cctcagtatc tcataatcag gttctcagcc tccactgggg cccagtagca    37260
catcgggagt ctgagtagtt ctgtcgcagg aagcatggcg ttactacagg atcccacaga    37320
gctgtgctgt tatctcttat tgggctttc  cagaggcccc acactacaca gcctgagtag    37380
cagtttgctc agaagccaaa attgctgcaa tctttctttt atgggatcca cttgaaactg    37440
gcagccgtgt taaatgggtg ggaggaatac accagataca atatatgtgc ttccaaagtc    37500
cagagggacc tactaaatcc tatgcctcta tcttagtgtt aagaggtggg aggtgcaaga    37560
aattgttctt tactatagaa gaaatatcta ggcatgcctc aactcattgg tcttctaaac    37620
tcttcatcaa tgtggcatgc cccagattct tcatagagtc tataatccac accctggcac    37680
atgtaagcct tactagggca ttggtaatac ttgccacttc ctgatagcca atcccctag     37740
catgctctca caatatagtg ggccagcatg atgtcctgta gaatgtcaag atgatcaagg    37800
tcctttgga  ttatattgtg atatagagaa ggagatttaa gattgttttg gggcaataga    37860
gtaaatgaga atcgctctcc atcccagaga aatgtgaact gcttttgatc ctcctttctg    37920
atggaaattt agaagaatga atttgccaaa tcaatagctg catatcaaat gccagaggct    37980
gccagtaaag ataccacatc caatatggca gctacaactg agactagcag tagtccacca    38040
tcattctcca ttatccatct gctctttttc agaagtgtaa tggtaactta aatgagatta    38100
tgatggagcc cattacactt gcatcccaaa attttttgat ggtgacactg atgtctgcca    38160
ttcctcatgt ggattgctca tgatttatta acatggccag aaagaggttt cctctttctc    38220
ccataatggt tgttacttca caggtctaag acctccacag aggtctaagt atattgatcc    38280
caaatatgta cttagaggtt gggagaataa ttccaaggtg ggaaccatta tgtgatagac    38340
tttggccagg actccctta  tcatatggtt tccataaccc ctcatctacg tacaaagcca    38400
taatggtatc cggttctgaa aaattctggg tatgtacatc atatatactt gtgaaagcaa    38460
ggcctttcct caagaccagt cctccttttc attgtgcact ggatctgtaa attgacttag    38520
ctctggaagc tgatgaagag accgtgattt tcccattgtg acag                     38564
```

<210> SEQ ID NO 4
<211> LENGTH: 290
<212> TYPE: PRT
<213> ORGANISM: Caenorhabditis elegans

<400> SEQUENCE: 4

```
Gln Val Ala Leu Gly Arg Arg Ile Gly Phe Tyr Arg Leu Gly Lys Glu
 1               5                   10                  15

Leu Gly Ala Gly Asn Phe Ser Lys Val Lys Leu Gly Val His Gln Leu
                20                  25                  30

Thr Lys Glu Lys Val Ala Val Lys Ile Met Asp Lys Ala Lys Met Asp
            35                  40                  45

Ala Lys Ala Gln Lys Leu Leu Ser Arg Glu Ile Gln Ala Met Glu Glu
        50                  55                  60

Met Asn His Pro Asn Ile Val Lys Leu Phe Glu Val Val Glu Thr Leu
 65                  70                  75                  80

Thr Arg Val His Leu Val Ile Glu Tyr Ala Ser Gly Gly Glu Leu Tyr
                85                  90                  95
```

```
Thr Tyr Val His Glu Arg Gly Lys Leu Thr Glu Gly Asp Ala Lys Pro
            100                 105                 110

Leu Phe Ala Gln Ile Val Ser Ala Val Ser His Met His Ser Arg Asn
            115                 120                 125

Ile Val His Arg Asp Ile Lys Ala Glu Asn Val Met Phe Ser Ser Pro
        130                 135                 140

Asn Thr Val Lys Leu Val Asp Phe Gly Phe Ser Cys Leu Val Asp Arg
145                 150                 155                 160

Glu Gln Met Leu Arg Thr Phe Cys Gly Ser Pro Pro Tyr Ala Ala Pro
                165                 170                 175

Glu Leu Phe Gln Asp Thr Ser Tyr Ala Gly Glu Leu Val Asp Val Trp
            180                 185                 190

Ala Leu Gly Val Leu Leu Phe Met Leu Ile Gly Val Thr Pro Phe
            195                 200                 205

Lys Ala Glu Thr Val Pro Asp Met Lys Val Leu Ile Thr Ala Gly Lys
        210                 215                 220

Tyr Gln Ile Pro Asp Tyr Val Ser Leu Leu Ala Thr Glu Leu Ile Lys
225                 230                 235                 240

Ser Met Leu Lys Thr Asp Thr Gly Gln Arg Ala Asp Ile Asp Ser Val
                245                 250                 255

Lys Lys His Phe Trp Met Arg Asp Cys Arg Phe Thr Lys Ser Tyr Leu
            260                 265                 270

Ser Ile Lys Ala Thr Ala Lys Ile Asp Asn Glu Glu Lys Lys Ala
            275                 280                 285

Ile Asp
    290

<210> SEQ ID NO 5
<211> LENGTH: 268
<212> TYPE: PRT
<213> ORGANISM: Drosophila melanogaster

<400> SEQUENCE: 5

Gln Val Thr Ile Gly Arg Arg Ile Gly Leu Tyr Arg Phe Cys Gly Asp
  1               5                  10                  15

Ile Gly Arg Gly Asn Phe Ser Lys Val Lys Leu Ala Val His Gln Leu
            20                  25                  30

Thr Arg Asp Lys Val Ala Ile Lys Val Val Asp Leu Asp Arg Ala Gly
        35                  40                  45

Leu Asp Ala Lys Ala Leu Arg Met Leu Ser Ser Glu Ile Ala Thr Leu
 50                  55                  60

Glu Cys Val His His Pro Asn Ile Leu Arg Leu Phe Glu Val Val Glu
65                  70                  75                  80

Thr Leu Gly Arg Val Tyr Leu Val Thr Glu Trp Ile Arg Gly Gly Glu
                85                  90                  95

Leu Tyr Asn His Ile Thr Gln Gly Gly Pro Leu Arg Glu Ile His Ala
            100                 105                 110

Ala Pro Leu Leu Lys Gln Leu Leu Ala Val Lys His Met His Ser
        115                 120                 125

Leu Gly Tyr Val His Arg Asp Ile Lys Ala Glu Asn Val Leu Leu Leu
        130                 135                 140

Ser Glu Asp Arg Leu Lys Leu Ala Asp Phe Gly Phe Ser Thr Gln Leu
145                 150                 155                 160

Ile Asn Gly Thr Gly Ala Asn Gln Lys Leu Asp Thr Phe Cys Gly Ser
                165                 170                 175
```

```
Pro Pro Tyr Ala Ala Pro Glu Leu Phe Ser Asp Asp His Tyr Ile Gly
            180                 185                 190

Ala Pro Val Asp Val Trp Ala Leu Gly Ile Leu Leu Tyr Phe Met Val
        195                 200                 205

Val Gly Asn Met Pro Phe Arg Ala Pro Thr Ile Pro Gly Leu Lys Ala
        210                 215                 220

Ala Ile Leu Lys Gly Asp Tyr Leu Leu Pro Gly Gln Leu Ser Leu Pro
225                 230                 235                 240

Cys Ile Arg Leu Ile Gln Arg Ile Leu Ile His Ile Pro Ala Gln Arg
                245                 250                 255

Pro Thr Ile Asp Asp Met Leu Asn Ser Gln Phe Val
            260                 265

<210> SEQ ID NO 6
<211> LENGTH: 74
<212> TYPE: PRT
<213> ORGANISM: Human

<400> SEQUENCE: 6

Pro Thr Asn Thr Glu Asp Leu Ser Gln Leu Gly Ala Leu Glu Phe Glu
1               5                   10                  15

Ala Arg Gln Ile Leu Ala Glu Leu Gly Leu Thr Ser Glu Met Leu Ile
            20                  25                  30

Asn Ala Arg Gln Ser Gly Pro Arg Ser Asp Ile Ile Gly Ala Tyr Arg
            35                  40                  45

Ile Val Val Asn Arg Leu Gln Lys Gln Ser Trp Leu Ala Arg Lys His
            50                  55                  60

Val Glu Met Ala Leu His Ser Glu Pro Lys
65                  70
```

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the SNF-like kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for con trolling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest, known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:367–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL- 1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

SNF Kinases

The kinase proteins of this invention are homologous to the SNF kinases, involved in signal transduction and development. SNF kinases derepress glucose-repressible genes in yeast and in higher plants. SNF-like kinases are also found in mammals. For example, the hunk1 kinase is expressed in murine mammary gland and may play a role in tissue development and carcenogenesis. Also, msk (myocardial SNF1-like kinase) is expressed in developing heart. Experimental evidence indicates that msk regulates HEK kinase, an ephrin receptor type kinase. For more information on SNF-like kinases, see Bielke W, et al., *Gene* Feb. 25, 1994;139(2):235–9; Le Guen L, et al., *Gene* Oct. 21, 1992;120(2):249–54; Gardner H P, et al., *Genomics* Jan. 1, 2000;63(1):46–59; Ruiz J C, et al., *Mech Dev* 1994 Dec;48 (3):153–64; and Yoshida E N, et al., *Genome* 1999 Dec;42 (6):1077–87.

Kinase proteins, particularly members of the SNF-like kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the SNF-like kinase subfamily.

SUMMARY OF THE INVENTION

The present invention is based in part on the identification of amino acid sequences of human kinase peptides and proteins that are related to the SNF-like kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in lung, liver, kidney, thyroid, brain, infant brain, fetal brain, placenta, bone marrow, germ cell tissue, germ cell tumor tissue, and primary cancers.

DESCRIPTION OF THE FIGURE SHEETS

FIG. 1 provides the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in lung, liver, kidney, thyroid, brain, infant brain, fetal brain, placenta, bone marrow, germ cell tissue, germ cell tumor tissue, and primary cancers.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, known SNP variations include C1681A, T6888-, A7939G, G9790A, G11689A, A12145G, A12437-, A12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the SNF-like kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the SNF-like kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the SNF-like kinase subfamily and the expression pattern observed. Experimental data as provided in FIG. 1 indicates expression in lung, liver, kidney, thyroid, brain, infant brain, fetal brain, placenta, bone marrow, germ cell tissue, germ cell tumor tissue, and primary cancers. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known SNF-like kinase family or subfamily of kinase proteins.

Specific Embodiments

Peptide Molecules

The present invention provides nucleic acid sequences that encode protein molecules that have been identified as being members of the kinase family of proteins and are related to the SNF-like kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in lung, liver, kidney, thyroid, brain, infant brain, fetal brain, placenta, bone marrow, germ cell tissue, germ cell tumor tissue, and primary cancers. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene provided by the present invention is located on a genome component that has been mapped to human chromosome 5 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene provided by the present invention is located on a genome component that has been mapped to human chromosome 5 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in a gene encoding the kinase proteins of the present invention. The following variations were seen: C1681A, T6888-, A7939G, G9790A, G11689A, A12145G, A12437-, A 12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T. The changes in the amino acid sequence that these SNPs cause can readily be determined using the universal genetic code and the protein sequence provided in FIG. 2 as a base.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (Meth. Enzymol. 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta. A large percentage of pharmaceutical agents are being developed that modulate the activity of kinase proteins, particularly members of the SNF-like kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in lung, liver, kidney, thyroid, brain, infant brain, fetal brain, placenta, bone marrow, germ cell tissue, germ cell tumor tissue, and primary cancers. Such uses can readily be determined using the information provided herein, that which is known in the art, and routine experimentation.

The proteins of the present invention (including variants and fragments that may have been disclosed prior to the present invention) are useful for biological assays related to kinases that are related to members of the SNF-like kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in lung, liver, kidney, thyroid, brain, infant brain, fetal brain, placenta, bone marrow, germ cell tissue, germ cell tumor tissue, and primary cancers. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in lung, liver, kidney, thyroid, brain, infant brain, fetal brain, placenta, bone marrow, germ cell tissue, germ cell tumor tissue, and primary cancers. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in lung, liver, kidney, thyroid, brain, infant brain, fetal brain, placenta, bone marrow, germ cell tissue, germ cell tumor tissue, and primary cancers. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (Clin. Chem 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in lung, liver, kidney, thyroid, brain, infant brain, fetal brain, placenta, bone marrow, germ cell tissue, germ cell tumor tissue, and primary cancers. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in lung, liver, kidney, thyroid, brain, infant brain, fetal brain, placenta, bone marrow, germ cell tissue, germ cell tumor tissue, and primary cancers. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in lung, liver, kidney, thyroid, brain, infant brain, fetal brain, placenta, bone marrow, germ cell tissue, germ cell tumor tissue, and primary cancers. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in lung, liver, kidney, thyroid, brain, infant brain, fetal brain, placenta, bone marrow, germ cell tissue, germ cell tumor tissue, and primary cancers. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene provided by the present invention is located on a genome component that has been mapped to human chromosome 5 (as indicated in FIG. 3), which is supported by multiple lines of evidence, such as STS and BAC map data.

FIG. 3 provides information on SNPs that have been found in a gene encoding the kinase proteins of the present invention. The following variations were seen: C1681A, T6888-, A7939G, G9790A, G11689A, A12145G, A12437-, A12437G, G12437-, C22982T, C23239T, A23859G, G24862A, G25097A, C25751 T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T. The changes in the amino acid sequence that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, known SNP variations include C1681A, T6888-, A7939G, G9790A, G11689A, A12145G, A12437-, A12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene provided by the present invention is located on a genome component that has been mapped to human chromosome 5 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in lung, liver, kidney, thyroid, brain, infant brain, fetal brain, placenta, bone marrow, germ cell tissue, germ cell tumor tissue, and primary cancers. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in lung, liver, kidney, thyroid, brain, infant brain, fetal brain, placenta, bone marrow, germ cell tissue, germ cell tumor tissue, and primary cancers.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in a gene encoding the kinase proteins of the present invention. The following variations were seen: C1681A, T6888-, A7939G, G9790A, G11689A, A12145G, A12437-, A12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T. The changes in the amino acid sequence that these SNPs cause can readily be determined using the universal genetic code and the protein sequence provided in FIG. 2 as a base. The gene provided by the present invention is located on a genome component that has been mapped to human chromosome 5 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 21 7:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in a gene encoding the kinase proteins of the present invention. The following variations were seen: C1681A, T6888-, A7939G, G9790A, G11689A, A12145G, A12437-, A12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T. The changes in the amino acid sequence that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates expression in lung, liver, kidney, thyroid, brain, infant brain, fetal brain, placenta, bone marrow, germ cell tissue, germ cell tumor tissue, and primary cancers. Specifically, a virtual northern blot shows expression in lung, infant brain, germ cell tissue, germ cell tumor tissue, and primary cancers. In addition, PCR-based tissue screening panel indicates expression in liver, kidney, bone marrow, thyroid, brain, fetal brain, and placenta. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in a gene encoding the kinase proteins of the present invention. The following variations were seen: C1681A, T6888-, A7939G, G9790A, G11689A, A12145G, A12437-, A12437G, G12437-, C22982T, C23239T, A23859G, G24862A, G25097A, C25751T, T25934-, G26179A, A26277G, -26354T, T26356-, T26359G, G29484A, A29885T, C30601T, C30920T, C31057A, C31057G, G31097A, T31204C, T32660A, T32875-, C33477G, C34059T, -36681A, C36821T, A38079G, and A38432T. The changes in the amino acid sequence that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al, *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The "term vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11 (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al, *Nucleic Acids Res.* 20:2111–2118 (1992)).

The nucleic acid molecules can also be expressed by expression vectors that are operative in yeast. Examples of vectors for expression in yeast e.g., S. cerevisiae include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S. cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence consisting of SEQ ID NO:1;
   (b) a nucleotide sequence consisting of SEQ ID NO:3; and
   (c) a nucleotide sequence that is completely complementary to a nucleotide sequence of (a)–(b).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide from the host cell culture.

5. An isolated polynucleotide consisting of a nucleotide sequence set forth in SEQ ID NO: 1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the nucleic acid molecule may be expressed by a cell transformed with said vector.

9. A vector according to claim 8, wherein said isolated nucleic acid molecule is operatively linked to a promoter sequence.

* * * * *